:

US006306628B1

(12) United States Patent
Rothschild et al.

(10) Patent No.: US 6,306,628 B1
(45) Date of Patent: Oct. 23, 2001

(54) METHODS FOR THE DETECTION, ANALYSIS AND ISOLATION OF NASCENT PROTEINS

(75) Inventors: Kenneth J. Rothschild, Newton; Sadanand Gite, Cambridge; Jerzy Olejnik, Allston, all of MA (US)

(73) Assignee: Ambergen, Incorporated, Boston, MA (US)

( * ) Notice: Subject to any disclaimer, the term of this patent is extended or adjusted under 35 U.S.C. 154(b) by 0 days.

(21) Appl. No.: 09/382,736

(22) Filed: Aug. 25, 1999

(51) Int. Cl.[7] ............... C12P 19/34; C12P 21/04; C07H 21/02; C07K 1/00
(52) U.S. Cl. .............. 435/91.3; 435/69.1; 530/350; 536/23.1; 536/25.3
(58) Field of Search .................. 435/68.1, 183, 435/91.3, 69.1; 536/23.1, 25.3; 530/350

(56) References Cited

U.S. PATENT DOCUMENTS

| 4,675,285 | 6/1987 | Clark et al. ...................... 435/6 |
| 4,683,195 | 7/1987 | Mullis et al. ..................... 435/6 |
| 4,774,339 | 9/1988 | Haugland et al. ............... 548/405 |
| 5,069,769 | 12/1991 | Fujimiya et al. ................ 204/461 |
| 5,091,328 | 2/1992 | Miller ............................. 438/278 |
| 5,137,609 | 8/1992 | Manian et al. ................... 204/452 |
| 5,187,288 | 2/1993 | Kang et al. ..................... 548/110 |
| 5,190,632 | 3/1993 | Fujimiya et al. ................ 204/608 |
| 5,248,782 | 9/1993 | Haugland et al. ............... 548/110 |
| 5,274,113 | 12/1993 | Kang et al. ..................... 548/405 |
| 5,433,896 | 7/1995 | Kang et al. ..................... 252/700 |
| 5,451,663 | 9/1995 | Kang et al. ..................... 530/367 |
| 5,614,386 | 3/1997 | Metzker et al. ................. 435/91.1 |
| 5,622,829 | 4/1997 | King et al. ...................... 435/6 |
| 5,643,722 | 7/1997 | Rothschild et al. .............. 435/6 |
| 5,693,473 | 12/1997 | Shattuck-Eidens et al. ...... 435/6 |
| 5,709,998 | 1/1998 | Kinzler et al. ................... 435/6 |
| 5,760,207 | 6/1998 | Kinzler et al. ................... 536/24.3 |
| 5,783,397 | 7/1998 | Hughes et al. ................... 435/7.1 |
| 5,861,494 | 1/1999 | Soppet et al. .................... 536/23.1 |
| 5,879,890 | 3/1999 | Laken et al. ..................... 435/6 |

FOREIGN PATENT DOCUMENTS

| 0 234 799 | 9/1987 | (EP) ................... C12P/21/02 |
| WO90/05785 | 5/1990 | (WO) . |

OTHER PUBLICATIONS wysiwyg://63/http://www.probes.com/handbook/figures/0103.html (Molecular Probes, Inc., Eugene, OR internet site).*

Shore et al., "A Fluorescent Probe Capable of Incorporation into Nascent Polypeptide Chains," 1986 *Federation Proceedings* 45, 1566 Abstract.

Shore et al., "Accessibility of AA–tRNA and Nascent Chain During Protein Synthesis," 1988 *FASEB Journal* 2, A1045 Abstract.

Bain et al., "Site–Specific Incorporation of Non–Natural Residues into Peptides: Effect of Residue Structure on Suppression and Translation Efficiencies," *Tetrahedron* 47:2389–2400 (1991).

Johnson et al., "N–Acetyllysine Transfer Ribonucleic Acid: A Biologically Active Analogue of Aminoacyl Transfer Ribonucleic Acids," *Biochemistry* 15:569–575 (1976).

(List continued on next page.)

*Primary Examiner*—Robert A. Schwartzman
*Assistant Examiner*—Katharine F Davis
(74) *Attorney, Agent, or Firm*—Medlen & Carroll, LLP

(57) ABSTRACT

This invention relates to non-radioactive markers that facilitate the detection and analysis of nascent proteins translated within cellular or cell-free translation systems. Nascent proteins containing these markers can be rapidly and efficiently detected, isolated and analyzed without the handling and disposal problems associated with radioactive reagents. Preferred markers are dipyrromethenboron difluoride (4,4-difluoro-4-bora-3a,4a-diaza-s-indacene) dyes.

26 Claims, 35 Drawing Sheets

OTHER PUBLICATIONS

Johnson, "Chemically Modified Aminoacyl–tRNA as a Probe of Ribosome Structure: the Synthesis and in vitro Activity of ε–N–acetyl–Lys–tRNA," 1973 Thesis Excerpts, University of Oregon, Eugene, Oregon.

Shore, "The Use of Fluorescent–Labeled Amino Acids to Examine the Environment of Ribosome–Bound Nascent Polypeptide Chains," 1991 Dissertation, University of Oklahoma, Norman Oklahoma.

Karginov et al., "Facile characteriation of translation initiation via nonsense codon suppression," *Nucleic Acids Res.* 27:3283–90 (1999).

Kramer et al., "In Vitro engineering using synthtic tRNAs with altered anticodons including four–nucleotide anticodons," *Methods Mol. Biol.* 77:105–16 (1998).

Kramer et al., "N–terminal and C–terminal modifications affect of in vitro synthesized proteins," *Int J Biochem Cell Biol.* 31:231–41 (1999).

Odem et al., "In Vitro engineering using acylderivatized tRNAs," *Methods Mol Biol.* 77:93–103 (1998).

Tsalkova et al., "The effect of a hydrophobic N–terminal probe on translational pausing of chloramphenicol acetyl transferase and rhodanese," *J Mol Biol.* 286:71–81 (1999).

Nemoto et al., "Fluorescence labeling of the C–terminus of proteins with a puromycin analogue in cell–free translation systems," *FEBS Letters.* 462:43–46 (1999).

Hudson, "Methodological Implications of Simultaneous Solid–Phases Peptide Synthesis. 1. Comparison of Different Coupling Procedures," *J. Org. Chem.* 53:617–624 (1988).

Stephen, "High–Resolution Preparative SDS–Polyacrylamide Gel Electrophoresis: Fluorescent Visualization and Electrophoretic Elution–Concentration of Protein Bands," *Anal. Biochem.* 65:369–79 (1975).

Crowley et al., "The signal sequence moves through a ribosomal tunnel into a noncytoplasmic aqueous environment at the ER membrane early in translocation," *Cell* 73:1101–1115 (1993).

Karolin et al., "Fluorescence and Absorption Spectroscopic Propertes of Dipyrrometheneboron Difluoride (BODIPY) Derivatives in Liquids, Lipid Membranes, and Proteins," *J. Am. Chem. Soc.* 116:7801–7806 (1994).

Hardesty et al., "Extension and Folding of Nascent Peptides on Ribosomes." *The Translational Apparatus*, Nierhaus et al. ed: New York and London; Plenum Press. p. 347–358 (1993).

Johnson et al., "Protein Synthesis and Secretion as seen by the Nascent Protein Chain," *The Translational Apparatus*, Nierhaus et al. ed: New York and London; Plenum Press. p. 359–370 (1993).

Allen et al., *Gel Electrophoresis and Isoelectric Focusing of Proteins*, Walter de Gruyter, New York 1984, pp. 17–62.

*Antibodies: A Laboratory Manual* (E. Harlow and D. Lane, editors, Cold Spring Harbor Laboratory Press, 1988, pp. 53,72–73).

Bain et al., "Site–Specific Incorporation of Nonnatural Residues during In Vitro Protein Biosynthesis with Semisynthetic Aminoacyl–tRNAs," *Biochemistry* 30:5411–21 (1991).

Bruce and Uhlenbeck, "Specific Interaction of Anticodon Loop Residues with Yeast Phenylalanyl–tRNA Synthetase," *Biochemistry* 21:3921–3926 (1982).

*Current Protocols in Molecular Biology* (F.M. Ausubel et al. editors, Wiley Interscience, 1993), pp. 10–16, 10–77.

Da Poian, A. T., et al., "Kinetics of intracellular viral disassembly and processing probed by Bodipy fluorescence dequenching," *J Virol Methods* 70(1), 45–58 (1998).

Doty et al., "Strand Separation and Specific Recombination in Deoxyribonucleic Acids: Physical Chemicals Studies," *Proc. Natl. Acad. Sci. USA* 46:461 (1960).

DiCesare et al., "A High–Sensitivity Electrochemiluminescence–Based Detection System for Automated PCR Product Quantitation," *BioTechniques* 15:152–59 (1993).

Felgner et al., "Lipofection: A highly efficient, lipid–mediated DNA–transfection procedure," *Proc. Natl. Acad. Sci. USA* 84:7413–17 (1987).

Happ et al., "New Approach to the Synthesis of 2'(3')–O–Aminoacyl Oligoribonucleotides," *J. Org. Chem.* 52:5387–91 (1987).

Heckler et al., "Preparation of 2'(3')–O–Acyl–pCpA Derivatives as Substrates for T4 RNA Ligase–Mediated "Chemical Aminoacylation"," *Tetrahedron* 40:87–94 (1984).

Heckler et al., "T4 RNA Ligase Mediated Preparation of Novel "Chemically Misacylated" tRNA$^{Phe}$S," *Biochemistry* 23:1468–73 (1984).

Hemmila, I.A., *Chemical Analysis* "Applications of Fluorescence in Immunoassays", (Wiley&Sons 1991) pp. 138–159.

Krieg et al., "Photocrosslinking of the signal sequence of nascent preprolactin to the 54–kilodalton polypeptide of the signal recognition particle," *Proc. Natl. Acad. Sci. USA* 83:8604–08 (1986).

Keller, R. C., et al., "Characterization of the Resonance Energy Transfer Couple Coumarin–Bodipy and its Possible Applications in Protein–Lipid Research," *Biochem Biophys Res Commun* 207(2), 508–14 (1995).

Kim, D., and Choi, C., "A Semicontinuous Prokaryotic Coupled Transcription/Translation System Using a Dialysis Membrane," *Biotechnol Prog* 12, 645–649 (1996).

Kopp et al., "Chemical Amplification: Continuous Flow PCR on a Chip," *Science* 280:1046 (1998).

Kozak, "Point Mutations Define a Sequence Flanking the AUG Initiator Codon that Modulates Translation by Eukaryotic Ribosomes," *Cell* 44:283–292 (1986).

Kudlicki, W.et al., "Chaperone–dependent Folding and Activation of Ribosome–bound Nascent Rhodanse," *J Mol Biol* 244(3), 319–31 (1994).

Laemmli, U. K., "Cleavage of Structural Proteins during the Assembly of the Head of Bacteriophage T4," *Nature* 227:680–685 (1970).

Marmur and Lane, "Strand Separation and Specific Recombination in Deoxyribonucleic Acids: Biological Studies," *Proc. Natl. Acad. Sci. USA* 46:453–461 (1960).

*Molecular Cell Biology* (J. Darnell et al. editors, Scientific American Books, N.Y., N.Y. 1991) pp. 199–132.

Neu and Heppel, "Nucleotide Sequence Analysis of Polyribonucleotides by Means of Periodate Oxidation Followed by Cleavage with an Amine," *J. Biol. Chem.* 239:2927–34 (1964).

Noren et al., "A General Method for Site–Specific Incorporation of Unnatural Amino Acids into Proteins," *Science* 244:182–188 (1989).

Patchornik et al., "Photosensitive Protecting Groups," *J. Am. Chem. Soc.* 92:6333–35 (1970).

Pavlopoulos, et al., "Laser action from a tetramethylpyrromethene–BF$_2$ complex," *APP. Optics* 27:4998–4999 (1988).

Pillai, "Photoremovable Protecting Groups in Organic Synthesis," *Synthesis* 1–26 (1980).
Powell et al., "Molecular Diagnosis of Familial Adenomatous Polyposis," *N. Engl. J. Med.* 329:1982–87 (1993).
Pratt, "Coupled Transcription–Translation in Prokaryotic Cell–Free System," (*Transcription and Translation*, B.D. Hames and S.J. Higgins, Editors, p. 179–209, IRL Press, Oxford, 1984).
Promega Technical Bulletin No. 182; tRNA$^{nscend}$™: Non-radioactive Translation Detection System, Sep. 1993.
Reis, R. C., et al., "A novel methodology for the investigation of intracellular proteolytic processing in intct cells," *Eur J Cell Biol* 75(2), 192–7 (1988).
Rowan and Bodmer, "Introduction of a myc Reporter Taq to Improve the Quality of Mutation Detection Using the Protein Truncation Test," *Human Mutation* 9:172–176 (1997).
Sampson and Uhlenbeck, "Biochemical and physical characterization of an unmodified yeast phenylalanine transfer RNA transcribed in vitro," *Proc. Natl. Acad. Sci. USA* 85:1033–37 (1988).
Seong and RajBhandary, "*Escherichia coli* formylmethione tRNA: Mutations in $^{GGG}$ sequence conserved in anticodon stem of initiator tRNAs affect initiation of protein synthesis and conformation of anticodon loop," *Proc. Natl. Acad. Sci. USA* 84:334–338 (1987).
Spirin et al., "A Continous Cell–Free Translation System Capable of Producing Polypeptides in High Yield," *Sci.* 242:1162–64 (1988).
Treibs & Kreuzer, "Difluorboryl–komplexe von di– und tripyrrylmethenen," *Liebigs Ann. Chem.* 718:208–223 (1968).
Turcatti et al., "Probing the Structure and Function of the Tachykinin Neurokinin–2 Receptor through Biosynthetic Incorporation of Fluorescent Amino Acids at Specific Sites," *J Biol Chem* 271(33), 19991–8 (1996).
Varshney U, RajBhandary UL, "Initiation of protein synthesis from a termination codon," *Proc Natl Acad Sci U S A* 87(4):1586–90 (1990).
Varshney et al., "Direct Analysis of Aminoacylation Levels of tRNAa in Vivo," *J. Biol. Chem.* 266: 24712–24718 (1991).

Yao S et al., "SDS capillary gel electrophoresis of proteins in microfabricated channels," *PNAS* 96:5372–5377 (1999).
Vecesey–Semjen et al., "The Staphylococcal α–Toxin Pore Has a Flexible Conformation," *Biochemistry* 38 4296–4302 (1999).
Walker, B. et al., "Functional Expression of the α–Hemolysin of *Staphylococcus aureus* in Intact *Escherichia coli* and in Cell Lysates," *J. Biol. Chem.* 267:10902–10909 (1992).
Czworkowski et al., "Fluorescence Study of the Topology of Messenger RNA Bound to the 30S Ribosomal Subunit of *Escherichia coli,* " *Biochemistry* 30:4821–4830 (1991).
Hardesty et al., "Ribosome function determined by fluorescence," *Biochimie* 74:391–401 (1992).
Kudlicki et al., "Chaperone–dependent Folding and Activation of Ribosome–bound Nascent Rhodanese," *J. Mol. Biol.* 244:319–331 (1994).
Picking et al., "The use of synthetic tRNA as probes for examing nascent peptides on *Escherichia coli* ribosomes," *Biochimie* 73:1101–1107 (1991).
Picking et al., "Evidence for RNA in the Peptidyl Transferase Center of *Escherichia coli* Ribosomes as Indicated by Fluorescence," *Biochemistry* 31:12565–12570 (1992).
Picking et al., "The Conformation of Nascent Polylysine and Polyphenylalanine Peptides on Ribosomes," *J. of Biological Chemistry* 266:1534–1542 (1991).
Picking et al., "Fluorescence Characterization of the Environment Encountered by Nascent Polyalanine and Polyserine as They Exit *Escherichia coli* Ribosomes during Translation," *Biochemistry* 31:2368–2375 (1992).
Picking et al., "A synthetic alanyl–initiator tRNA with initiator tRNA properties as determined by fluorescence measurements: Comparison to a synthetic alanyl–elongator tRNA," *Nucleic Acids Research* 19:5749–5754 (1991).
Ma et al., "In Vitro Protein Engineering Using Synthetic tRNA$^{Ala}$ with Different Anticodons," *Biochemistry* 32:7939–7945 (1993).
Odom et al., "Movement of tRNA but Not the Nascent Peptide during Peptide Bond Formation on Ribosomes," *Biochemistry* 29:10734–10744 (1990).

* cited by examiner

⁻OOC—ALANINE-VALINE-TYROSINE-LYSINE-TRYPTOPHAN—NH$_3^+$

SEQUENCE LISTING

<160> NUMBER OF SEQ ID NOS: 18

<210> SEQ ID NO 1
<211> LENGTH: 11
<212> TYPE: DNA
<213> ORGANISM: Artificial Sequence
<220> FEATURE:
<223> OTHER INFORMATION: Synthetic

<400> SEQUENCE: 1
gccagccatg g                                                           11

<210> SEQ ID NO 2
<211> LENGTH: 9
<212> TYPE: DNA
<213> ORGANISM: Artificial Sequence
<220> FEATURE:
<223> OTHER INFORMATION: Synthetic

<400> SEQUENCE: 2 uaaggaggu                                                               9

<210> SEQ ID NO 3
<211> LENGTH: 22
<212> TYPE: DNA
<213> ORGANISM: Artificial Sequence
<220> FEATURE:
<223> OTHER INFORMATION: Synthetic
<221> NAME/KEY: misc_feature
<222> LOCATION: (10)..(19)
<223> OTHER INFORMATION: All n's can be a, c, t, or g, and 5 may be
      absent or present

<400> SEQUENCE: 3
uaaggaggun nnnnnnnna ug                                                 22

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Trp Glu Ala Ala Ala Arg Glu Ala Cys Cys Arg Glu Cys Cys Ala Arg
1               5                   10                  15

Ala

<210> SEQ ID NO 5

```
<211> LENGTH: 6
<212> TYPE: PRT
<213> ORGANISM: Artificial Sequence
<220> FEATURE:
<223> OTHER INFORMATION: Synthetic

<400> SEQUENCE: 5

His His His His His His
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Glu Gln Lys Leu Ile Ser Glu Glu Asp Leu
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Asp Tyr Lys Asp Asp Asp Asp Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Trp Ser His Pro Gln Phe Glu Lys
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Tyr Pro Tyr Asp Val Pro Asp Tyr Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Met Trp Ser Pro Gln Phe Glu Lys
1               5

<210> SEQ ID NO 11
<211> LENGTH: 111
```

```
<212> TYPE: DNA
<213> ORGANISM: Artificial Sequence
<220> FEATURE:
<223> OTHER INFORMATION: Synthetic

<400> SEQUENCE: 11
gaattctaat acgactcact atagggttaa ctttaagaag gagatataca tatggaacaa      60
aaattaatct cggaagagga tttggcagat tctgatatta atattaaaac c             111

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
agcttcatta atgatggtga tggtggtgac                                       30

<210> SEQ ID NO 13
<211> LENGTH: 94
<212> TYPE: DNA
<213> ORGANISM: Artificial Sequence
<220> FEATURE:
<223> OTHER INFORMATION: Synthetic

<400> SEQUENCE: 13
ggatcctaat acgactcact atagggagac caccatggaa caaaaattaa tatcggaaga      60
ggatttgaat gtttctccat acaggtcacg ggga                                  94

<210> SEQ ID NO 14
<211> LENGTH: 51
<212> TYPE: DNA
<213> ORGANISM: Artificial Sequence
<220> FEATURE:
<223> OTHER INFORMATION: Synthetic

<400> SEQUENCE: 14
ttattaatga tggtgatggt ggtgttctgt aggaatggta tctcgttttt c               51

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Ala Val Tyr Lys Trp
1               5

<210> SEQ ID NO 16
<211> LENGTH: 33
<212> TYPE: DNA
<213> ORGANISM: Artificial Sequence
<220> FEATURE:
<223> OTHER INFORMATION: Synthetic

<400> SEQUENCE: 16
auguacacua aacaugauga uauccgaaaa uga                                   33

<210> SEQ ID NO 17
<211> LENGTH: 10
<212> TYPE: PRT
<213> ORGANISM: Artificial Sequence
```

```
                                    -continued

<220> FEATURE:
<223> OTHER INFORMATION: Synthetic

<400> SEQUENCE: 17

Met Tyr Thr Lys Asp His Asp Ile Arg Lys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Lys Arg Ile Asp Asp His Lys Thr Tyr Met
1               5                   10
```

METHODS FOR THE DETECTION, ANALYSIS AND ISOLATION OF NASCENT PROTEINS

FIELD OF THE INVENTION

This invention relates to non-radioactive markers that facilitate the detection and analysis of nascent proteins translated within cellular or cell-free translation systems. Nascent proteins containing these markers can be rapidly and efficiently detected, isolated and analyzed without the handling and disposal problems associated with radioactive reagents.

BACKGROUND OF THE INVENTION

Cells contain organelles, macromolecules and a wide variety of small molecules. Except for water, the vast majority of the molecules and macromolecules can be classified as lipids, carbohydrates, proteins or nucleic acids. Proteins are the most abundant cellular components and facilitate many of the key cellular processes. They include enzymes, antibodies, hormones, transport molecules and components for the cytoskeleton of the cell.

Proteins are composed of amino acids arranged into linear polymers or polypeptides. In living systems, proteins comprise over twenty common amino acids. These twenty or so amino acids are generally termed the native amino acids. At the center of every amino acid is the alpha carbon atom (Cα) which forms four bonds or attachments with other molecules (FIG. 1). One bond is a covalent linkage to an amino group ($NH_2$) and another to a carboxyl group (COOH) which both participate in polypeptide formation. A third bond is nearly always linked to a hydrogen atom and the fourth to a side chain which imparts variability to the amino acid structure. For example, alanine is formed when the side chain is a methyl group (—$CH_3$) and a valine is formed when the side chain is an isopropyl group (—$CH(CH_3)_2$). It is also possible to chemically synthesize amino acids containing different side-chains, however, the cellular protein synthesis system, with rare exceptions, utilizes native amino acids. Other amino acids and structurally similar chemical compounds are termed non-native and are generally not found in most organisms.

A central feature of all living systems is the ability to produce proteins from amino acids. Basically, protein is formed by the linkage of multiple amino acids via peptide bonds such as the pentapeptide depicted in FIG. 1B. Key molecules involved in this process are messenger RNA (mRNA) molecules, transfer RNA (tRNA) molecules and ribosomes (rRNA-protein complexes). Protein translation normally occurs in living cells and in some cases can also be performed outside the cell in systems referred to as cell-free translation systems. In either system, the basic process of protein synthesis is identical. The extra-cellular or cell-free translation system comprises an extract prepared from the intracellular contents of cells. These preparations contain those molecules which support protein translation and depending on the method of preparation, post-translational events such as glycosylation and cleavages as well. Typical cells from which cell-free extracts or in vitro extracts are made are *Escherichia coil* cells, wheat germ cells, rabbit reticulocytes, insect cells and frog oocytes.

Both in vivo and in vitro syntheses involve the reading of a sequence of bases on a mRNA molecule. The mRNA contains instructions for translation in the form of triplet codons. The genetic code specifies which amino acid is encoded by each triplet codon. For each codon which specifies an amino acid, there normally exists a cognate tRNA molecule which functions to transfer the correct amino acid onto the nascent polypeptide chain. The amino acid tyrosine (Tyr) is coded by the sequence of bases UAU and UAC, while cysteine (Cys) is coded by UGU and UGC. Variability associated with the third base of the codon is common and is called wobble.

Translation begins with the binding of the ribosome to mRNA (FIG. 2). A number of protein factors associate with the ribosome during different phases of translation including initiation factors, elongation factors and termination factors. Formation of the initiation complex is the first step of translation. Initiation factors contribute to the initiation complex along with the mRNA and initiator tRNA (fmet and met) which recognizes the base sequence UAG. Elongation proceeds with charged tRNAs binding to ribosomes, translocation and release of the amino acid cargo into the peptide chain. Elongation factors assist with the binding of tRNAs and in elongation of the polypeptide chain with the help of enzymes like peptidyl transferase. Termination factors recognize a stop signal, such as the base sequence UGA, in the message terminating polypeptide synthesis and releasing the polypeptide chain and the mRNA from the ribosome.

The structure of tRNA is often shown as a cloverleaf representation (FIG. 3A). Structural elements of a typical tRNA include an acceptor stem, a D-loop, an anticodon loop, a variable loop and a TΨC loop. Aminoacylation or charging of tRNA results in linking the carboxyl terminal of an amino acid to the 2'-(or 3'-) hydroxyl group of a terminal adenosine base via an ester linkage. This process can be accomplished either using enzymatic or chemical methods. Normally a particular tRNA is charged by only one specific native amino acid. This selective charging, termed here enzymatic aminoacylation, is accomplished by aminoacyl tRNA synthetases. A tRNA which selectively incorporates a tyrosine residue into the nascent polypeptide chain by recognizing the tyrosine UAC codon will be charged by tyrosine with a tyrosine-aminoacyl tRNA synthetase, while a tRNA designed to read the UGU codon will be charged by a cysteine-aminoacyl tRNA synthetase. These synthetases have evolved to be extremely accurate in charging a tRNA with the correct amino acid to maintain the fidelity of the translation process. Except in special cases where the non-native amino acid is very similar structurally to the native amino acid, it is necessary to use means other than enzymatic aminoacylation to charge a tRNA.

Molecular biologists routinely study the expression of proteins that are coded for by genes. A key step in research is to express the products of these genes either in intact cells or in cell-free extracts. Conventionally, molecular biologists use radioactively labeled amino acid residues such as $^{35}$S-methionine as a means of detecting newly synthesized proteins or so-called nascent proteins. These nascent proteins can normally be distinguished from the many other proteins present in a cell or a cell-free extract by first separating the proteins by the standard technique of gel electrophoresis and determining if the proteins contained in the gel possess the specific radioactively labeled amino acids. This method is simple and relies on gel electrophoresis, a widely available and practiced method. It does not require prior knowledge of the expressed protein and in general does not require the protein to have any special properties. In addition, the protein can exist in a denatured or unfolded form for detection by gel electrophoresis. Furthermore, more specialized techniques such as blotting to membranes and coupled enzymatic assays are not needed. Radioactive assays also have the advantage that the structure of the nascent protein is not altered or can be restored, and thus, proteins can be isolated in a functional form for subsequent biochemical and biophysical studies.

Radioactive methods suffer from many drawbacks related to the utilization of radioactively labeled amino acids. Handling radioactive compounds in the laboratory always involves a health risk and requires special laboratory safety procedures, facilities and detailed record keeping as well as special training of laboratory personnel. Disposal of radioactive waste is also of increasing concern both because of the potential risk to the public and the lack of radioactive waste disposal sites. In addition, the use of radioactive labeling is time consuming, in some cases requiring as much as several days for detection of the radioactive label. The long time needed for such experiments is a key consideration and can seriously impede research productivity. While faster methods of radioactive detection are available, they are expensive and often require complex image enhancement devices.

The use of radioactive labeled amino acids also does not allow for a simple and rapid means to monitor the production of nascent proteins inside a cell-free extract without prior separation of nascent from preexisting proteins. However, a separation step does not allow for the optimization of cell-free activity. Variables including the concentration of ions and metabolites and the temperature and the time of protein synthesis cannot be adjusted.

Radioactive labeling methods also do not provide a means of isolating nascent proteins in a form which can be further utilized. The presence of radioactivity compromises this utility for further biochemical or biophysical procedures in the laboratory and in animals. This is clear in the case of in vitro expression when proteins cannot be readily produced in vivo because the protein has properties which are toxic to the cell. A simple and convenient method for the detection and isolation of nascent proteins in a functional form could be important in the biomedical field if such proteins possessed diagnostic or therapeutic properties. Recent research has met with some success, but these methods have had numerous drawbacks.

Radioactive labeling methods also do not provide a simple and rapid means of detecting changes in the sequence of a nascent protein which can indicate the presence of potential disease causing mutations in the DNA which code for these proteins or fragments of these proteins. Current methods of analysis at the protein level rely on the use of gel electrophoresis and radioactive detection which are slow and not amenable to high throughput analysis and automation. Such mutations can also be detected by performing DNA sequence analysis on the gene coding for a particular protein or protein fragment. However, this requires large regions of DNA to be sequenced, which is time-consuming and expensive. The development of a general method which allows mutations to be detected at the nascent protein level is potentially very important for the biomedical field.

Radioactive labeling methods also do not provide a simple and rapid means of studying the interaction of nascent proteins with other molecules including compounds which might be have importance as potential drugs. If such an approach were available, it could be extremely useful for screening large numbers of compounds against the nascent proteins coded for by specific genes, even in cases where the genes or protein has not yet been characterized. In current technology, which is based on affinity electrophoresis for screening of potential drug candidates, both in natural samples and synthetic libraries, proteins must first be labeled uniformly with a specific marker which often requires specialized techniques including isolation of the protein and the design of special ligand markers or protein engineering.

Special tRNAs, such as tRNAs which have suppressor properties, suppressor tRNAs, have been used in the process of site-directed non-native amino acid replacement (SNAAR) (C. Noren et al., Science 244:182–188, 1989). In SNAAR, a unique codon is required on the mRNA and the suppressor tRNA, acting to target a non-native amino acid to a unique site during the protein synthesis (PCT WO90/05785). However, the suppressor tRNA must not be recognizable by the aminoacyl tRNA synthetases present in the protein translation system (Bain et al., Biochemistry 30:5411–21, 1991). Furthermore, site-specific incorporation of non-native amino acids is not suitable in general for detection of nascent proteins in a cellular or cell-free protein synthesis system due to the necessity of incorporating nonsense codons into the coding regions of the template DNA or the mRNA.

Products of protein synthesis may also be detected by using antibody based assays. This method is of limited use because it requires that the protein be folded into a native form and also for antibodies to have been previously produced against the nascent protein or a known protein which is fused to the unknown nascent protein. Such procedures are time consuming and again require identification and characterization of the protein. In addition, the production of antibodies and amino acid sequencing both require a high level of protein purity.

In certain cases, a non-native amino acid can be formed after the tRNA molecule is aminoacylated using chemical reactions which specifically modify the native amino acid and do not significantly alter the functional activity of the aminoacylated tRNA (Promega Technical Bulletin No. 182; tRNA$^{nscend}$TM: Non-radioactive Translation Detection System, September 1993). These reactions are referred to as post-aminoacylation modifications. For example, the ∈-amino group of the lysine linked to its cognate tRNA (tRNA$^{LYS}$), could be modified with an amine specific photoaffinity label (U. C. Krieg et al., Proc. Natl. Acad. Sci. USA 83:8604–08, 1986). These types of post-aminoacylation modifications, although useful, do not provide a general means of incorporating non-native amino acids into the nascent proteins. The disadvantage is that only those non-native amino acids that are derivatives of normal amino acids can be incorporated and only a few amino acid residues have side chains amenable to chemical modification. More often, post-aminoacylation modifications can result in the tRNA being altered and produce a non-specific modification of the α-amino group of the amino acid (e.g. in addition to the ∈-amino group) linked to the tRNA. This factor can lower the efficiency of incorporation of the non-native amino acid linked to the tRNA. Non-specific, post-aminoacylation modifications of tRNA structure could also compromise its participation in protein synthesis. Incomplete chain formation could also occur when the α-amino group of the amino acid is modified.

In certain other cases, a nascent protein can be detected because of its special and unique properties such as specific enzymatic activity, absorption or fluorescence. This approach is of limited use since most proteins do not have special properties with which they can be easily detected. In many cases, however, the expressed protein may not have been previously characterized or even identified, and thus, its characteristic properties are unknown.

SUMMARY OF THE INVENTION

The present invention overcomes the problems and disadvantages associated with current strategies and designs and provides methods for the labeling, detection, quantitation, analysis and isolation of nascent proteins produced in a cell-free or cellular translation system without the use of radioactive amino acids or other radioactive labels. One embodiment of the invention is directed to methods for detecting nascent proteins translated in a translation system. A tRNA molecule is aminoacylated with a fluorescent marker to create a misaminoacylated tRNA. The misaminoacylated, or charged, tRNA can be formed by chemical, enzymatic or partly chemical and partly enzymatic techniques which place a fluorescent marker into a position on the tRNA molecule from which it can be transferred into a growing peptide chain. Markers may comprise native or non-native amino acids with fluorescent moeities, amino acid analogs or derivatives with fluorescent moities, detectable labels, coupling agents or combinations of these components with fluoresecent moieties. The misaminoacylated tRNA is introduced to the translation system such as a cell-free extract, the system is incubated and the fluorescent marker incorporated into nascent proteins.

It is not intended that the present invention be limited to the nature of the particular fluorescent moeity. A variety of fluorescent compounds are contemplated, including fluorescent compounds that have been derivatized (e.g. with NHS) to be soluble (e.g. NHS-derivatives of coumarin). Nonetheless, compared to many other fluorophores with high quantum yields, several BODIPY compounds and reagents have been empirically found to have the additional important and unusual property that they can be incorporated with high efficiency into nascent proteins for both UV and visible excited fluorescence detection. These methods utilitzing fluorescent moeities may be used to detect, isolate and quantitate such nascent proteins as recombinant gene products, gene fusion products, truncated proteins caused by mutations in human genes, enzymes, cytokines, hormones, immunogenic proteins, human proteins, carbohydrate and lipid binding proteins, nucleic acid binding proteins, viral proteins, bacterial proteins, parasitic proteins and fragments and combinations thereof.

Another embodiment of the invention is directed to methods for labeling nascent proteins at their amino terminus. An initiator tRNA molecule, such as methionine-initiator tRNA or formylmethionine-initiator tRNA is misaminoacylated with a fluorescent moeity (e.g. a BODIPY moiety) and introduced to a translation system. The system is incubated and marker is incorporate at the amino terminus of the nascent proteins. Nascent proteins containing marker can be detected, isolated and quantitated. Markers or parts of markers may be cleaved from the nascent proteins which substantially retain their native configuration and are functionally active.

Thus, the present invention contemplates compositions, methods and systems. In terms of compositions, the present invention specifically contemplates a tRNA molecule misaminoacylated with a BODIPY marker.

In one embodiment, the present invention contemplates a method, comprising: a) providing a tRNA molecule and a BODIPY marker; and b) aminoacylating said tRNA molecule with said BODIPY marker to create a misaminoacylated tRNA. In a particular embodiment, the method further comprises c) introducing said misaminoacylated tRNA into a translation system under conditions such that said marker is incorporated into a nascent protein. In yet another embodiment, the method further comprises d) detecting said nascent protein containing said marker. In still another embodiment, the method further comprises e) isolating said detected nascent protein.

The present invention contemplates aminoacylation of the tRNA molecule by chemical or enzymatic misaminoacylation. The present invention also contemplates embodiments wherein two or more different misaminoacylated tRNAs are introduced into the translation system. In a preferred embodiment, the nascent protein detected (by virtue of the incorporated marker) is functionally active.

It is not intended that the present invention be limited by the particular nature of the nascent protein. In one embodiment, the present invention contemplates a method for detecting nascent proteins which are conjugated to the mRNA message which codes for all or part of the nascent protein. In general, a variety of modifications of the nascent protein are envisioned including post-translational modifications, proteolysis, attachment of an oligonucleotide through a puromycin linker to the C-terminus of the protein, and interaction of the nascent protein with other components of the translation system including those which are added exogenously.

It is not intended that the present invention be limited by the particular nature of the tRNA molecule. In one embodiment, the tRNA molecule is an initiator tRNA molecule. In another embodiment, the tRNA molecule is a suppressor tRNA molecule.

The present invention also contemplates kits. In one embodiment, the kit comprises a) a first containing means (e.g. tubes, vials, etc) containing at least one component of a protein synthesis system; and b) a second containing means containing a misaminoacylated tRNA, wherein said tRNA is misaminoacylated with a BODIPY marker. Such kits may include initiator tRNA and/or suppressor tRNA. Importantly, the kit is not limited to the particular components of said protein synthesis system; a variety of components are contemplated (e.g. ribosomes).

Another embodiment of the invention is directed to methods for detecting nascent proteins translated in a translation system. A tRNA molecule is aminoacylated with one component of a binary marker system. The misaminoacylated, or charged, tRNA can be formed by chemical, enzymatic or partly chemical and partly enzymatic techniques which place a component of a binary marker system into a position on the tRNA molecule from which it can be transferred into a growing peptide chain. The component of the binary marker system may comprise native or non-native amino acids, amino acid analogs or derivatives, detectable labels, coupling agents or combinations of these components. The misaminoacylated tRNA is introduced to the translation system such as a cell-free extract, the system is incubated and the marker incorporated into nascent proteins. The second component of the binary marker system is then introduced making the first component incorporated into the nascent protein specifically detectable. These methods may be used to detect, isolate and quantitate such nascent proteins as recombinant gene products, gene fusion products, enzymes, cytokines, hormones, immunogenic proteins, human proteins, carbohydrate and lipid binding proteins, nucleic acid binding proteins, viral proteins, bacterial proteins, parasitic proteins and fragments and combinations thereof.

It is not intended that the present invention be limited to a particular translation system. In one embodiment, a cell-free translation system is selected from the group consisting of *Escherichia coli* lysates, wheat germ extracts, insect cell lysates, rabbit reticulocyte lysates, frog oocyte lysates, dog pancreatic lysates, human cell lysates, mixtures of purified or semi-purified translation factors and combinations thereof. It is also not intended that the present invention be limited to the particular reaction conditions employed. However, typcially the cell-free translation system is incubated at a temperature of between about 25° C. to about 45° C. The present invention contemplates both continuous flow systems or dialysis systems.

Another embodiment of the invention is directed to methods for the detection of nascent proteins translated in a cellular or cell-free translation system using non-radioactive markers which have detectable electromagnetic spectral properties. As before, a non-radioactive marker is misaminoacylated to a tRNA molecule and the misaminoacylated tRNA is added to the translation system. The system is incubated to incorporate marker into the nascent proteins. Nascent proteins containing marker can be detected from the specific electromagnetic spectral property of the marker. Nascent proteins can also be isolated by taking advantage of unique properties of these markers or by conventional means such as electrophoresis, gel filtration, high-pressure or fast-pressure liquid chromatography, affinity chromatography, ion exchange chromatography, chemical extraction, magnetic bead separation, precipitation or combinations of these techniques.

Another embodiment of the invention is directed to the synthesis of nascent proteins containing markers which have reporter properties when the reporter is brought into contact with a second agent. Reporter markers are chemical moieties which have detectable electromagnetic spectral properties when incorporated into peptides and whose spectral properties can be distinguished from unincorporated markers and markers attached to tRNA molecules. As before, tRNA molecules are misaminoacylated, this time using reported markers. The misaminoacylated tRNAs are added to a translation system and incubated to incorporate marker into the peptide. Reporter markers can be used to follow the process of protein translation and to detect and quantitate nascent proteins without prior isolation from other components of the protein synthesizing system.

Another embodiment of the invention is directed to compositions comprised of nascent proteins translated in the presence of markers, isolated and, if necessary, purified in a cellular or cell-free translation system. Compositions may further comprise a pharmaceutically acceptable carrier and be utilized as an immunologically active composition such as a vaccine, or as a pharmaceutically active composition such as a drug, for use in humans and other mammals.

Another embodiment of the invention is directed to methods for detecting nascent proteins translated in a translation system by using mass spectrometry. A non-radioactive marker of known mass is misaminoacylated to a tRNA molecule and the misaminoacylated tRNA is added to the translation system. The system is incubated to incorporate the mass marker into the nascent proteins. The mass spectrum of the translation system is then measured. The presence of the nascent protein can be directly detected by identifying peaks in the mass spectrum of the protein synthesis system which correspond to the mass of the unmodified protein and a second band at a higher mass which corresponds to the mass of the nascent protein plus the modified amino acid containing the mass of the marker. When the mass marker is photocleavable, the assignment of the second band to a nascent protein containing the mass marker can be verified by removing the marker with light.

Another embodiment of the invention is directed to methods for detecting nascent proteins with mutations which are translated in a translation system. RNA or DNA coding for the protein which may contain a possible mutation is added to the translation system. The system is incubated to synthesize the nascent proteins. The nascent protein is then separated from the translation system using an affinity marker located at or close to the N-terminal end of the protein. The protein is then analyzed for the presence of a detectable marker located at or close to the N-terminal of the protein (N-terminal marker). A separate measurement is then made on a sequence dependent detectable marker located at or close to the C-terminal end of the protein (C-terminal marker). A comparison is then made of the level of incorporation of the N-terminal and C-terminal markers in the nascent protein. It is not intended that the present invention be limited by the nature of the N- and C-terminal markers, or the type of affinity marker utilized. A variety of markers are contemplated. In one embodiment, the affinity marker comprises an epitope recognized by an antibody or other binding molecule. In one embodiment, the N-terminal marker comprises a fluorescent marker (e.g. a BODIPY marker), while the C-terminal marker comprises a metal binding region (e.g. His tag).

The present invention contemplates a variety of methods wherein the three markers (e.g. the N- and C-terminal markers and the affinity markers) are introduced into a nascent protein. In one embodiment, the method comprises: a) providing i) a misaminoacylated initiator tRNA molecule which only recognizes the first AUG codon that serves to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker, said C-terminal marker and (in some embodiments) said affinity marker. In one embodiment, the method further comprises, after step b), isolating said nascent protein.

In another embodiment, the method comprises: a) providing i) a misaminoacylated initiator tRNA molecule which only recognizes the first AUG codon that serves to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker at the N-terminus of said protein, a C-terminal marker, and (in some embodiments) said affinity marker adjacent to said first marker. In one embodiment, the method further comprises, after step b), isolating said nascent protein.

In yet another embodiment, the method comprises: a) providing i) a misaminoacylated tRNA molecule which only recognizes the first codon designed to serve to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker, said C-terminal marker and (in some embodiments) said affinity marker. In one embodiment, the method further comprises, after step b), isolating said nascent protein.

In still another embodiment, the method comprises: a) providing i) a misaminoacylated tRNA molecule which only recognizes the first codon designed to serve to initiate protein synthesis, said misaminoacylated initiator tRNA molecule comprising a first marker, and ii) a nucleic acid template encoding a protein, said protein comprising a C-terminal marker and (in some embodiments) an affinity marker; b) introducing said misaminoacylated initiator tRNA to a translation system comprising said template under conditions such that a nascent protein is generated, said protein comprising said first marker at the N-terminus of said protein, a C-terminal marker, and (in some embodiments) said affinity marker adjacent to said first marker. In one embodiment, the method further comprises, after step b), isolating said nascent protein.

The present invention also contemplates embodiments where only two markers are employed (e.g. a marker at the N-terminus and a marker at the C-terminus). In one embodiment, the nascent protein is non-specifically bound to a solid support (e.g. beads, microwells, strips, etc.), rather than by the specific interaction of an affinity marker. In this context, "non-specific" binding is meant to indicate that binding is not driven by the uniqueness of the sequence of the nascent protein. Instead, binding can be by charge interactions. In one embodiment, the present invention contemplates that the solid support is modified (e.g. functionalized to change the charge of the surface) in order to capture the nascent protein on the surface of the solid support. In one embodiment, the solid support is poly-L-lysine coated. In yet another embodiment, the solid support is nitrocellulose (e.g. strips, nicrocellulose containing microwells, etc.). Regardless of the particular nature of the solid support, the present invention contemplates that the nascent protein containing the two markers is captured under conditions that permit the ready detection of the markers.

In both the two marker and three marker embodiments described above, the present invention contemplates that one or more of the markers will be introduced into the nucleic acid template by primer extension or PCR. In one embodiment, the present invention contemplates a primer comprising (on or near the 5'-end) a promoter, a ribosome binding site ("RBS"), and a start codon (e.g. ATG), along with a region of complementarity to the template. In another embodiment, the present invention contemplates a primer comprising (on or near the 5'-end) a promoter, a ribosome binding site ("RBS"), a start codon (e.g. ATG), a region encoding an affinity marker, and a region of complementarity to the template. It is not intended that the present invention be limited by the length of the region of complementarity; preferably, the region is greater than 8 bases in length, more preferably greater than 15 bases in length, and still more preferably greater than 20 bases in length.

It is also not intended that the present invention be limited by the ribosome binding site. In one embodiment, the present invention contemplates primers comprising the Kozak sequence, a string of non-random nucleotides (consensus sequence 5'-GCCA/GCCATGG-3') SEQ ID NO:1 which are present before the translation initiating first ATG in majority of the mRNAs which are transcribed and translated in an eukarytic cells. See M. Kozak, *Cell* 44:283–292 (1986). In another embodiment, the present invention contemplates a primer comprising the the prokaryotic mRNA ribosome binding site, which usually contains part or all of a polypurine domain UAAGGAGGU SEQ ID NO:2 known as the Shine-Dalgarno (SD) sequence found just 5' to the translation initiation codon: mRNA 5'-UAAGGAGGU-$N_{5-10}$-AUG SEQ ID NO:3.

For PCR, two primers are used. In one embodiment, the present invention contemplates as the forward primer a primer comprising (on or near the 5'-end) a promoter, a ribosome binding site ("RBS"), and a start codon (e.g. ATG), along with a region of complementarity to the template. In another embodiment, the present invention contemplates as the forward primer a primer comprising (on or near the 5'-end) a promoter, a ribosome binding site ("RBS"), a start codon (e.g. ATG), a region encoding an affinity marker, and a region of complementarity to the template. The present invention contemplates that the reverse primer, in one embodiment, comprises (at or near the 5'-end) one or more stop condons and a region encoding a C-terminus marker (such as a HIS-tag).

Another embodiment of the invention is directed to methods for detecting by electrophoresis (e.g. capillary electrophoresis) the interaction of molecules with nascent proteins which are translated in a translation system. A tRNA misaminoacylated with a detectable marker is added to the protein synthesis system. The system is incubated to incorporate the detectable marker into the nascent proteins. One or more specific molecules are then combined with the nascent proteins (either before or after isolation) to form a mixture containing nascent proteins/molecule conjugates. Aliquots of the mixture are then sujected to capillarly electrophoresis. Nascent proteins/molecule conjugates are identified by detecting changes in the electrophoretic mobility of nascent proteins with incorporated markers.

Other embodiments and advantages of the invention are set forth, in part, in the description which follows and, in part, will be obvious from this description, or may be learned from the practice of the invention.

Definitions

To facilitate understanding of the invention, a number of terms are defined below.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may have 5' and 3' ends.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

As used herein, the terms "hybridize" and "hybridization" refers to the annealing of a complementary sequence to the target nucleic acid. The ability of two polymers of nucleic acid containing complementary sequences to find each other and anneal through base pairing interaction is a well-recognized phenomenon. Marmur and Lane, Proc. Natl. Acad. Sci. USA 46:453 (1960) and Doty et al., Proc. Natl. Acad. Sci. USA 46:461 (1960). The terms "annealed" and "hybridized" are used interchangeably throughout, and are intended to encompass any specific and reproducible interaction between an oligonucleotide and a target nucleic acid, including binding of regions having only partial complementarity.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

The stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like. As noted above, an oligonucleotide primer need not be perfectly complementary to a target or template sequence. A primer need only have a sufficient interaction with the template that it can be extended by template-dependent synthesis.

As used herein, the term "poly-histidine tract" or (HIS-tag) refers to the presence of two to ten histidine residues at either the amino- or carboxy-terminus of a nascent protein. A poly-histidine tract of six to ten residues is preferred. The poly-histidine tract is also defined functionally as being a number of consecutive histidine residues added to the protein of interest which allows the affinity purification of the resulting protein on a nickel-chelate column, or the indentification of a protein terminus through the interaction with another molecule (e.g. an antibody reactive with the HIS-tag).

DESCRIPTIONS OF THE DRAWINGS

FIG. 1(A) shows the structure of an amino acid. FIG. 1(B) shows the structure of a peptide SEQ ID NO:15.

FIG. 2 SEQ ID NO:16 & 18 provides a description of the molecular steps that occur during protein synthesis in a cellular or cell-free system.

Figure 7:
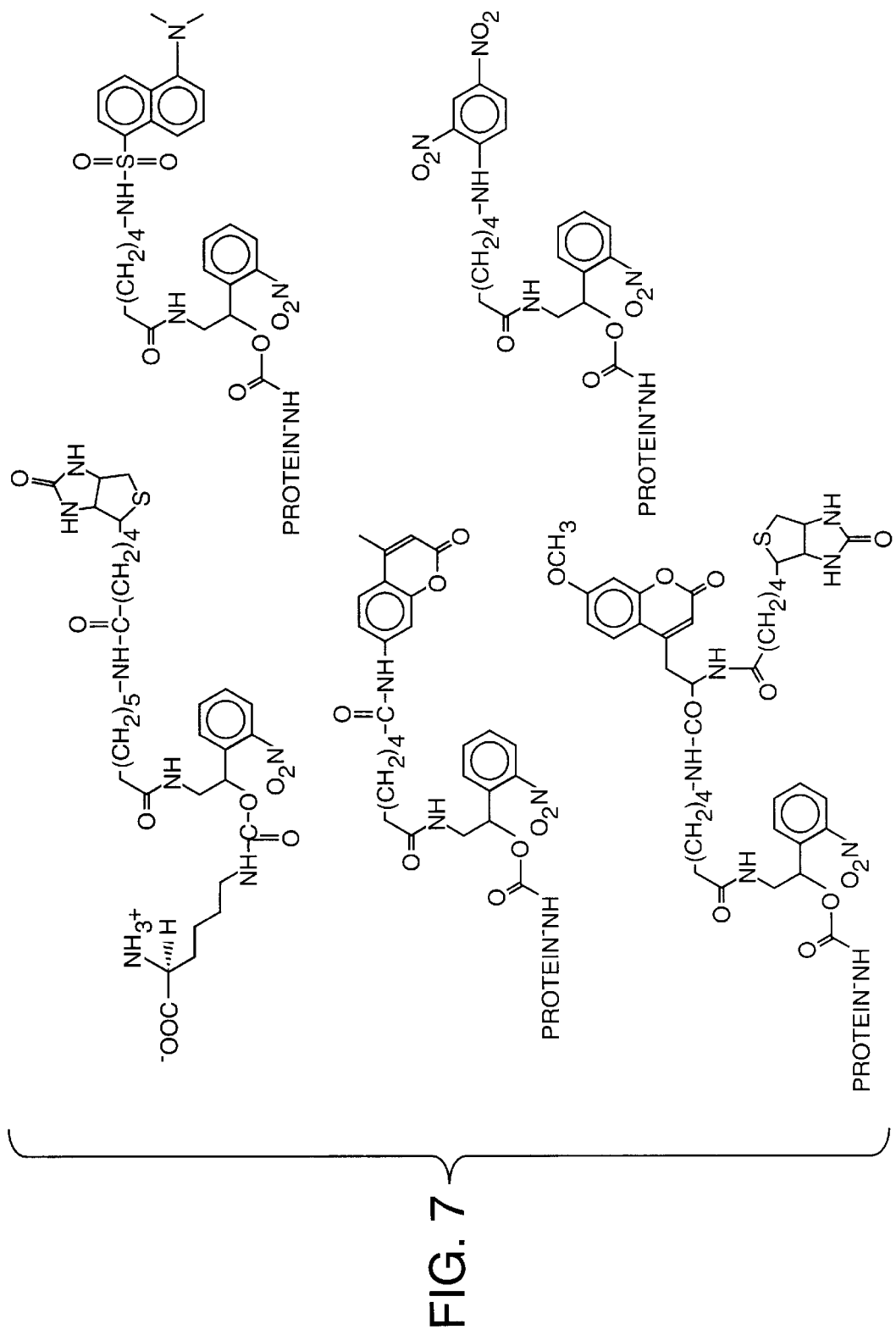

FIG. 7 provides examples of photocleavable markers.

Figure 8A:
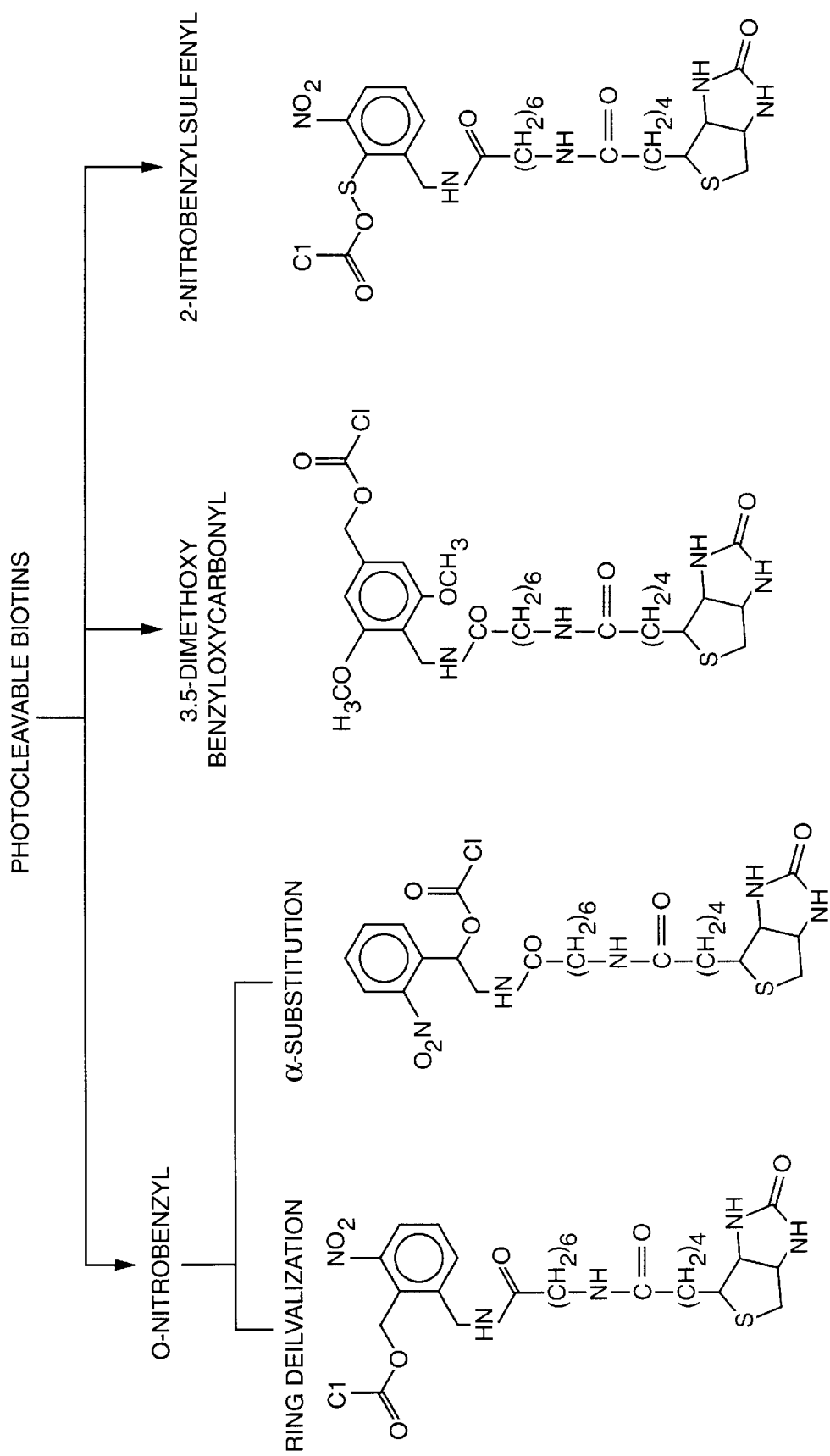
Figure 8B:
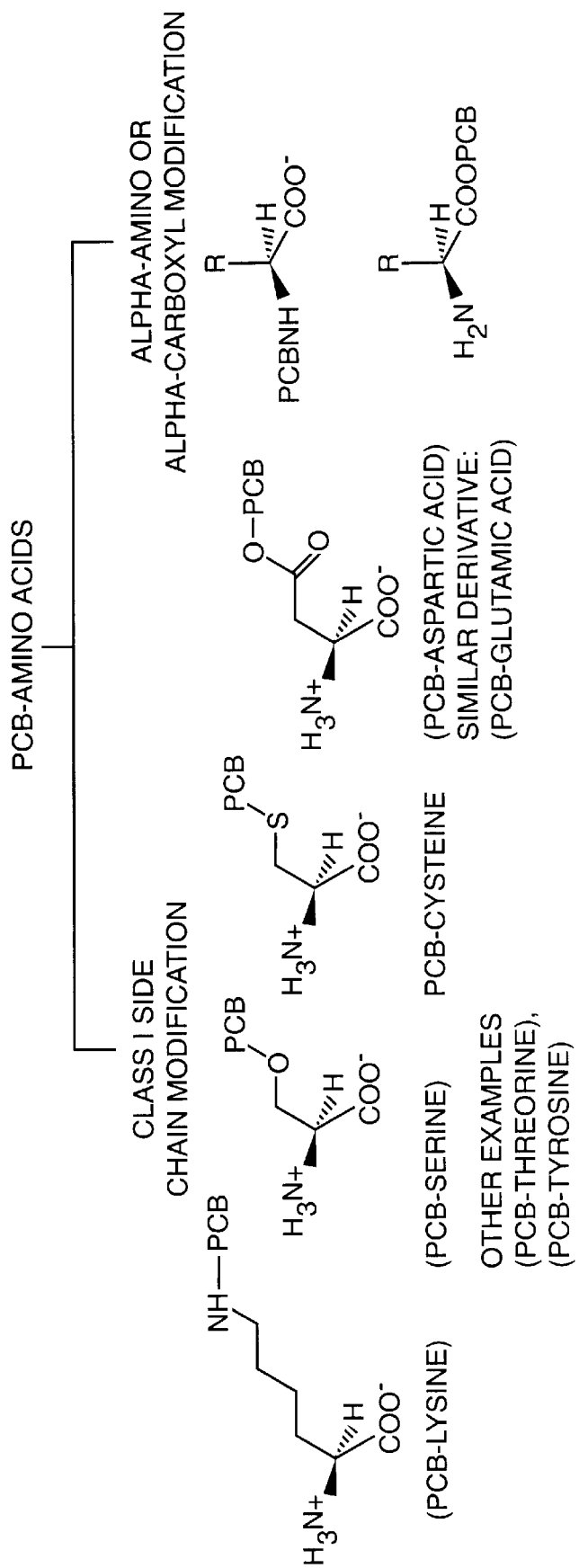

FIG. 8(A) shows chemical variations of PCB, and FIG. 8(B) depicts possible amino acid linkages.

Figure 9:
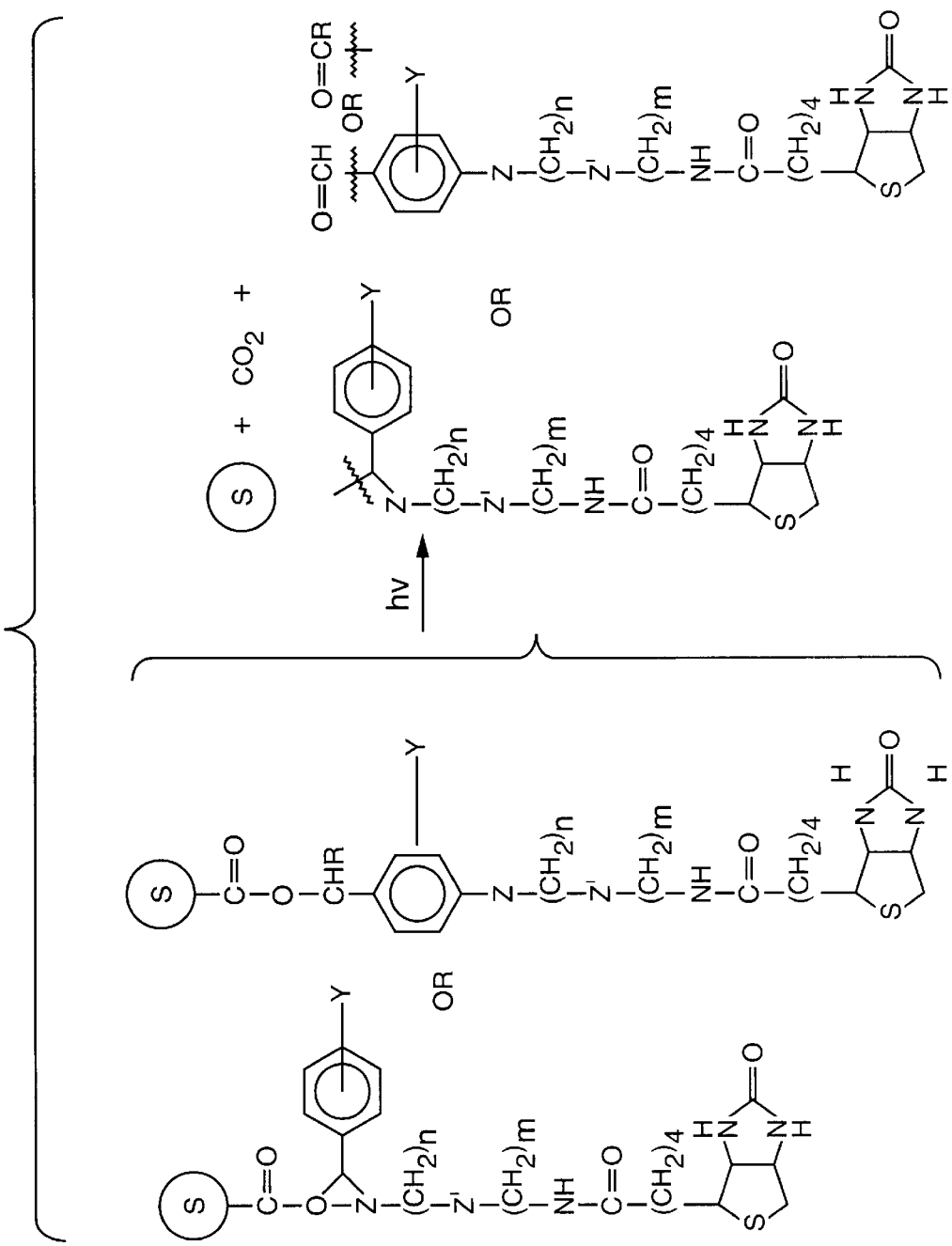

FIG. 9 shows the photolysis of PCB.

Figure 10:
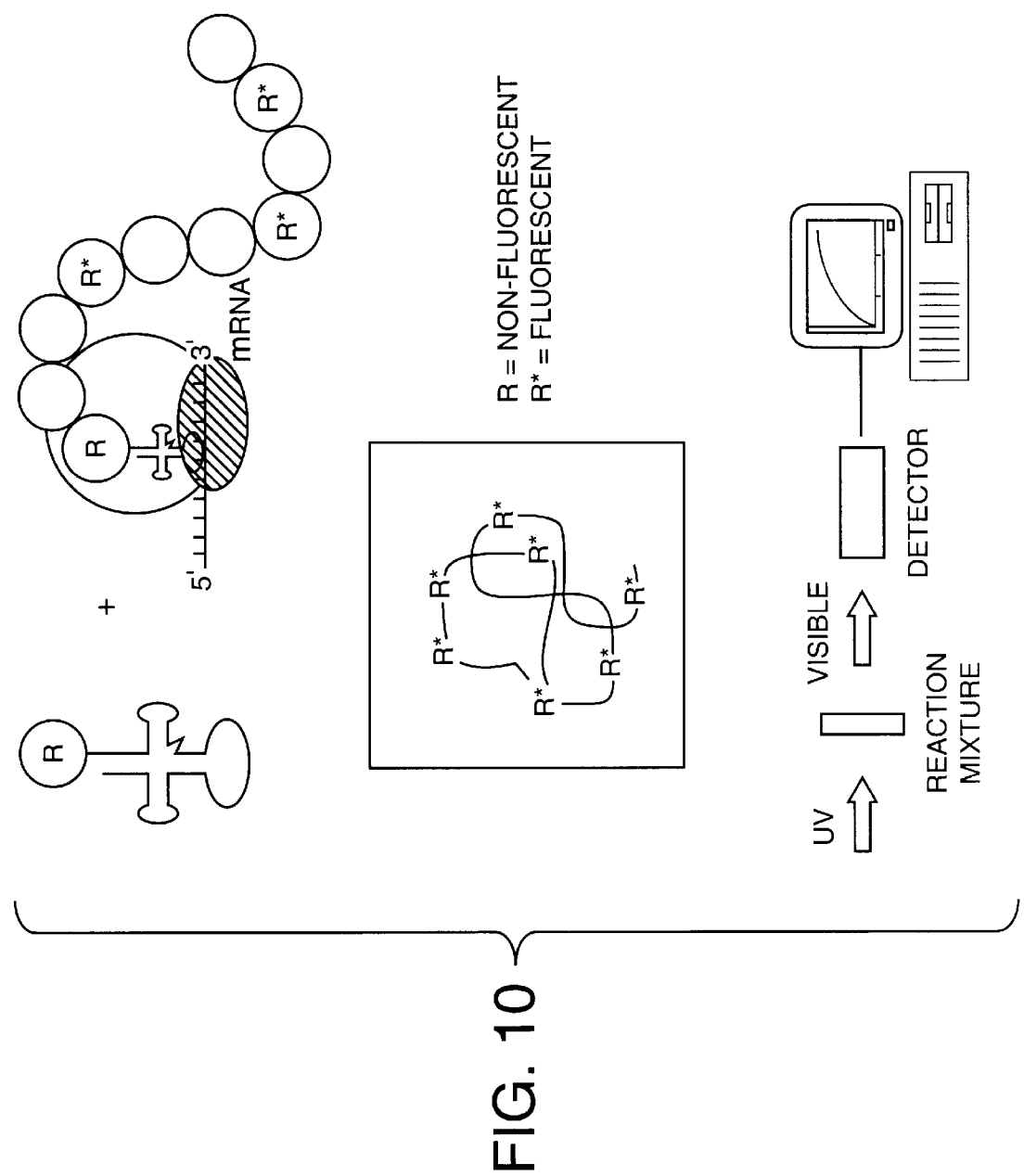

FIG. 10 is a schematic representation of the method for monitoring the production of nascent proteins in a cell-free protein expression systems without separating the proteins.

Figure 11:
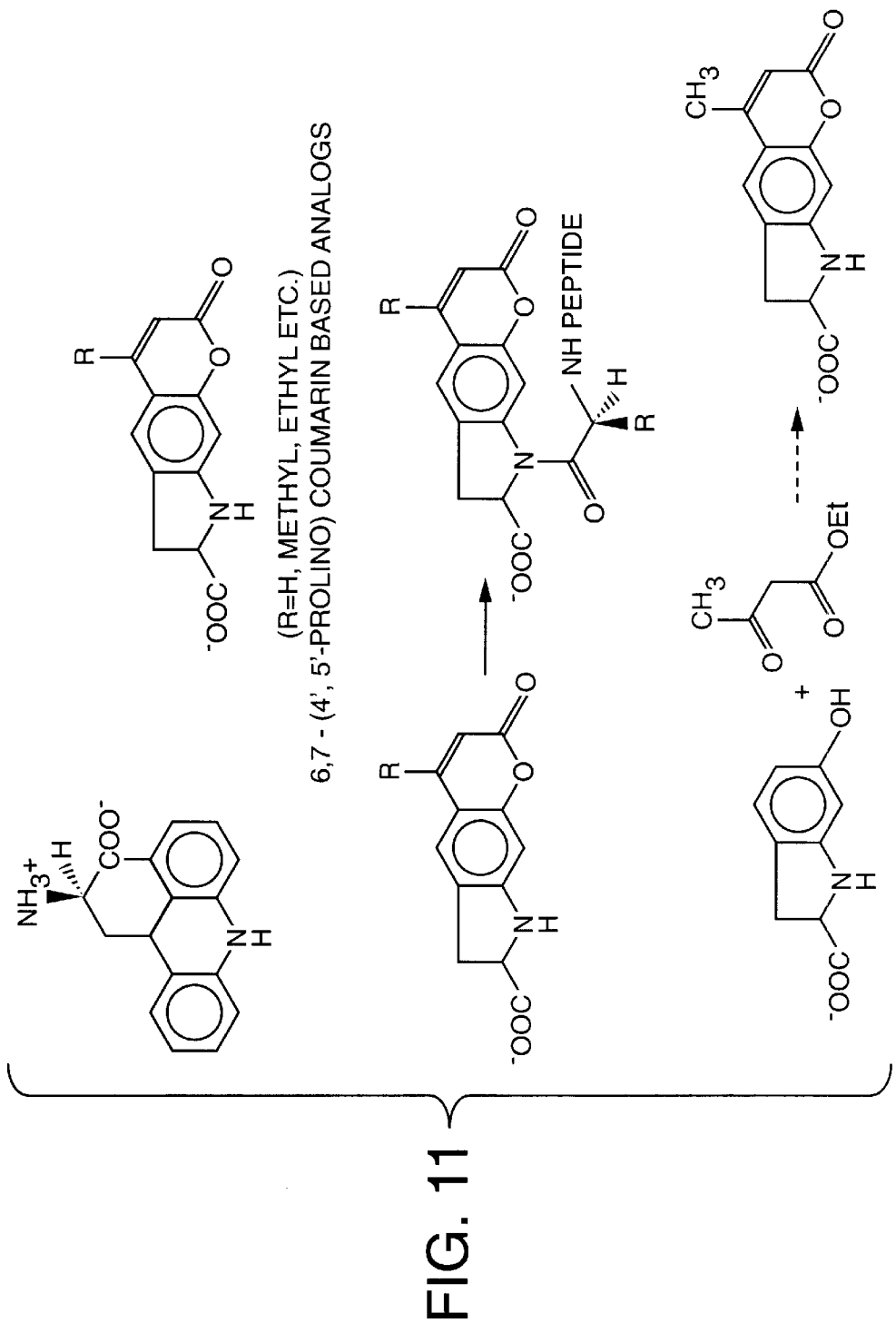

FIG. 11 provides examples of non-native amino acids with reporter properties, illustrates participation of a reporter in protein synthesis, and illustrates synthesis of a reporter.

Figure 12:
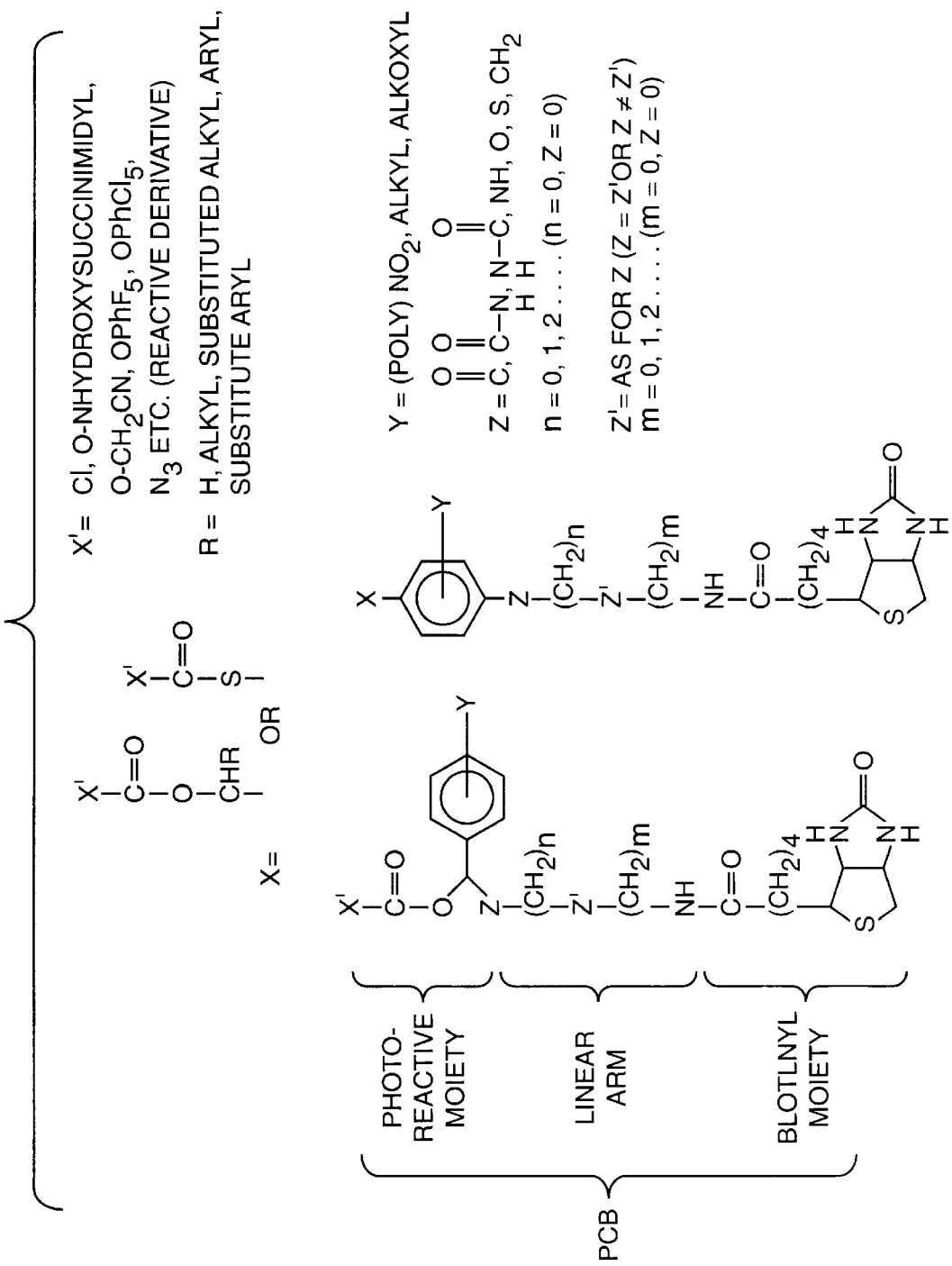

FIG. 12 shows structural components of photocleavable biotin.

Figure 13:
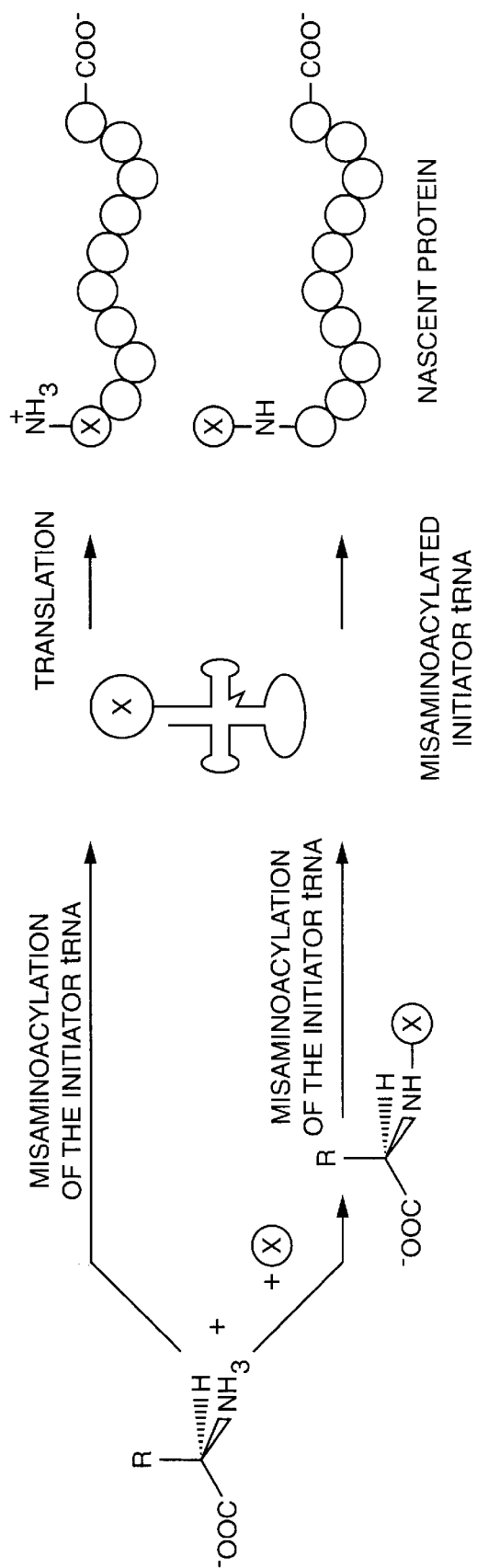

FIG. 13 is a schematic representation of the method for introduction of markers at the N-termini of nascent proteins.

Figure 14:
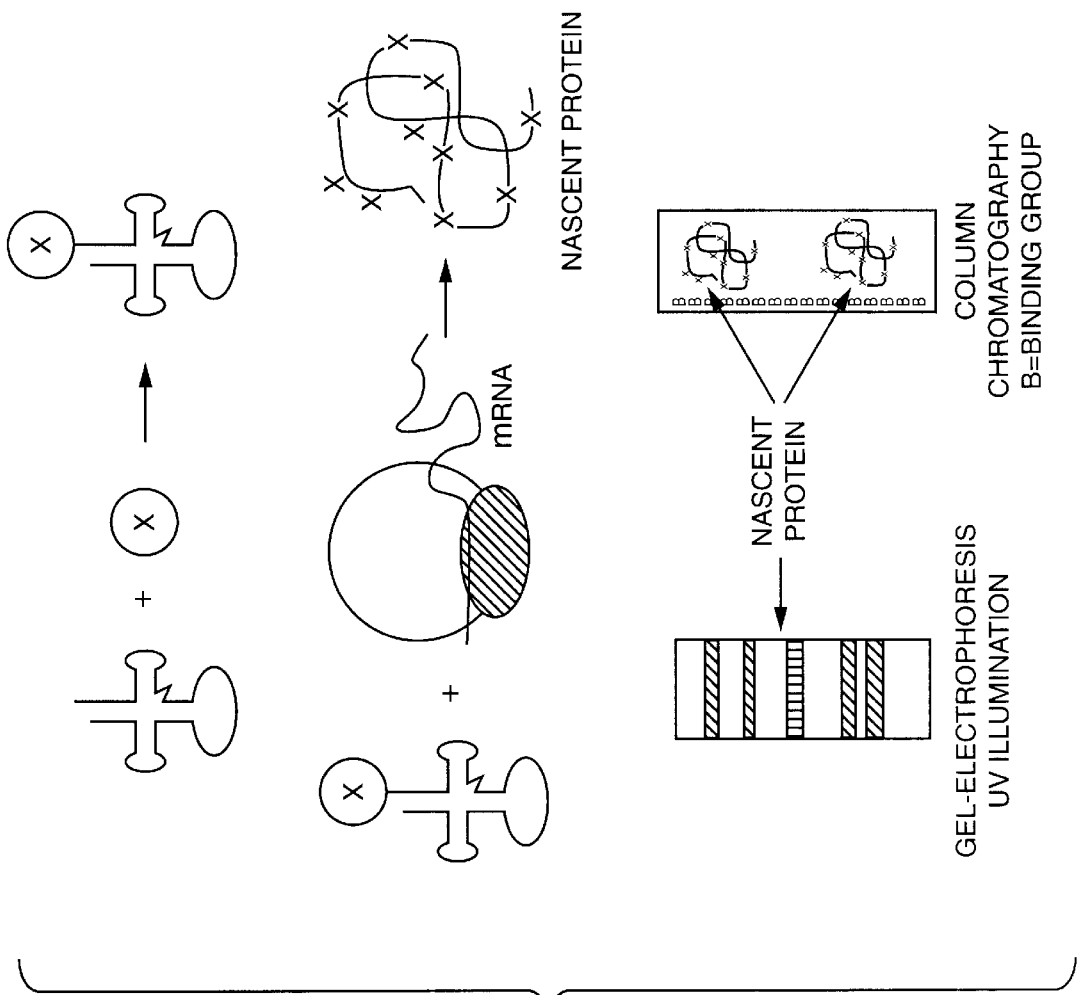

FIG. 14 provides a description of the method of detection and isolation of marker in nascent proteins.

Figure 15:
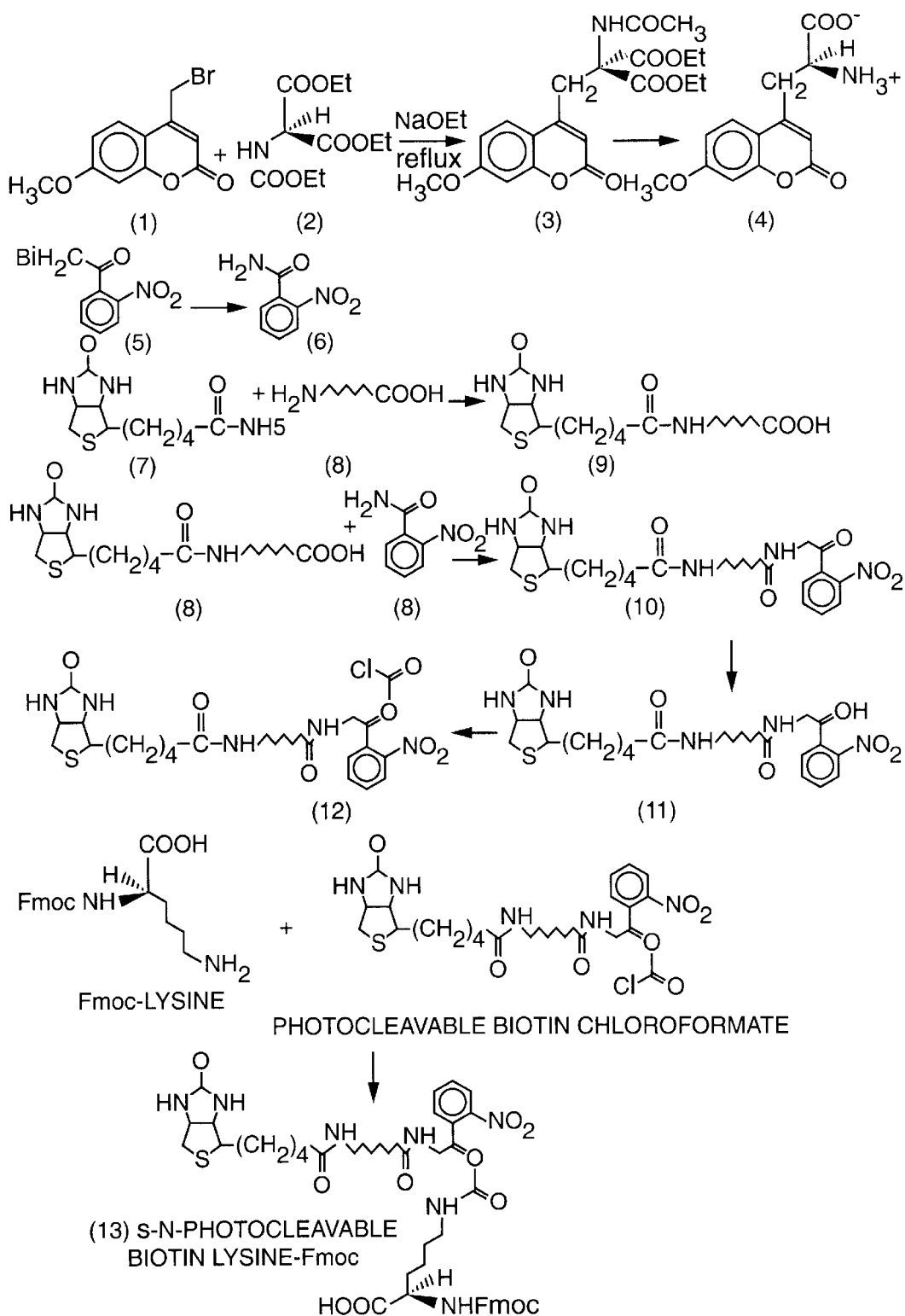

FIG. 15 shows the steps in one embodiment for the synthesis of PCB-lysine.

Figure 16:
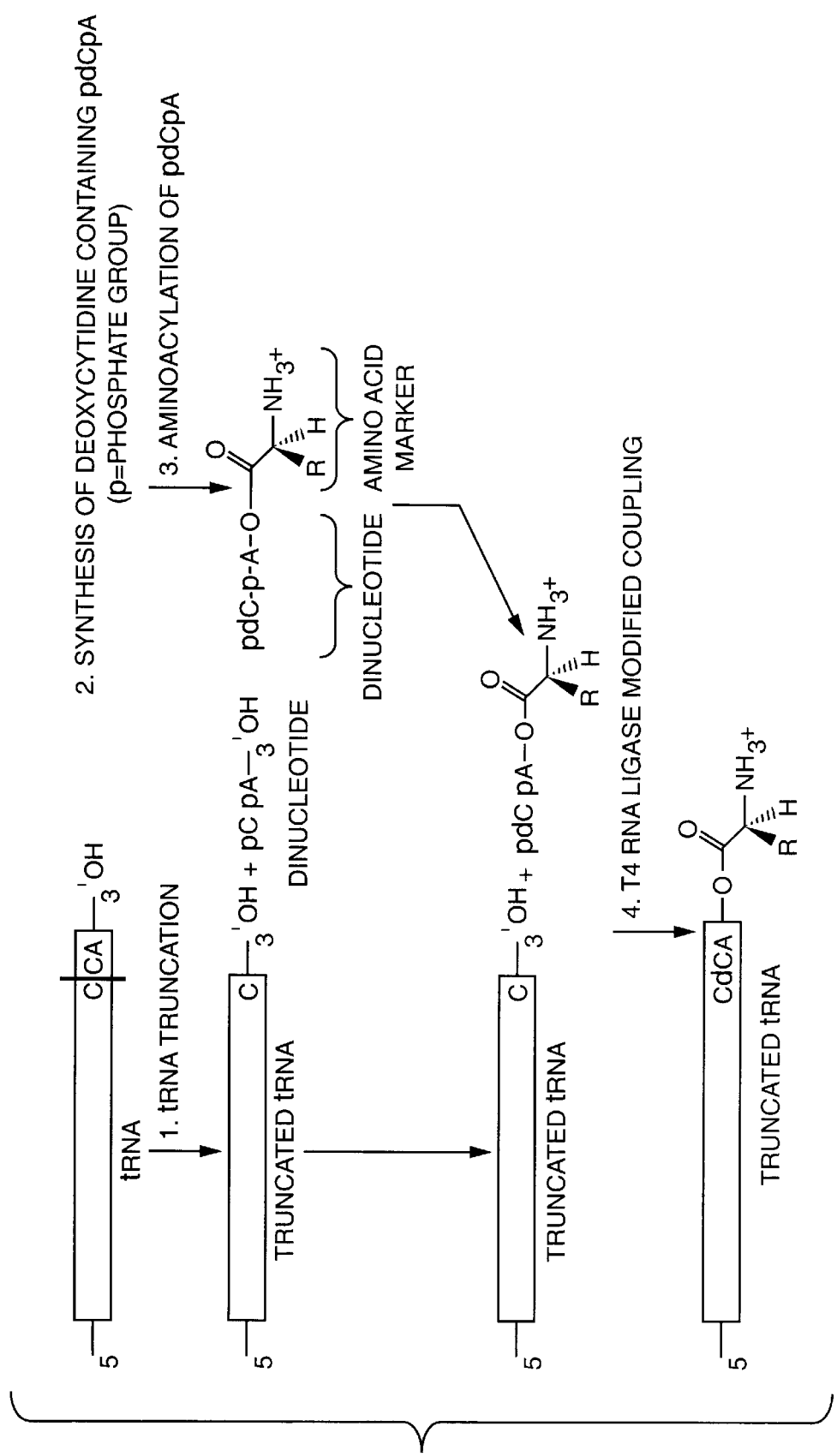

FIG. 16 provides an experimental strategy for the misaminoacylation of tRNA.

Figure 17:
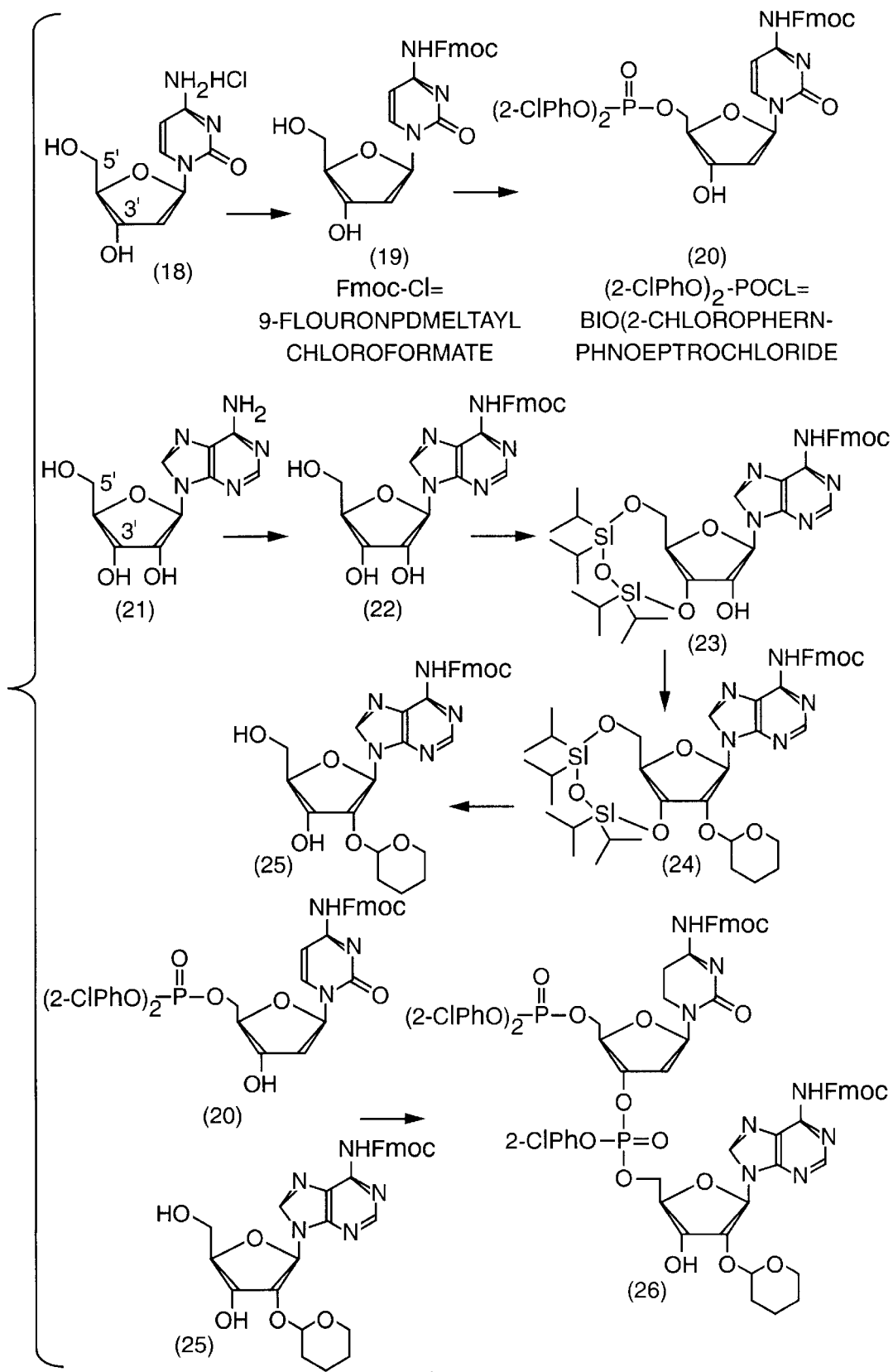

FIG. 17 illustrates dinucleotide synthesis including (i) deoxycytidine protection, (ii) adenosine protection, and (iii) dinucleotide synthesis.

Figure 18:
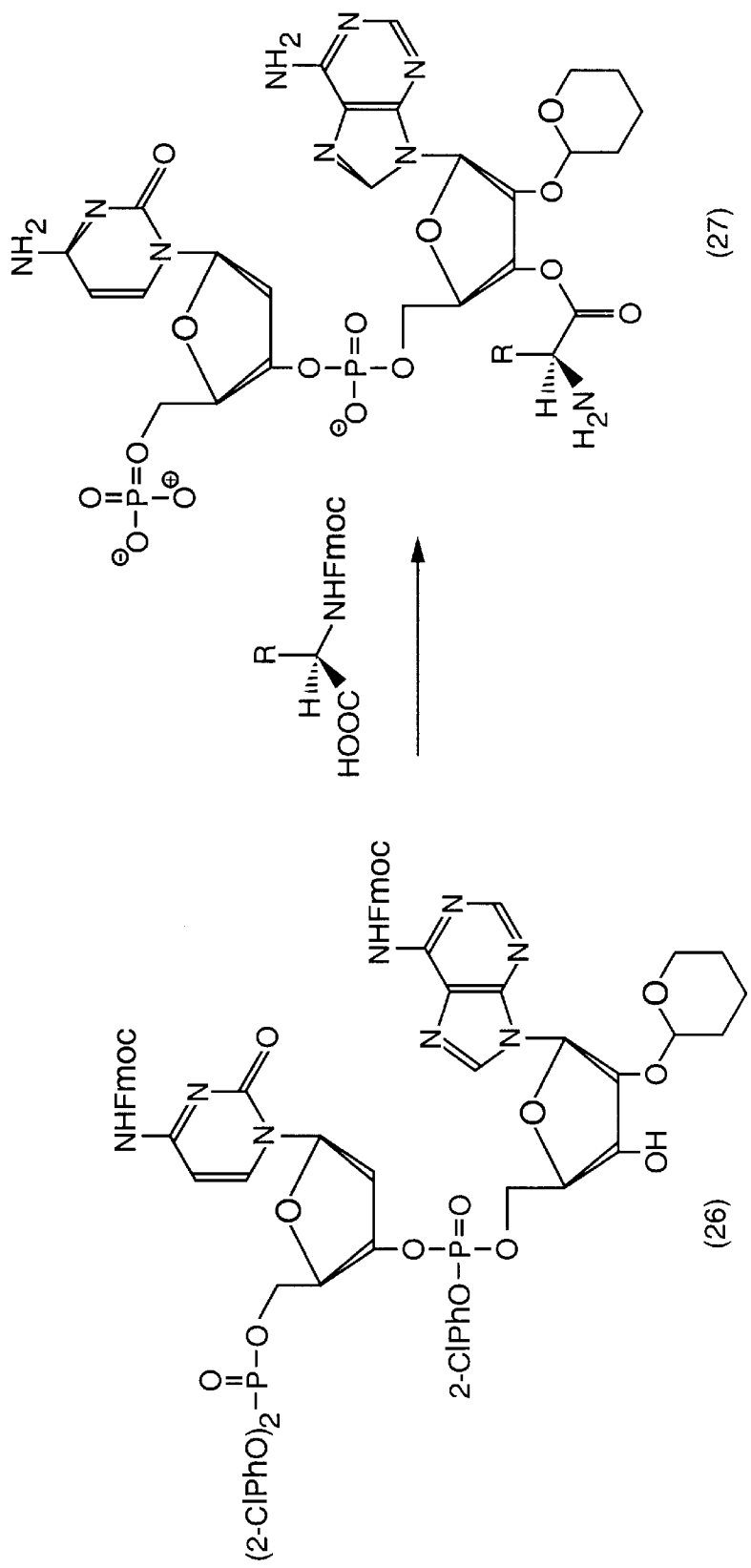

FIG. 18 depicts aminoacylation of a dinucleotide using marker amino acids.

Figure 19:
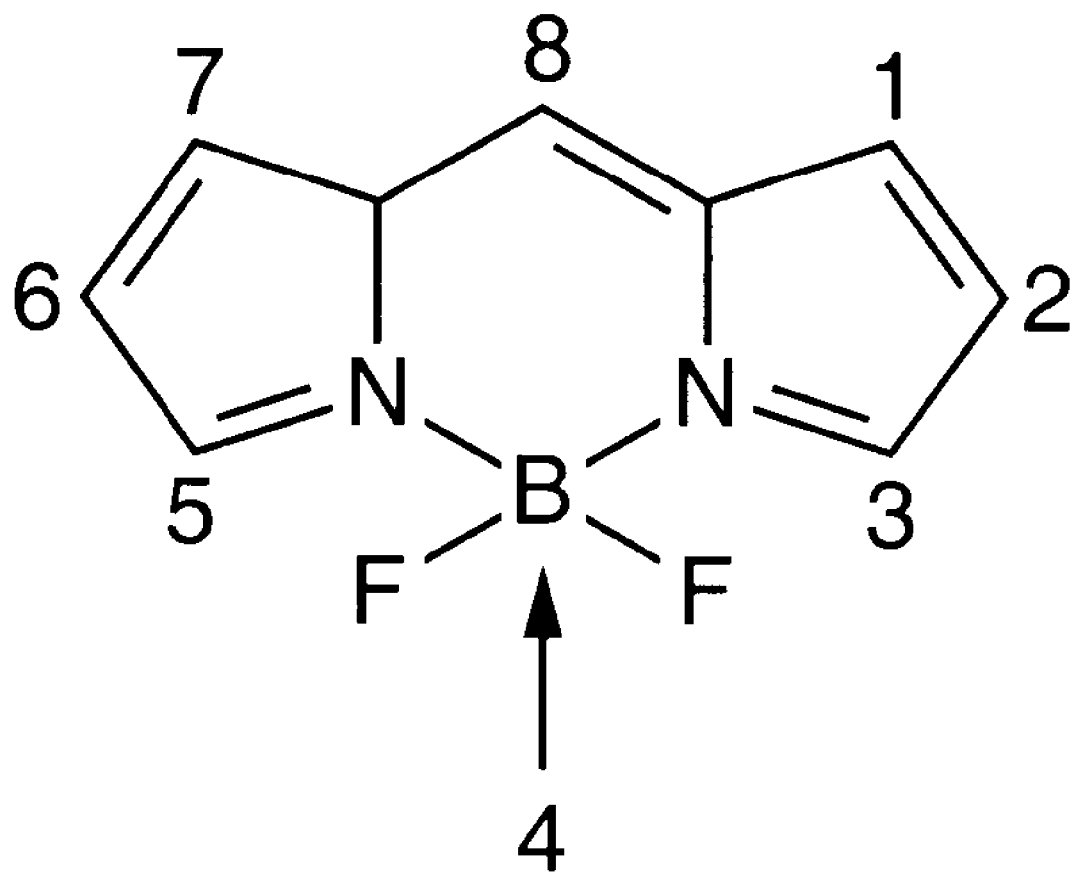

FIG. 19 shows the structure of dipyrromethenboron difluoride (4,4-difluoro-4-bora-3a,4a-diaza-s-indacene) dyes.

Figure 20:
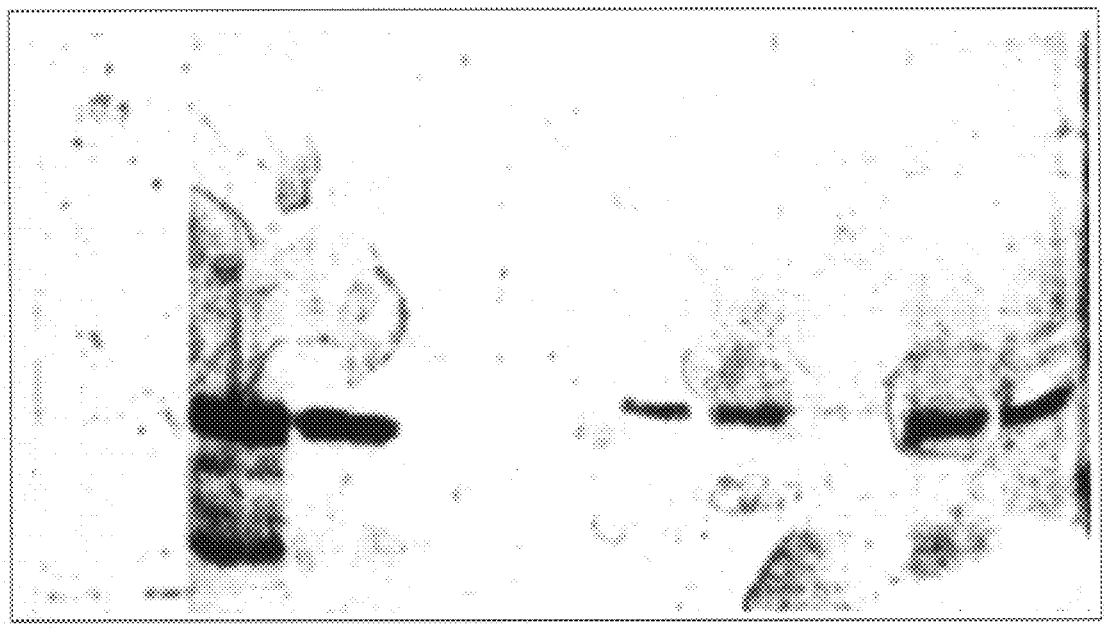

FIG. 20 is a photograph of a gel showing the incorporation of various fluorsecent molecules into hemolysin during translation.

Figure 21A:
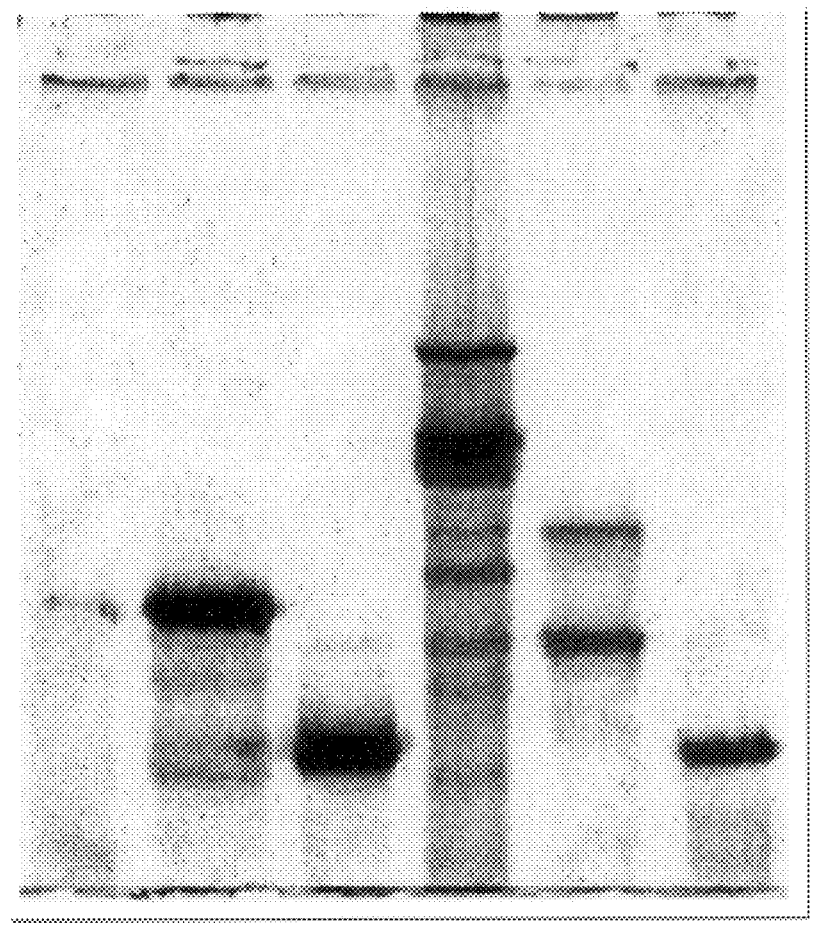
Figure 21B:
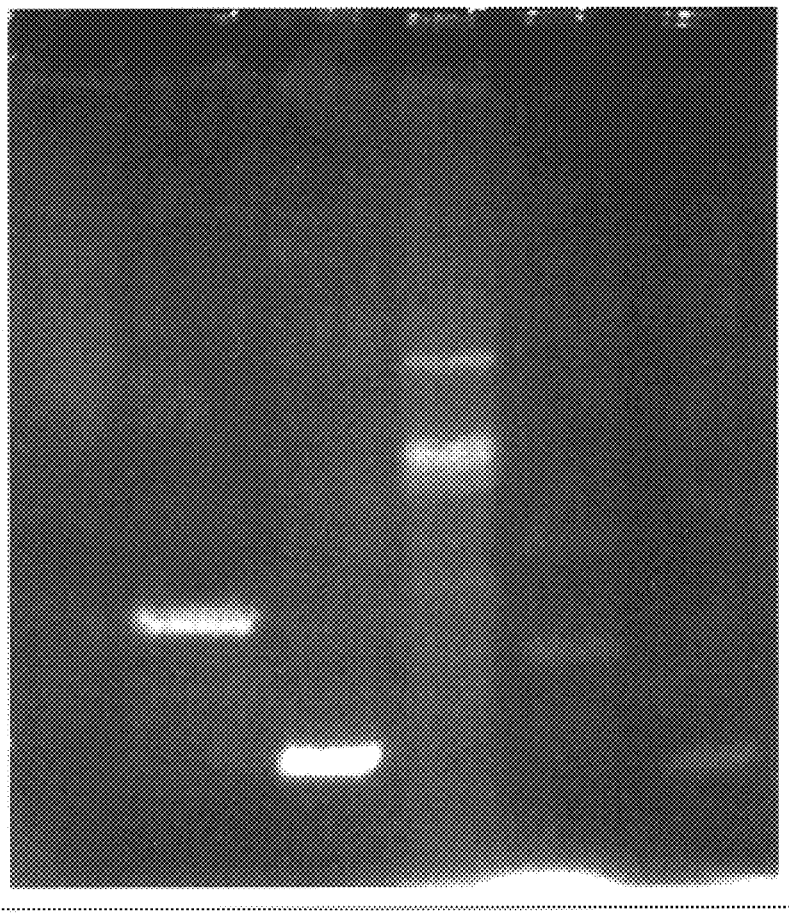

FIG. 21A shows the results of BODIPY-FL incorporation visualized by using a laser based Molecular Dynamics FluorImager 595. FIG. 21B shows the results of BODIPY-FL incorporation visualized by using a UV-transilluminator.

Figure 22A:
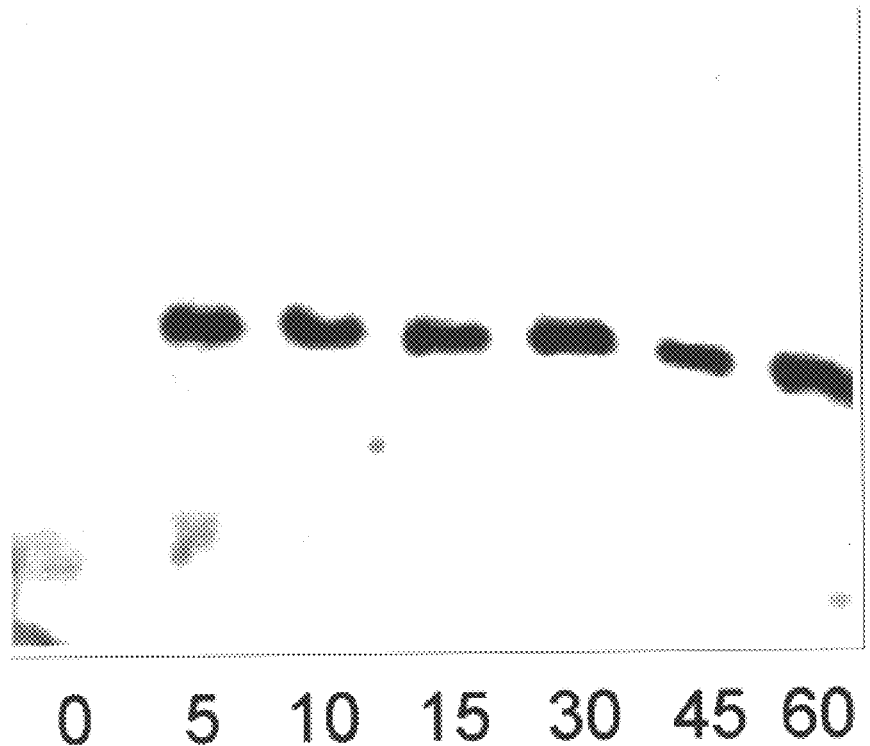
Figure 22B:
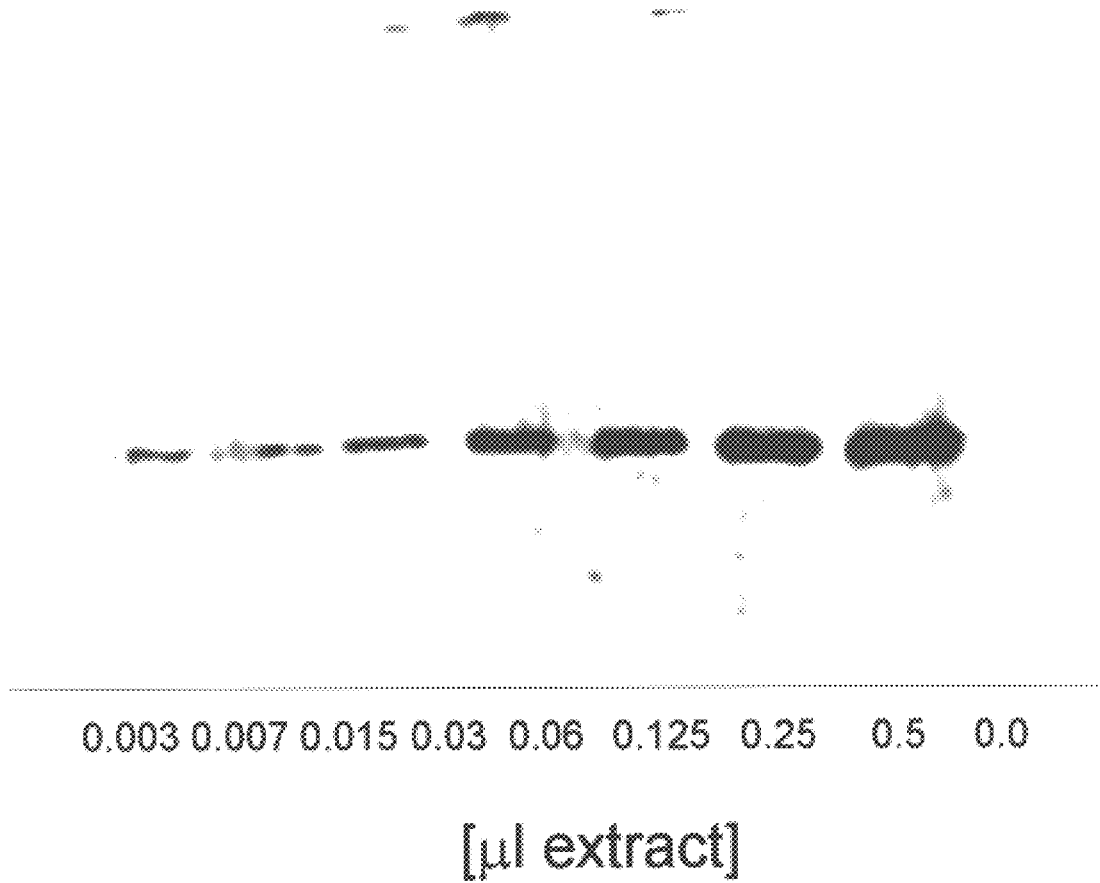

FIG. 22A shows a time course of fluorescence labeling. FIG. 22B shows the SDS-PAGE results of various aliquotes of the translation mixture, demonstrating the sensitivity of the system.

Figure 23A:
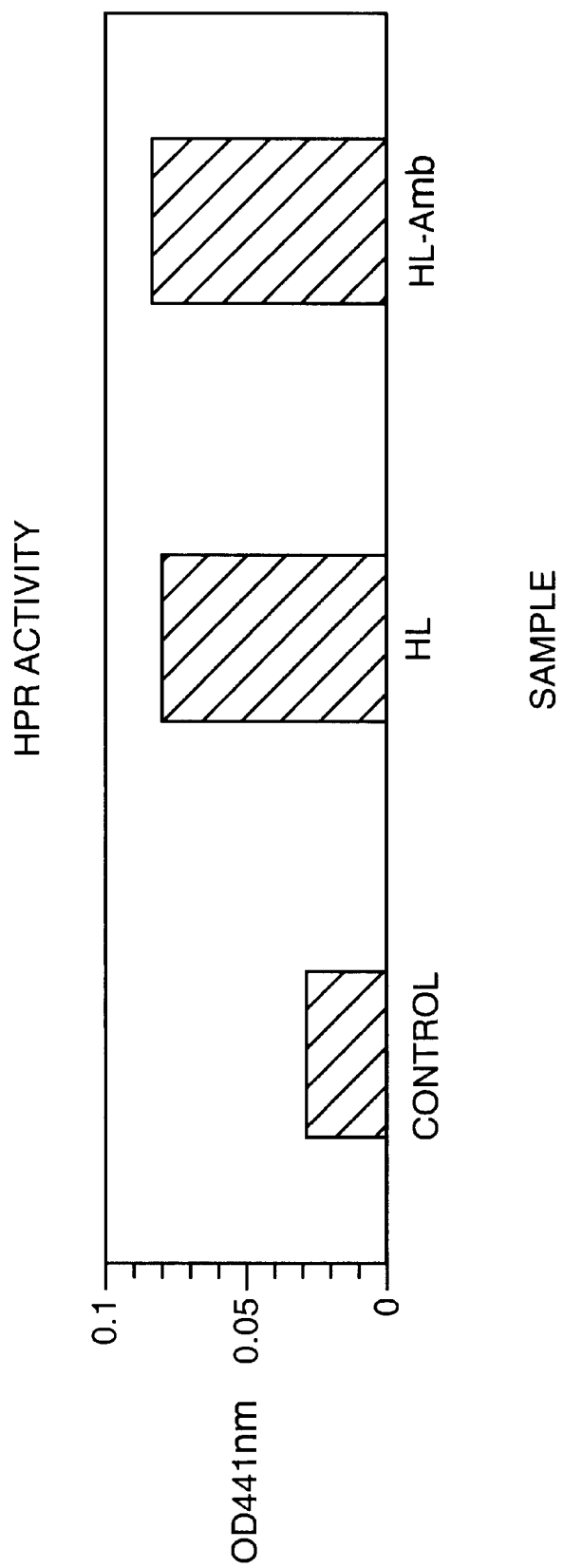
Figure 23B:
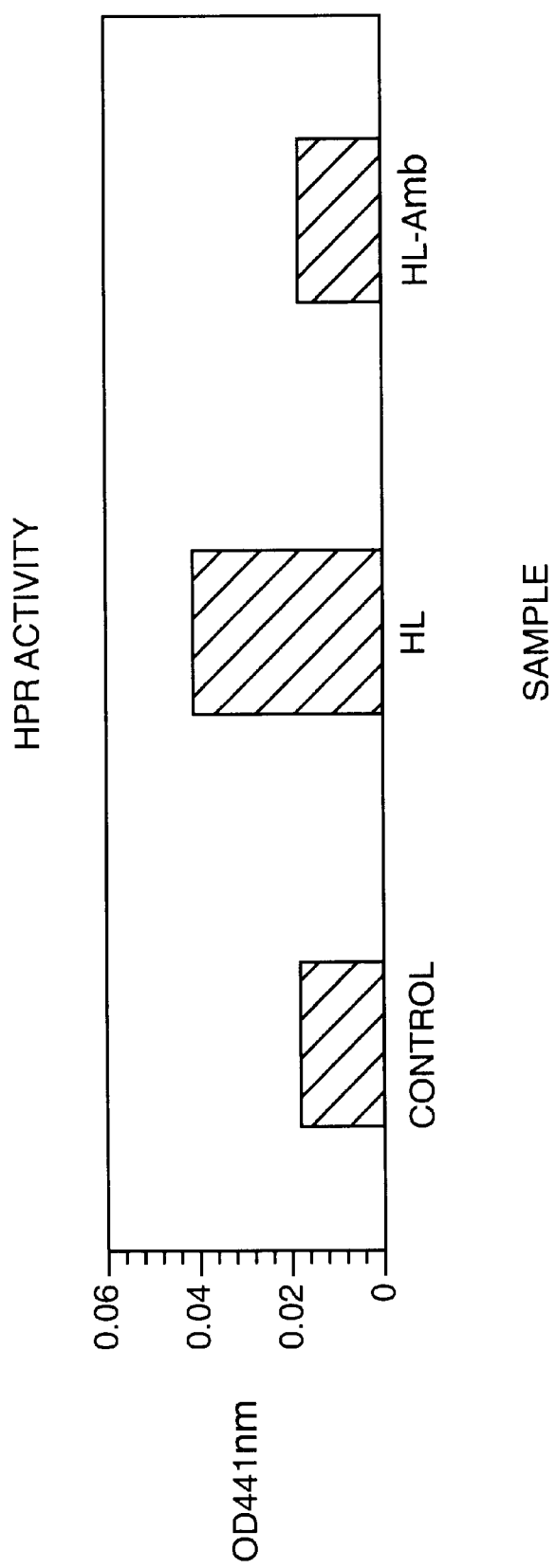

FIG. 23A is a bar graph showing gel-free quantitation of an N-terminal marker introduced into a nascent protein in accordance with the method of the present invention. FIG. 23B is a bar graph showing gel-free quantitation of an C-terminal marker of a nascent protein quantitated in accordance with the method of the present invention.

Figure 24:
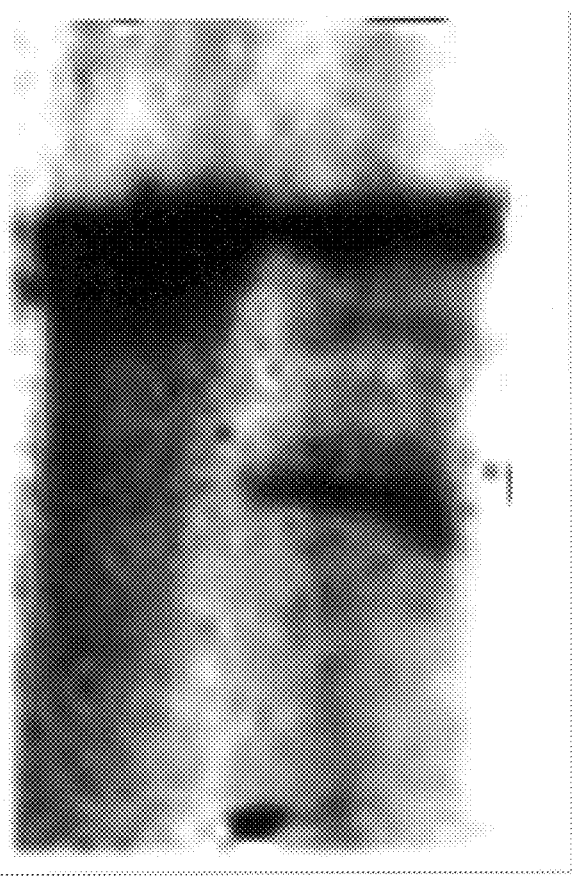

FIG. 24 shows gel results for protease treated and untreated protein.

Figure 25:

FIG. 25 shows gel results for protein treated with RBCs and untreated protein.

Figure 26A:
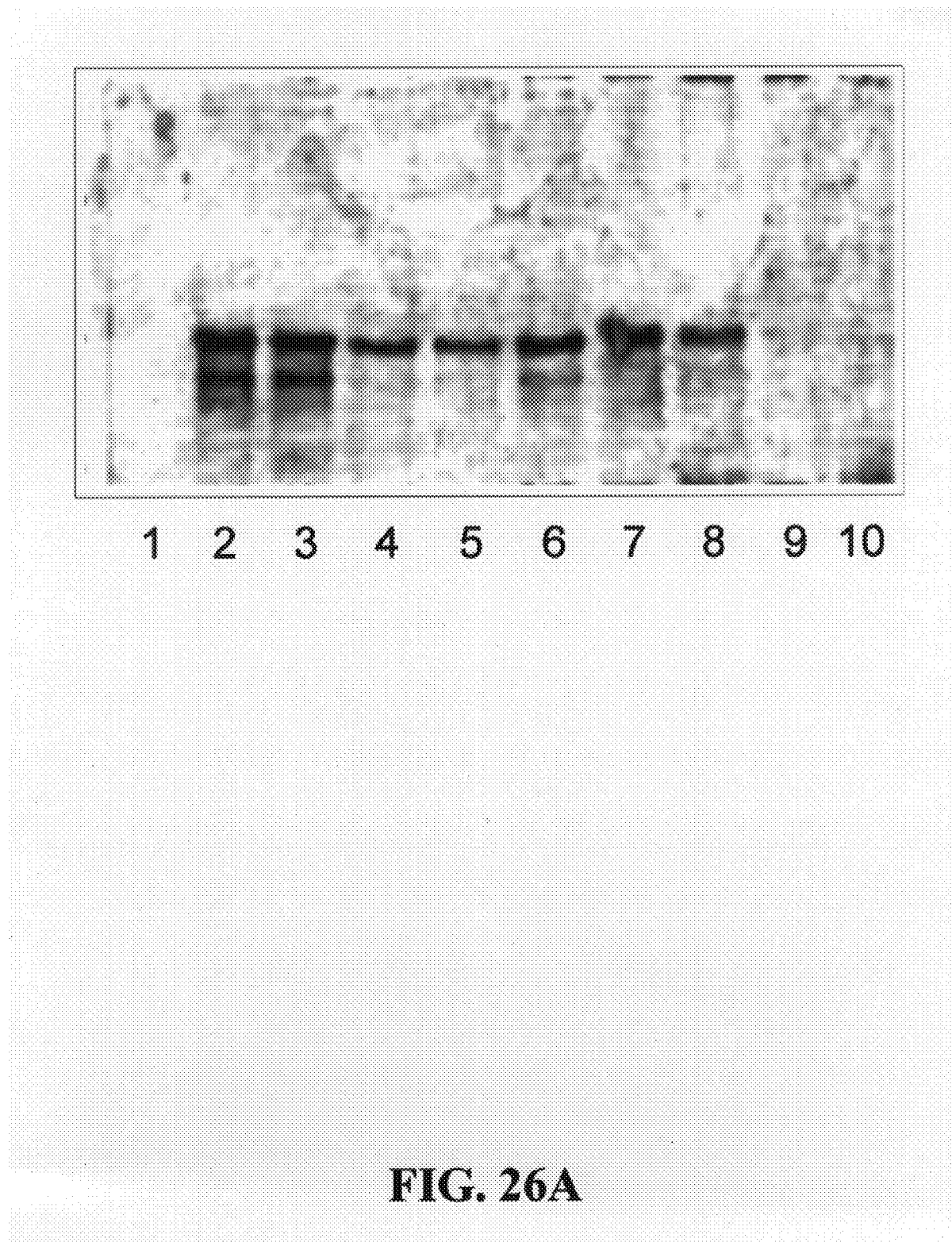

FIG. 26A is a gel showing the incorporation of various fluorescent molecules into α-hemolysin in *E. coli* translation system using misaminoacylated lysyl-tRNA$^{lys}$.

Figure 26B:
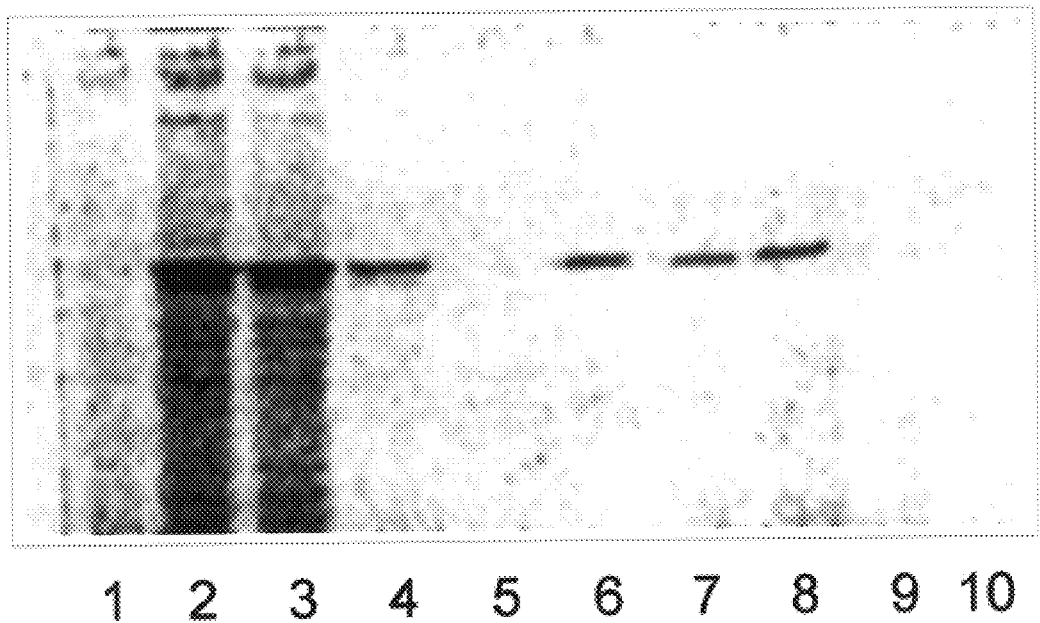

FIG. 26B shows the incorporation of various fluorescent molecules into luciferase in a TnT wheat germ system using misaminoacylated lysyl-tRNA$^{lys}$.

Figure 27:

FIG. 27 shows gel results of in vitro translation of α-HL carried out in the presence of various fluorescent-tRNAs, including atRNA-coumarin derivative.

Figure 28A:
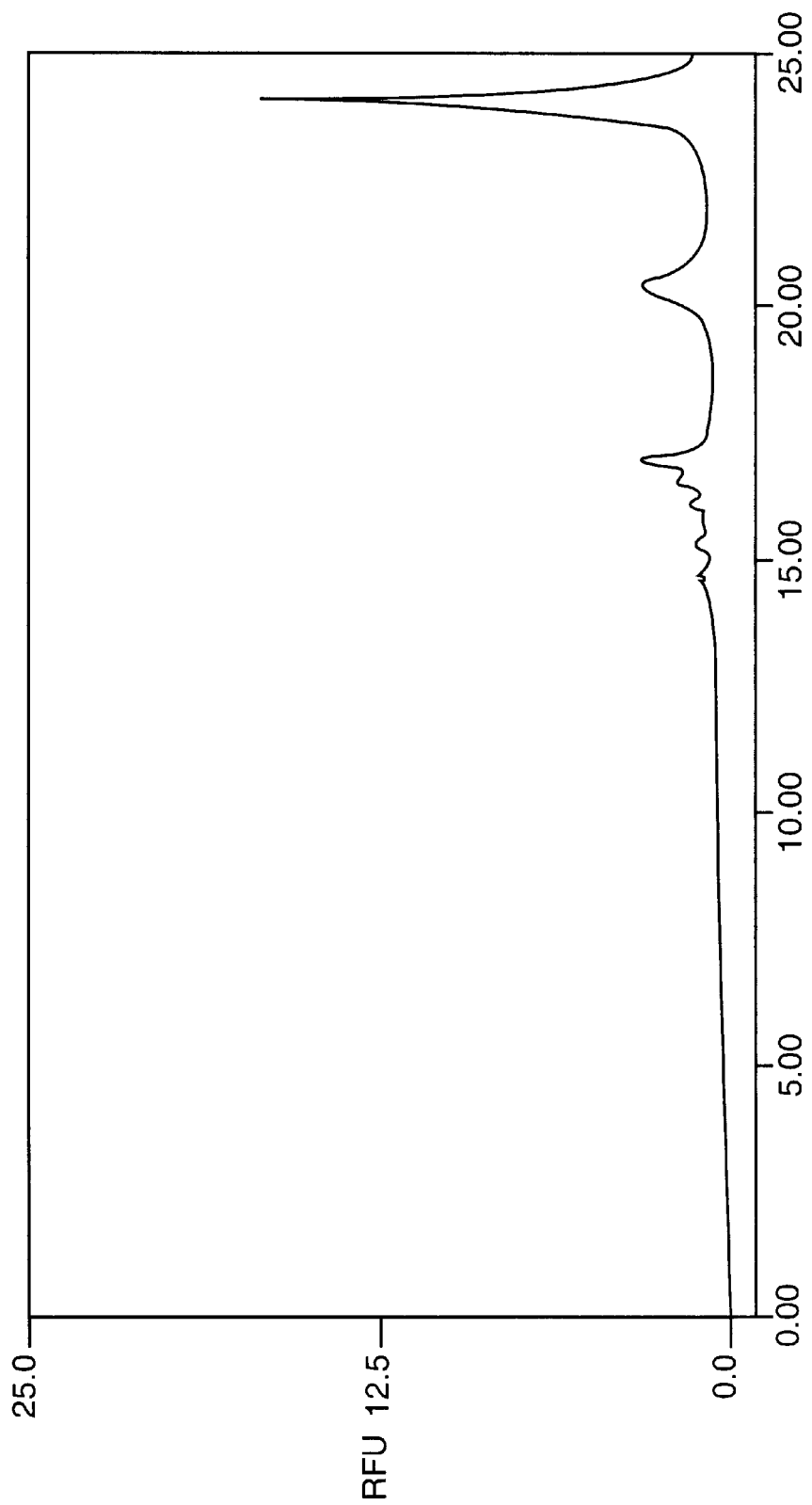
Figure 28B:
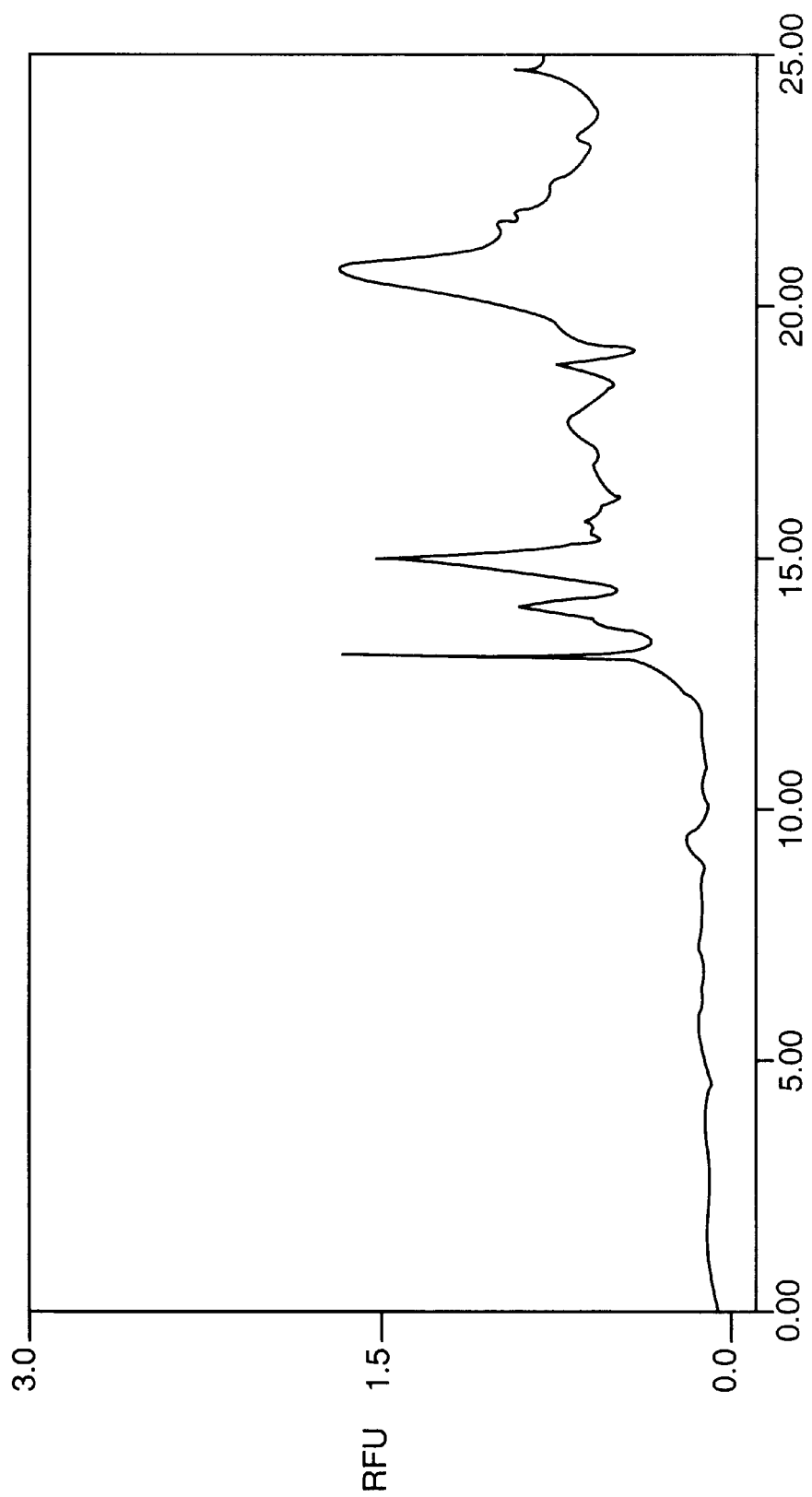

FIGS. 28A and 28B show mobility shift results by capillary electrophoresis.

Figure 29:
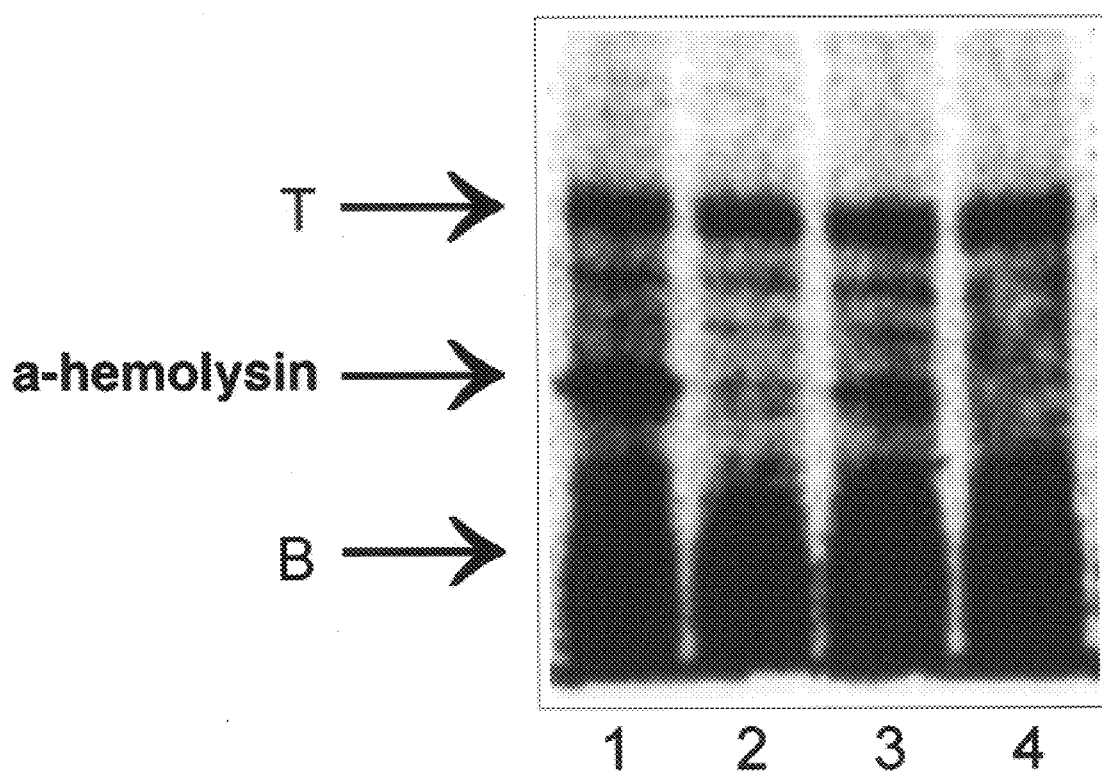

FIG. 29 are gel results of in vitro translation results wherein three markers were introduced into a nascent protein.

DESCRIPTION OF THE INVENTION

As embodied and described herein, the present invention comprises methods for the non-radioactive labeling and detection of the products of new or nascent protein synthesis, and methods for the isolation of these nascent proteins from preexisting proteins in a cellular or cell-free translation system. As radioactive labels are not used, there are no special measures which must be taken to dispose of waste materials. There is also no radioactivity danger or risk which would prevent further utilization of the translation product as occurs when using radioactive labels and the resulting protein product may be used directly or further purified. In addition, no prior knowledge of the protein sequence or structure is required which would involve, for example, unique suppressor tRNAs. Further, the sequence of the gene or mRNA need not be determined. Consequently, the existence of non-sense codons or any specific codons in the coding region of the mRNA is not necessary. Any tRNA can be used, including specific tRNAs for directed labeling, but such specificity is not required. Unlike post-translational labeling, nascent proteins are labeled with specificity and without being subjected to post-translational modifications which may effect protein structure or function.

One embodiment of the invention is directed to a method for labeling nascent proteins synthesized in a translation system. These proteins are labeled while being synthesized with detectable markers which are incorporated into the peptide chain. Markers which are aminoacylated to tRNA molecules, may comprise native amino acids, non-native amino acids, amino acid analogs or derivatives, or chemical moieties. These markers are introduced into nascent proteins from the resulting misaminoacylated tRNAs during the translation process. Aminoacylation is the process whereby a tRNA molecule becomes charged. When this process occurs in vivo, it is referred to as natural aminoacylation and the resulting product is an aminoacylated tRNA charged with a native amino acid. When this process occurs through artificial means, it is called misaminoacylation and a tRNA charged with anything but a native amino acid molecule is referred to as a misaminoacylated tRNA.

According to the present method, misaminoacylated tRNAs are introduced into a cellular or cell-free protein synthesizing system, the translation system, where they function in protein synthesis to incorporate detectable marker in place of a native amino acid in the growing peptide chain. The translation system comprises macromolecules including RNA and enzymes, translation, initiation and elongation factors, and chemical reagents. RNA of the system is required in three molecular forms, ribosomal RNA (rRNA), messenger RNA (mRNA) and transfer RNA (tRNA). mRNA carries the genetic instructions for building a peptide encoded within its codon sequence. tRNAs contain specific anti-codons which decode the mRNA and individually carry amino acids into position along the growing peptide chain. Ribosomes, complexes of rRNA and protein, provide a dynamic structural framework on which the translation process, including translocation, can proceed. Within the cell, individualized aminoacyl tRNA synthetases bind specific amino acids to tRNA molecules carrying the matching anti-codon creating aminoacylated or charged tRNAs by the process of aminoacylation. The process of translation including the aminoacylation or charging of a tRNA molecule is described in *Molecular Cell Biology* (J. Darnell et al. editors, Scientific American Books, N.Y., N.Y. 1991), which is hereby specifically incorporated by reference. Aminoacylation may be natural or by artificial means utilizing native amino acids, non-native amino acid, amino acid analogs or derivatives, or other molecules such as detectable chemicals or coupling agents. The resulting misaminoacylated tRNA comprises a native amino acid coupled with a chemical moiety, non-native amino acid, amino acid derivative or analog, or other detectable chemicals. These misaminoacylated tRNAs incorporate their markers into the growing peptide chain during translation forming labeled nascent proteins which can be detected and isolated by the presence or absence of the marker.

Any proteins that can be expressed by translation in a cellular or cell-free translation system may be nascent proteins and consequently, labeled, detected and isolated by the methods of the invention. Examples of such proteins include enzymes such as proteolytic proteins, cytokines, hormones, immunogenic proteins, carbohydrate or lipid binding proteins, nucleic acid binding proteins, human proteins, viral proteins, bacterial proteins, parasitic proteins and fragments and combinations. These methods are well adapted for the detection of products of recombinant genes and gene fusion products because recombinant vectors carrying such genes generally carry strong promoters which transcribe mRNAs at fairly high levels. These mRNAs are easily translated in a translation system.

Translation systems may be cellular or cell-free, and may be prokaryotic or eukaryotic. Cellular translation systems include whole cell preparations such as permeabilized cells or cell cultures wherein a desired nucleic acid sequence can be transcribed to mRNA and the mRNA translated.

Cell-free translation systems are commercially available and many different types and systems are well-known.

Examples of cell-free systems include prokaryotic lysates such as *Escherichia coli* lysates, and eukaryotic lysates such as wheat germ extracts, insect cell lysates, rabbit reticulocyte lysates, frog oocyte lysates and human cell lysates. Eukaryotic extracts or lysates may be preferred when the resulting protein is glycosylated, phosphorylated or otherwise modified because many such modifications are only possible in eukaryotic systems. Some of these extracts and lysates are available commercially (Promega; Madison, Wis.; Stratagene; La Jolla, Calif.; Amersham; Arlington Heights, Ill.; GIBCO/BRL; Grand Island, N.Y.). Membranous extracts, such as the canine pancreatic extracts containing microsomal membranes, are also available which are useful for translating secretory proteins. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors.

Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

tRNA molecules chosen for misaminoacylation with marker do not necessarily possess any special properties other than the ability to function in the protein synthesis system. Due to the universality of the protein translation system in living systems, a large number of tRNAs can be used with both cellular and cell-free reaction mixtures. Specific tRNA molecules which recognize unique codons, such as nonsense or amber codons (UAG), are not required.

Site-directed incorporation of the nonnative analogs into the protein during translation is also not required. Incorporation of markers can occur anywhere in the polypeptide and can also occur at multiple locations. This eliminates the need for prior information about the genetic sequence of the translated mRNA or the need for modifying this genetic sequence.

In some cases, it may be desirable to preserve the functional properties of the nascent protein. A subset of tRNAs which will incorporate markers at sites which do not interfere with protein function or structure can be chosen. Amino acids at the amino or carboxyl terminus of a polypeptide do not alter significantly the function or structure. tRNA molecules which recognize the universal codon for the initiation of protein translation (AUG), when misaminoacylated with marker, will place marker at the amino terminus. Prokaryotic protein synthesizing systems utilize initiator $tRNA^{fMet}$ molecules and eukaryotic systems initiator $tRNA^{Met}$ molecules. In either system, the initiator tRNA molecules are aminoacylated with markers which may be non-native amino acids or amino acid analogs or derivatives that possess marker, reporter or affinity properties. The resulting nascent proteins will be exclusively labeled at their amino terminus, although markers placed internally do not necessarily destroy structural or functional aspects of a protein. For example, a $tRNA^{LYS}$ may be misaminoacylated with the amino acid derivative dansyllysine which does not interfere with protein function or structure. In addition, using limiting amounts of misaminoacylated tRNAs, it is possible to detect and isolate nascent proteins having only a very small fraction labeled with marker which can be very useful for isolating proteins when the effects of large quantities of marker would be detrimental or are unknown.

tRNAs molecules used for aminoacylation are commercially available from a number of sources and can be prepared using well-known methods from sources including *Escherichia coli*, yeast, calf liver and wheat germ cells (Sigma Chemical; St. Louis, Mo.; Promega; Madison, Wis; Boehringer Mannheim Biochemicals; Indianapolis, Ind.). Their isolation and purification mainly involves cell-lysis, phenol extraction followed by chromatography on DEAE-cellulose. Amino-acid specific tRNA, for example $tRNA^{fmet}$, can be isolated by expression from cloned genes and over-expressed in host cells and separated from total tRNA by techniques such as preparative polyacrylamide gel electrophoresis followed by band excision and elution in high yield and purity (Seong and RajBhandary, Proc. Natl. Acad. Sci. USA 84:334–338, 1987). Run-off transcription allows for the production of any specific tRNA in high purity, but its applications can be limited due to lack of post-transcriptional modifications (Bruce and Uhlenbeck, Biochemistry 21:3921, 1982).

Misaminoacylated tRNAs are introduced into the cellular- or cell-free protein synthesis system. In the cell-free protein synthesis system, the reaction mixture contains all the cellular components necessary to support protein synthesis including ribosomes, tRNA, rRNA, spermidine and physiological ions such as magnesium and potassium at appropriate concentrations and an appropriate pH. Reaction mixtures can be normally derived from a number of different sources including wheat germ, *E. coli* (S-30), red blood cells (reticulocyte lysate,) and oocytes, and once created can be stored as aliquots at about +4° C. to −70° C. The method of preparing such reaction mixtures is described by J. M. Pratt (*Transcription and Translation*, B. D. Hames and S. J. Higgins, Editors, p. 209, IRL Press, Oxford, 1984) which is hereby incorporated by reference. Many different translation systems are commercially available from a number of manufacturers.

The misaminoacylated tRNA is added directly to the reaction mixture as a solution of predetermined volume and concentration. This can be done directly prior to storing the reaction mixture at −70° C. in which case the entire mixture is thawed prior to initiation of protein synthesis. Efficient incorporation of markers into nascent proteins is sensitive to the final pH and magnesium ion concentration. Reaction mixtures are normally about pH 6.8 and contain a magnesium ion concentration of about 3 mM. These conditions impart stability to the base-labile aminoacyl linkage of the misaminoacylated tRNA. Aminoacylated tRNAs are available in sufficient quantities from the translation extract. Misaminoacylated tRNAs charged with markers are added at between about 1.0 $\mu$g/ml to about 1.0 mg/ml, preferably at between about 10 $\mu$g/ml to about 500 $\mu$g/ml, and more preferably at about 150 $\mu$g/ml.

Initiation of protein synthesis occurs upon addition of a quantity of mRNA or DNA to the reaction mixture containing the misaminoacylated tRNAs. mRNA molecules may be prepared or obtained from recombinant sources, or purified from other cells by procedure such as poly-dT chromatography. One method of assuring that the proper ratio of the reaction mixture components is to use predetermined volumes that are stored in convenient containers such as vials or standard microcentrifuge tubes. For example, DNA and/or mRNA coding for the nascent proteins and the misaminoacylated tRNA solution are premixed in proper amounts and stored separately in tubes. Tubes are mixed when needed to initiate protein synthesis.

Translations in cell-free systems generally require incubation of the ingredients for a period of time. Incubation times range from about 5 minutes to many hours, but is preferably between about thirty minutes to about five hours and more preferably between about one to about three hours. Incubation may also be performed in a continuous manner whereby reagents are flowed into the system and nascent proteins removed or left to accumulate using a continuous flow system (A. S. Spirin et al., Sci. 242:1162–64, 1988). This process may be desirable for large scale production of nascent proteins. Incubations may also be performed using a dialysis system where consumable reagents are available for the translation system in an outer reservoir which is separated from larger components of the translation system by a dialysis membrane [Kim, D., and Choi, C. (1996) Biotechnol Prog 12, 645–649]. Incubation times vary significantly with the volume of the translation mix and the temperature of the incubation. Incubation temperatures can be between about 4° C. to about 60° C., and are preferably between about 15° C. to about 50° C., and more preferably between about 25° C. to about 45° C. and even more preferably at about 25° C. or about 37° C. Certain markers may be sensitive to temperature fluctuations and in such cases, it is preferable to conduct those incubations in the non-sensitive ranges. Translation mixes will typically comprise buffers such as Tris-HCl, Hepes or another suitable buffering agent to maintain the pH of the solution between about 6 to 8, and preferably at about 7. Again, certain markers may be pH sensitive and in such cases, it is preferable to conduct incubations outside of the sensitive ranges for the marker. Translation efficiency may not be optimal, but marker utility will be enhanced. Other reagents which may be in the translation system include dithiothreitol (DTT) or 2-mercaptoethanol as reducing agents, RNasin to inhibit RNA breakdown, and nucleoside triphosphates or creatine phosphate and creatine kinase to provide chemical energy for the translation process.

In cellular protein synthesis, it is necessary to introduce misaminoacylated tRNAs or markers into intact cells, cell organelles, cell envelopes and other discrete volumes bounded by an intact biological membrane, which contain a protein synthesizing system. This can be accomplished through a variety of methods that have been previously established such as sealing the tRNA solution into liposomes or vesicles which have the characteristic that they can be induced to fuse with cells. Fusion introduces the liposome or vesicle interior solution containing the tRNA into the cell. Alternatively, some cells will actively incorporate liposomes into their interior cytoplasm through phagocytosis. The tRNA solution could also be introduced through the process of cationic detergent mediated lipofection (Felgner et al., Proc. Natl. Acad. Sci. USA 84:7413–17, 1987), or injected into large cells such as oocytes. Injection may be through direct perfusion with micropipettes or through the method of electroporation.

Alternatively, cells can be permeabilized by incubation for a short period of time in a solution containing low concentrations of detergents in a hypotonic media. Useful detergents include Nonidet-P 40 (NP40), Triton X-100 (TX-100) or deoxycholate at concentrations of about 0.01 nM to 1.0 mM, preferably between about 0.1 $\mu$M to about 0.01 mM, and more preferably about 1 $\mu$M. Permeabilized cells allow marker to pass through cellular membranes unaltered and be incorporated into nascent proteins by host cell enzymes. Such systems can be formed from intact cells in culture such as bacterial cells, primary cells, immortalized cell lines, human cells or mixed cell populations. These cells may, for example, be transfected with an appropriate vector containing the gene of interest, under the control of a strong and possibly regulated promoter. Messages are expressed from these vectors and subsequently translated within cells. Intact misaminoacylated tRNA molecules, already charged with a non-radioactive marker could be introduced to cells and incorporated into translated product.

Figure 4:
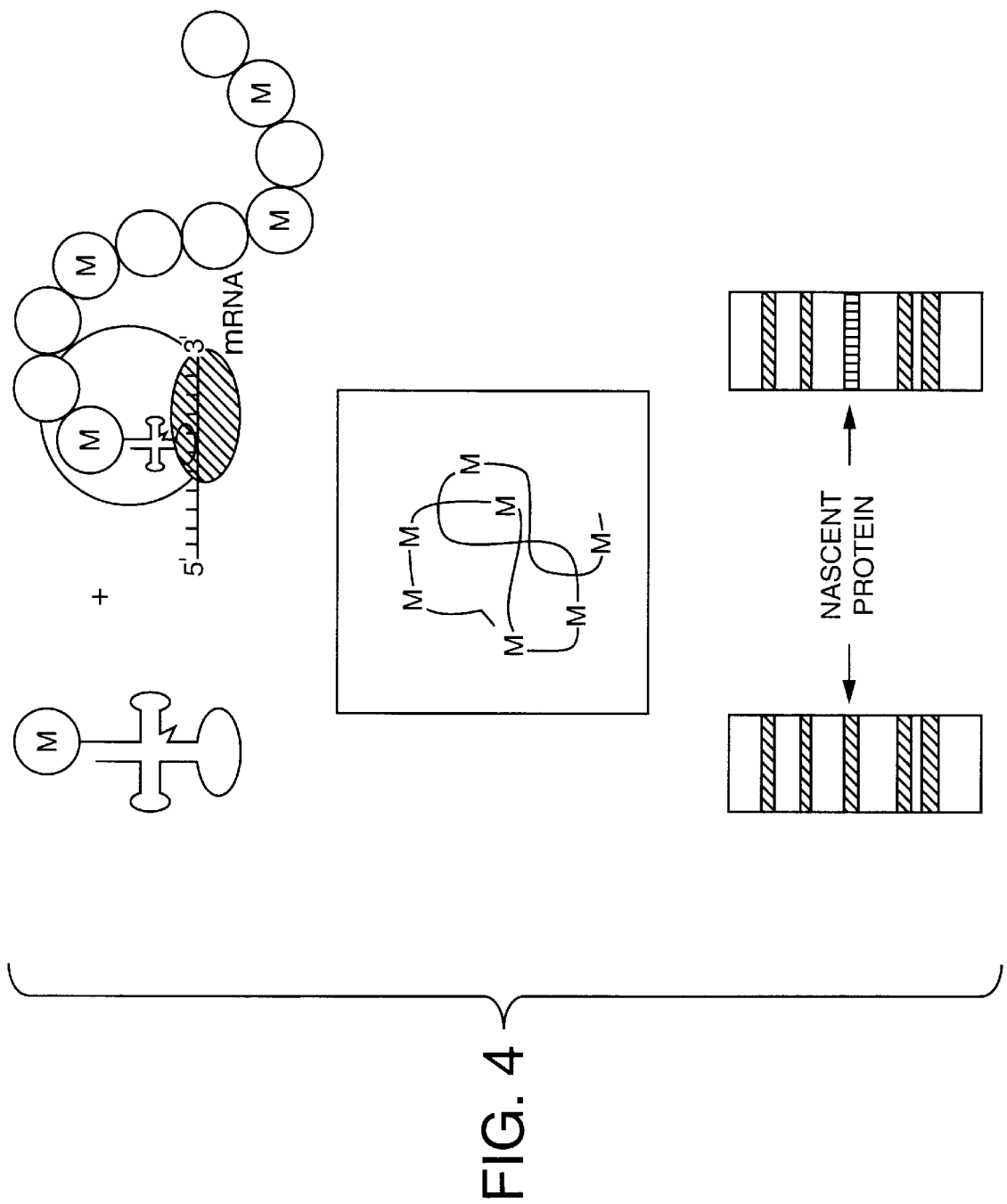
FIG. 4 is a schematic representation of the method of detecting nascent proteins using fluorescent marker amino acids.

One example of the use of misaminoacylation to detect nascent protein is schematically represented in FIG. 4. A tRNA molecule is misaminoacylated with the marker which is highly fluorescent when excited with UV (ultraviolet) radiation. The misaminoacylated tRNA is then introduced into a cell-free protein synthesis extract and the nascent proteins containing the marker analog produced. Proteins in the cell-free extract are separated by polyacrylamide gel electrophoresis (PAGE). The resulting gel contains bands which correspond to all of the proteins present in the cell-free extract. The nascent protein is identified upon UV illumination of the gel by detection of fluorescence from the band corresponding to proteins containing marker. Detection can be through visible observation or by other conventional means of fluorescence detection.

The misaminoacylated tRNA can be formed by natural aminoacylation using cellular enzymes or misaminoacylation such as chemical misaminoacylation. One type of chemical misaminoacylation involves truncation of the tRNA molecule to permit attachment of the marker or marker precursor. For example, successive treatments with periodate plus lysine, pH 8.0, and alkaline phosphatase removes 3'-terminal residues of any tRNA molecule generating tRNA-OH-3' with a mononucleotide or dinucleotide deletion from the 3'-terminus (Neu and Heppel, J. Biol. Chem. 239:2927–34, 1964). Alternatively, tRNA molecules may be genetically manipulated to delete specific portions of the tRNA gene. The resulting gene is transcribed producing truncated tRNA molecules (Sampson and Uhlenbeck, Proc. Natl. Acad. Sci. USA 85:1033–37, 1988). Next, a dinucleotide is chemically linked to a modified amino acid or other marker by, for example, acylation. Using this procedure, markers can be synthesized and acylated to dinucleotides in high yield (Hudson, J. Org. Chem. 53:617–624, 1988; Happ et al., J. Org. Chem. 52:5387–91, 1987). These modified groups are bound together and linked via the dinucleotide to the truncated tRNA molecules in a process referred to as ligase coupling (FIG. 3B).

Figure 1A:
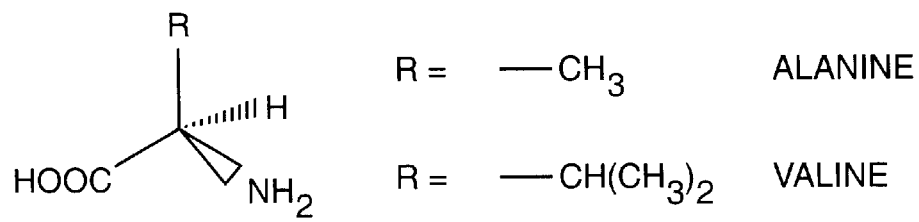
Figure 1B:
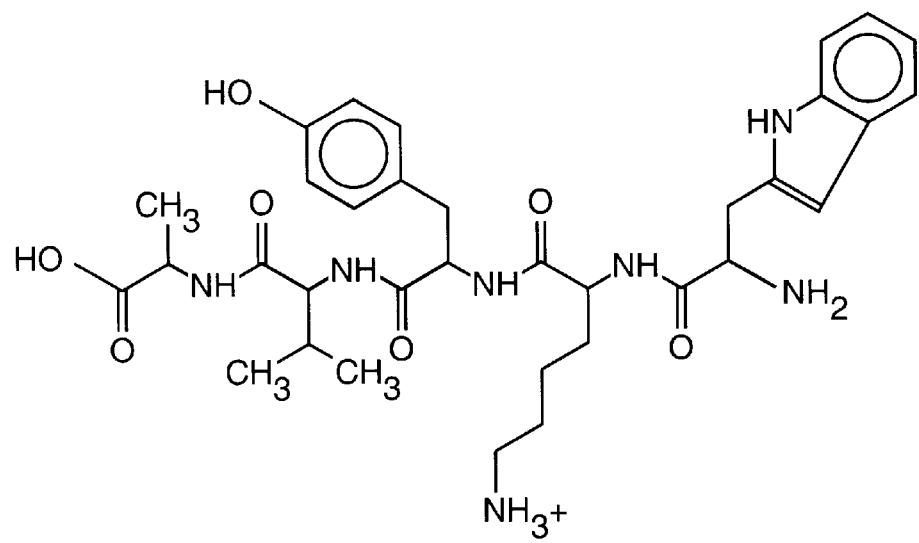
Figure 2:
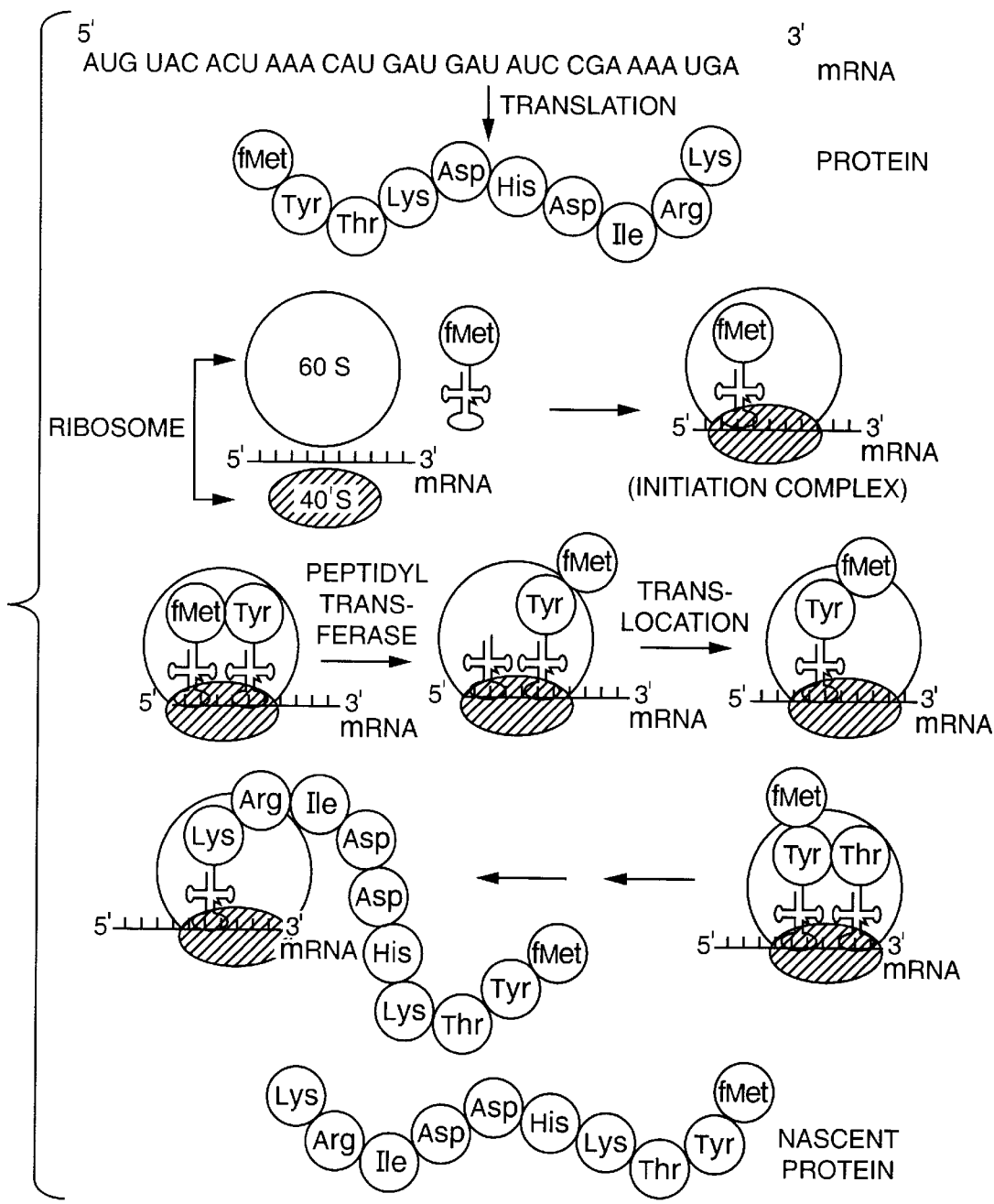
Figure 3A:
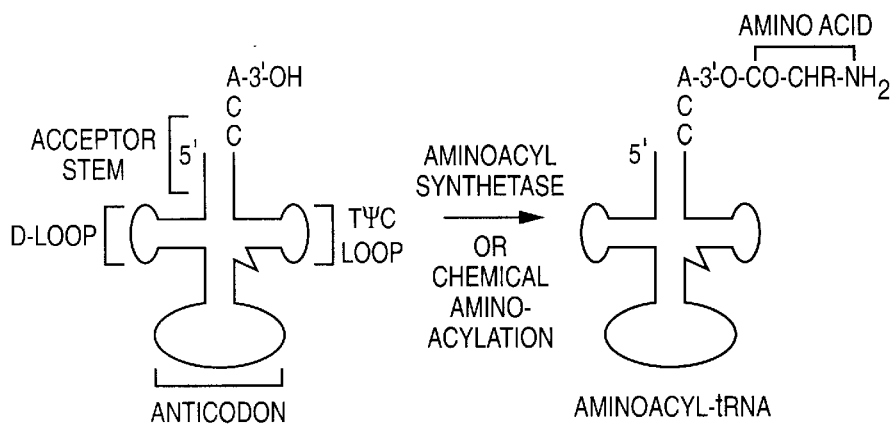
FIG. 3(A) shows a structure of a tRNA molecule.
Figure 3B:
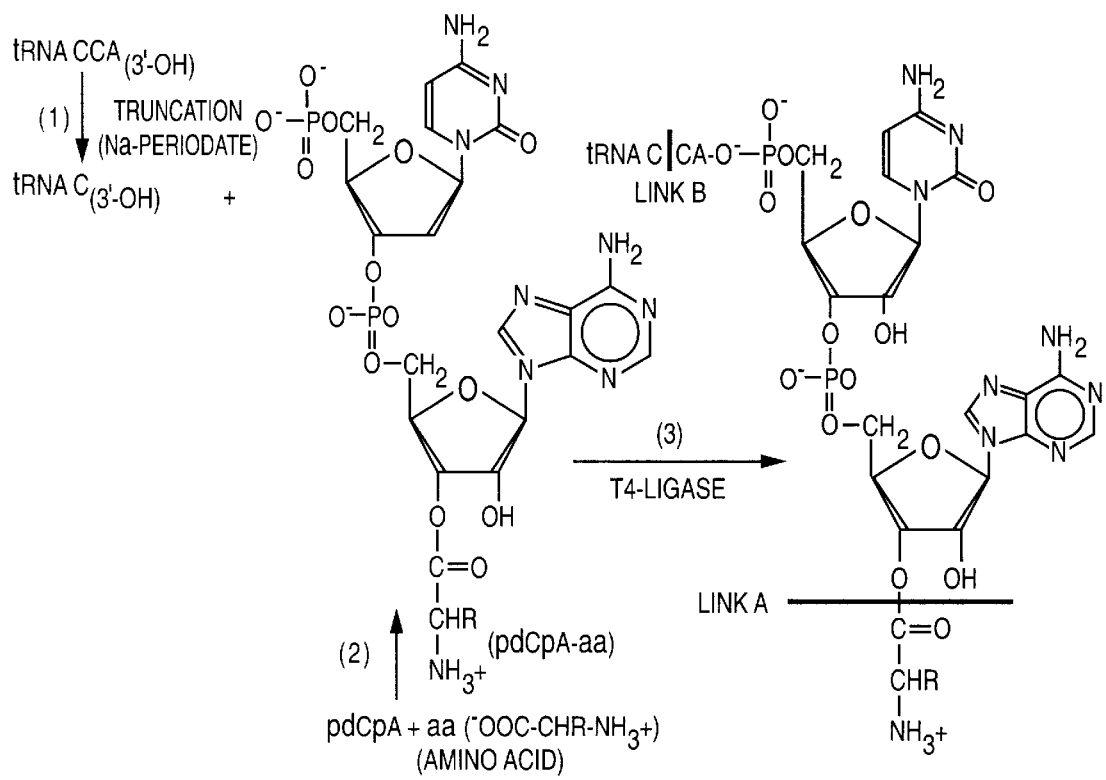
FIG. 3(B) approaches involved in the aminoacylation of tRNAs.

A different bond is involved in misaminoacylation (FIG. 3B, link B) than the bond involved with activation of tRNA by aminoacyl tRNA synthetase (FIG. 3B, link A). As T4 RNA ligase does not recognize the acyl substituent, tRNA molecules can be readily misaminoacylated with few chemical complications or side reactions (link B, FIG. 3B) (T. G. Heckler et al., Biochemistry 23:1468–73, 1984; and T. G. Heckler et al., Tetrahedron 40:87–94, 1984). This process is insensitive to the nature of the attached amino acid and allows for misaminoacylation using a variety of non-native amino acids. In contrast, purely enzymatic aminoacylation (link A) is highly sensitive and specific for the structures of substrate tRNA and amino acids.

Markers are basically molecules which will be recognized by the enzymes of the translation process and transferred from a charged tRNA into a growing peptide chain. To be useful, markers must also possess certain physical and physio-chemical properties. Therefore, there are multiple criteria which can be used to identify a useful marker. First, a marker must be suitable for incorporation into a growing peptide chain. This may be determined by the presence of chemical groups which will participate in peptide bond formation. Second, markers should be attachable to a tRNA molecule. Attachment is a covalent interaction between the 3'-terminus of the tRNA molecule and the carboxy group of the marker or a linking group attached to the marker and to a truncated tRNA molecule. Linking groups may be nucleotides, short oligonucleotides or other similar molecules and are preferably dinucleotides and more preferably the dinucleotide CA. Third, markers should have one or more physical properties that facilitate detection and possibly isolation of nascent proteins. Useful physical properties include a characteristic electromagnetic spectral property such as emission or absorbance, magnetism, electron spin resonance, electrical capacitance, dielectric constant or electrical conductivity.

Useful markers are native amino acids coupled with a detectable label, detectable non-native amino acids, detectable amino acid analogs and detectable amino acid derivatives. Labels and other detectable moieties may be ferromagnetic, paramagnetic, diamagnetic, luminescent, electrochemiluminescent, fluorescent, phosphorescent, chromatic or have a distinctive mass. Fluorescent moieties which are useful as markers include dansyl fluorophores, coumarins and coumarin derivatives, fluorescent acridinium moieties and benzopyrene based fluorophores. Preferably, the fluorescent marker has a high quantum yield of fluorescence at a wavelength different from native amino acids and more preferably has high quantum yield of fluoresence can be excited in both the UV and visible portion of the spectrum. Upon excitation at a preselected wavelength, the marker is detectable at low concentrations either visually or using conventional fluorescence detection methods. Electrochemiluminescent markers such as ruthenium chelates and its derivatives or nitroxide amino acids and their derivatives are preferred when extreme sensitivity is desired (J. DiCesare et al., BioTechniques 15:152–59, 1993). These markers are detectable at the femtomolar ranges and below.

In addition to fluorescent markers, a variety of markers possessing other specific physical properties can be used to detect nascent protein production. In general, these properties are based on the interaction and response of the marker to electromagnetic fields and radiation and include absorption in the UV, visible and infrared regions of the electromagnetic spectrum, presence of chromophores which are Raman active, and can be further enhanced by resonance Raman spectroscopy, electron spin resonance activity and nuclear magnetic resonances and use of a mass spectrometer to detect presence of a marker with a specific molecular mass. These electromagnetic spectroscopic properties are preferably not possessed by native amino acids or are readily distinguishable from the properties of native amino acids. For example, the amino acid tryptophan absorbs near 290 nm, and has fluorescent emission near 340 nm when excited with light near 290 nm. Thus, tryptophan analogs with absorption and/or fluorescence properties that are sufficiently different from tryptophan can be used to facilitate their detection in proteins.

Figure 5:
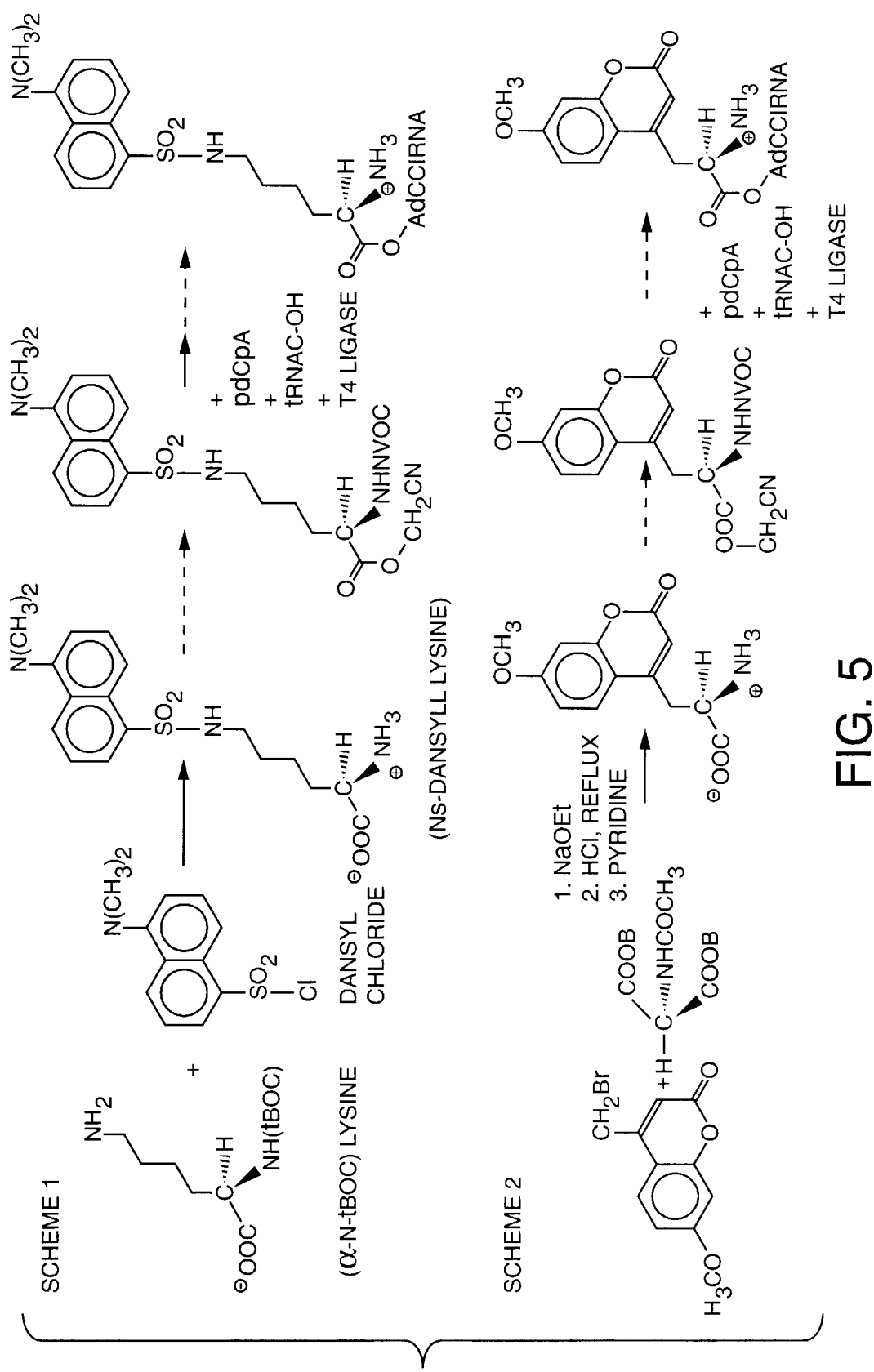
FIG. 5 shows schemes for synthesis and misaminoacylation to tRNA of two different marker amino acids, dansyllysine (scheme 1) and coumarin (scheme 2), with fluorescent properties suitable for the detection of nascent proteins using gel electrophoresis and UV illumination.

Many different modified amino acids which can be used as markers are commercially available (Sigma Chemical; St. Louis, Mo.; Molecular Probes; Eugene, Oreg.). One such marker is N∈-dansyllysine created by the misaminoacylation of a dansyl fluorophore to a tRNA molecule (FIG. 5; scheme 1). The α-amino group of N∈-dansyllysine is first blocked with NVOC (ortho-nitro veratryl oxycarbonyl chloride) and the carboxyl group activated with cyanomethyl ester. Misaminoacylation is performed as described. The misaminoacylated tRNA molecules are then introduced into the protein synthesis system, whereupon the dansyllysine is incorporated directly into the newly synthesized proteins.

Another such marker is a fluorescent amino acid analog based on the highly fluorescent molecule coumarin (FIG. 5; scheme 2). This fluorophore has a much higher fluorescence quantum yield than dansyl chloride and can facilitate detection of much lower levels of nascent protein. In addition, this coumarin derivative has a structure similar to the native amino acid tryptophan. These structural similarities are useful where maintenance of the nascent proteins' native structure or function are important or desired. Coumarin is synthesized as depicted in FIG. 5 (scheme 2). Acetamidomalonate is alkylated with a slight excess of 4-bromomethyl coumarin (Aldrich Chemicals; Milwaukee; Wis.) in the presence of sodium ethoxide followed by acid hydrolysis. The corresponding amino acid as a hydrochloride salt that can be converted to the free amino acid analog.

The coumarin derivative can be used most advantageously if it misamino-acylates the tryptophan-tRNA, either enzymatically or chemically. When introduced in the form of the misaminoacylated tryptophan-tRNA, the coumarin amino acid will be incorporated only into tryptophan positions. By controlling the concentration of misaminoacylated tRNAs or free coumarin derivatives in the cell-free synthesis system, the number of coumarin amino acids incorporated into the nascent protein can also be controlled. This procedure can be utilized to control the amount of most any markers in nascent proteins.

Markers can be chemically synthesized from a native amino acid and a molecule with marker properties which cannot normally function as an amino acid. For example a highly fluorescent molecule can be chemically linked to a native amino acid group. The chemical modification can occur on the amino acid side-chain, leaving the carboxyl and amino functionalities free to participate in a polypeptide bond formation. Highly fluorescent dansyl chloride can be linked to the nucleophilic side chains of a variety of amino acids including lysine, arginine, tyrosine, cysteine, histidine, etc., mainly as a sulfonamide for amino groups or sulfate bonds to yield fluorescent derivatives. Such derivatization leaves the ability to form peptide bond intact, allowing the normal incorporation of dansyllysine into a protein.

A number of factors determine the usefulness of a marker which is to be incorporated into nascent proteins through misaminoacylated tRNAs. These include the ability to incorporate the marker group into the protein through the use of a misaminoacylated tRNA in a cell-free or cellular protein synthesis system and the intrinsic detectability of the marker once it is incorporated into the nascent protein. In general, markers with superior properties will allow shorter incubation times and require smaller samples for the accurate detection of the nascent proteins. These factors directly influence the usefulness of the methods described. In the case of fluorescent markers used for the incorporation into nascent proteins, favorable properties can be but are not limited to, small size, high quantum yield of fluorescence, and stability to prolonged light exposure (bleach resistance).

Even with knowledge of the above factors, the ability to incorporate a specific marker into a protein using a specific cell-free or cellular translation system is difficult to determine a priori since it depends on the detailed interaction of the marker group with components of the protein translational synthesis system including the tRNA, initiation or elongation factors and components of the ribosome. While it is generally expected that markers with smaller sizes can be accommodated more readily into the ribosome, the exact shape of the molecule and its specific interactions in the ribosomal binding site will be the most important determinant. For this reason, it is possible that some markers which are larger in size can be more readily incorporated into nascent proteins compared to smaller markers. For example, such factors are very difficult to predict using known methods of molecular modeling.

One group of fluorophores with members possessing several favorable properties (including favorable interactions with components of the protein translational synthesis system) is the group derived from dipyrromethenboron difluoride derivatives (BODIPY) (FIG. 19). Compared to a variety of other commonly used fluorophores with advantageous properties such as high quantum yields, some BODIPY compounds have the additional unusual property that they are highly compatible with the protein synthesis system. The core structure of all BODIPY fluorophores is 4,4-difluoro-4-bora-3a,4a-diaza-s-indacene. See U.S. Pat. Nos. 4,774,339; 5,187,288; 5,248,782; 5,274,113; 5,433,896; 5,451,663, all hereby incorporated by reference. A central feature is a difluoroboron as shown in FIG. 19. All BODIPY fluorophores have several desirable properties for a marker (Molecular Probes Catalog, pages 13–18) including a high extinction coefficient, high fluorescence quantum yield, spectra that are insensitive to solvent polarity and pH, narrow emission bandwidth resulting in a higher peak intensity compared to other dyes such as fluoresceine, absence of ionic charge and enhanced photostability compared to fluorosceine. The addition of substituents to the basic BODIPY structure which cause additional conjugation can be used to shift the wavelength of excitation or emission to convenient wavelengths compatible with the means of detection.

These dyes were described for the first time by Vos de Waal et al. (1977) and its fluorescence properties subsequently described by Wories [See Wories et al., "A novel water-soluble fluorescent probe: Synthesis, luminescence and biological properties of the sodium salt of the 4-sulfonato-3,3', 5'5-tetramethyl-2,2'-pyrromethen-1,1'-BF.sub.2 complex," Recl. Trav. Chim. PAYSBAS 104, 288 (1985). Dyes derived from dipyrromethenboron difluoride have additional characteristics that make them suitable for incorporation into nascent proteins. Simple alkyl derivatives of the fluorophore 4,4-difluoro-4-bora-3a,4a-diaza-s-indacene have been described by Treibs & Kreuzer, [Difluorboryl-komplexe von di-und tripyrrylmethenen, LIEBIGS ANNALEN CHEM. 718,208 (1968)] and by Worries, Kopek, Lodder, & Lugtenburg, [A novel water-soluble fluorescent probe: Synthesis, luminescence and biological properties of the sodium salt of the 4-sulfonato-3,3',5,5'-tetramethyl-2,2'-pyrromethen-1,1'-BF.sub.2 complex, RECL. TRAV. CHIM. PAYS-BAS 104, 288 (1985)] as being highly fluorescent with spectral properties that are similar to fluorescein, with maximum absorbance at about 490 to 510 nm and maximum emission at about 500 to 530 nm. U.S. Pat. No. 4,774,339 to Haugland et al. (1988) ('339 patent) (hereby incorporated by reference) describes 4,4-difluoro-4-bora-3a,4a-diaza-s-indacene (dipyrromethenboron difluoride) dyes including hydrogen, halogen, alkyl, cycloalkyl, aryl, arylalkyl, acyl, and sulfo-substituted derivatives that contain reactive groups suitable for conjugation to biomolecules, that have good photostability, and which have fluorescein-like spectra. As described in the '339 patent, and by Pavlopoulos, et al., [Laser action from a tetramethylpyrromethene-BF.sub.2 complex, APP. OPTICS 27, 4998 (1988)], the emission of the alkyl derivatives of 4,4-difluoro-4-bora-3a,4a-diaza-s-indacene fluorescent dyes clearly overlaps that of fluorescein. The overlap allows the alkyl derivatives of dipyrromethenboron difluoride to be used with the same optical equipment as used with fluorescein-based dyes without modification of the excitation sources or optical filters. Similarly, aryl/heteroaryl substituents in the dipyrromethenboron difluoride cause the maximum of absorbance/emission to shift into longer wavelengths (See U.S. Pat. No. 5,451,663 hereby incorporated by reference).

A variety of BODIPY molecules are commercially available in an amine reactive form which can be used to derivitize aminoacylated tRNAs to yield a misaminoacylated tRNA with a BODIPY marker moiety. One example of a compound from this family which exhibits superior properties for incorporation of a detectable marker into nascent proteins is 4,4-difluoro-5,7-dimethyl-4-bora-3a,4a-diaza-s-indacene (BODIPY-FL). When the sulfonated N-hydroxysuccinimide (NHS) derivative of BODIPY-FL is used to misaminoacylate an E. coli initiator tRNA$^{fmet}$, the nascent protein produced can be easily detected on polyacyrlamide gels after electrophoresis using a standard UV-transilluminator and photographic or CCD imaging system. This can be accomplished by using purified tRNA$^{fmet}$ which is first aminoacylated with methionine and then the α-amino group of methionine is specifically modified using N-hydroxysuccinimide BODIPY. Before the modification reaction, the tRNA$^{fmet}$ is charged maximally (>90%) and confirmed by using $^{35}$S-methionine and acid-urea gels [Varshney, U., Lee, C. P., and RajBhandary, U. L. 1991. Direct analysis of aminoacylation levels of tRNA in vitro. J. Biol. Chem. 266:24712–24718].

Less than 10 nanoliters of a commercially available E.coli extract (E. coli T7 translation system, Promega, Madison, Wis.) are needed for analysis corresponding to less than 1 ng of synthesized protein. Incubation times required to produce detectable protein is approximately 1 hour but can be as little as 5 minutes. BODIPY-FL can also be detected with higher sensitivity using commercially available fluorescent scanners with 488 nm excitation and emission measurement above 520 mn. Similar tests using other commercially available dyes including NBD (7-Nitrobenz-2-Oxa-1,3-Diazole), and Pyrine-PyMPO show approximately an order of magnitude reduction in fluorescence making them difficult to detect using standard laboratory equipment such as a UV-transilluminator or fluorescent scanner. It has previously been shown that fluorescent markers such as 3-N-(7-nitrobenz-2-oxa-1,3-diazol-4-yl)-2,3,-diaminoproprionic acid (NBD-DAP) and coumarin could be incorporated into proteins using misaminoacylated tRNAs. However, detection of nascent proteins containing these markers was only demonstrated using highly sensitive instrumentation such a fluorescent spectrometer or a microspectrofluorimeter and often require indirect methods such as the use of fluorescence resonance energy transfer (FRET) (Turcatti, G., Nemeth, K., Edgerton, M. D., Meseth, U., Talabot, F., Peitsch, M., Knowles, J., Vogel, H., and Chollet, A. (1996)J Biol Chem 271(33), 19991–8; Kudlicki, W., Odom, O. W., Kramer, G., and Hardesty, B. (1994) J Mol Biol 244(3), 319–31). Such instruments are generally not available for routine use in a molecular biology laboratory and only with special adaptation can be equipped for measurement of fluorescent bands on a gel.

An additional advantage of BODIPY-FL as a marker is the availability of monoclonal antibodies directed against it which can be used to affinity purify nascent proteins containing said marker. One example of such a monoclonal antibody is anti-BODIPY-FL antibody (Cat# A-5770, Molecular Probes, Eugene, Oreg.). This combined with the ability incorporate BODIPY-FL into nascent proteins with high efficiency relative to other commercially available markers using misaminoacylated tRNAs facilitates more efficient isolation of the nascent protein. These antibodies against BODIPY-FL can be used for quantitation of incorporation of the BODIPY into the nascent protein.

A marker can also be modified after the tRNA molecule is aminoacylated or misaminoacylated using chemical reactions which specifically modify the marker without significantly altering the functional activity of the aminoacylated tRNA. These types of post-aminoacylation modifications may facilitate detection, isolation or purification, and can sometimes be used where the modification allow the nascent protein to attain a native or more functional configuration.

Fluorescent and other markers have detectable electromagnetic spectral properties that can be detected by spectrometers and distinguished from the electromagnetic spectral properties of native amino acids. Spectrometers which are most useful include fluorescence, Raman, absorption, electron spin resonance, visible, infrared and ultraviolet spectrometers. Other markers, such as markers with distinct electrical properties can be detected by an apparatus such as an ammeter, voltmeter or other spectrometer. Physical properties of markers which relate to the distinctive interaction of the marker with an electromagnetic field is readily detectable using instruments such as fluorescence, Raman, absorption, electron spin resonance spectrometers. Markers may also undergo a chemical, biochemical, electrochemical or photochemical reaction such as a color change in response to external forces or agents such as an electromagnetic field or reactant molecules which allows its detection.

One class of fluorescent markers contemplated by the present invention is the class of small peptides that can specifically bind to molecules which, upon binding, are detectable. One example of this approach is the peptide having the sequence of WEAAAREACCRECCARA SEQ ID NO: 4. This sequence (which contains four cysteine residues) allows the peptide to specifically bind the non-fluorescent dye molecule 4', 5'-bis(1,3,2-dithioarsolan-2-yl) fluorescein (FLASH, which stands for fluorescein arsenic helix binder). This dye has the interesting property that, upon binding, it becomes fluorescent. In other words, fluorescence is observed only when this specific peptide sequence is present in the nascent protein. So by putting the peptide sequence at the N- or C-terminal, one can easily monitor the amount of protein synthesized. This peptide sequence can be introduced by designing the nucleic acid primers such that they carry a region encoding the peptide sequence.

Regardless of which class of fluorescent compounds is used, detection normally first involves physical separation of the nascent proteins from other biomolecules present in the cellular or cell-free protein synthesis system. Protein separation can be performed using, for example, gel electrophoresis or column chromatography and can be further facilitated with affinity markers which uniquely bind acceptor groups. Detection of a marker containing a fluorophore by gel electrophoresis can be accomplished using conventional fluorescence detection methods.

After protein synthesis in a cell-free system, the reaction mixture, which contains all of the biomolecules necessary for protein synthesis as well as nascent proteins, is loaded onto a gel which may be composed of polyacrylamide or agarose (R. C. Allen et al., *Gel Electrophoresis and Isoelectric Focusing of Proteins,* Walter de Gruyter, New York 1984). This mixture also contains the misaminoacylated tRNAs bearing the marker as well as uncharged tRNAs. Subsequent to loading the reaction mixture, a voltage is applied which spatially separates the proteins on the gel in the direction of the applied electric field. The proteins separate and appear as a set of discrete or overlapping bands which can be visualized using a pre- or post-gel staining technique such as Coomasie blue staining. The migration of the protein band on the gel is a function of the molecular weight of the protein with increasing distance from the loading position being a function of decreasing molecular weight. Bands on the gel which contain nascent proteins will exhibit fluorescence when excited at a suitable wavelength. These bands can be detected visually, photographically or spectroscopically and, if desired, the nascent proteins purified from gel sections.

For example, if BODIPY-FL is used as a marker, nascent proteins will fluoresce at 510 nm when excited by UV illumination. This fluorescence can be detected visually by simply using a standard hand-held UV illuminator or a transilluminator. Approximately 10 nanograms (ng) of the protein alpha-hemolysin is detectable using this method. Also useful are electronic imaging devices which can rapidly screen and identify very low concentrations of markers such as a fluorescent scanner based on a low-temperature CCD imager. In this case as low as 0.3 ng of protein can be detected.

The molecular weight and quantity of the nascent protein can be determined by comparison of its band-position on the gel with a set of bands of proteins of predetermined molecular weight which are fluorescently labeled. For example, a nascent protein of molecular weight 25,000 could be determined because of its relative position on the gel relative to a calibration gel containing the commercially available standard marker proteins of known quantities and with known molecular weights (bovine serum albumin, 66 kD; porcine heart fumarase, 48.5 kD; carbonic anhydrase, 29 kD, β-lactoglobulin, 18.4 kD; α-lactoglobulin, 14.2 kD; Sigma Chemical; St. Louis, Mo.).

Calibration proteins may also contain a similar markers for convenient detection using the same method as the gel bearing the nascent protein. This can be accomplished in many cases by directly reacting the calibration proteins with a molecule similar to the marker. For example, the calibration proteins can be modified with dansyl chloride so as to obtain their fluorescent derivatives (R. E. Stephens, Anal. Biochem. 65, 369–79, 1975). Alternatively, the proteins could be labeled with an NHS derivitive of BODIPY-FL. These fluorescent proteins can be analyzed using PAGE. Combined detection of these fluorescent calibration proteins along with that of nascent protein which contains fluorescent marker analog will accurately determine both the molecular weight and quantity of the nascent protein synthesized. If necessary, the amounts of marker within each calibration and nascent protein can be determined to provide an accurate quantitation. Proteins with predetermined levels of fluorescent markers can be used advantageously to provide for quantitation of the gel bearing the nascent protein. This could be accomplished by genetically engineering a calibration protein so that it contains a specific reactive residue such as cysteine so that only one fluorescent dye will be attached per protein.

Other methods of protein separation are also useful for detection and subsequent isolation and purification of nascent proteins containing markers. For example, proteins can be separated using capillary electrophoresis, isoelectric focusing, low pressure chromatography and high-performance or fast-pressure liquid chromatography (HPLC or FPLC). In these cases, the individual proteins are separated into fractions which can be individually analyzed by fluorescent detectors at the emission wavelengths of the markers. Alternatively, on-line fluorescence detection can be used to detect nascent proteins as they emerge from the column fractionation system. A graph of fluorescence as a function of retention time provides information on both the quantity and purity of nascent proteins produced.

Another embodiment of the invention is directed to a method for labeling, detecting and, if desired, isolating and purifying nascent proteins, as described above, containing cleavable markers. Cleavable markers comprise a chemical structure which is sensitive to external effects such as physical or enzymatic treatments, chemical or thermal treatments, electromagnetic radiation such as gamma rays, x-rays, ultraviolet light, visible light, infrared light, microwaves, radio waves or electric fields. The marker is aminoacylated to tRNA molecules as before using conventional technology or misaminoacylated and added to a translation system. After incubation and production of nascent proteins, marker can be cleaved by the application of specified treatments and nascent proteins detected. Alternatively, nascent proteins may also be detected and isolated by the presence or absence of the cleaved marker or the chemical moiety removed from the marker.

Figure 6A:
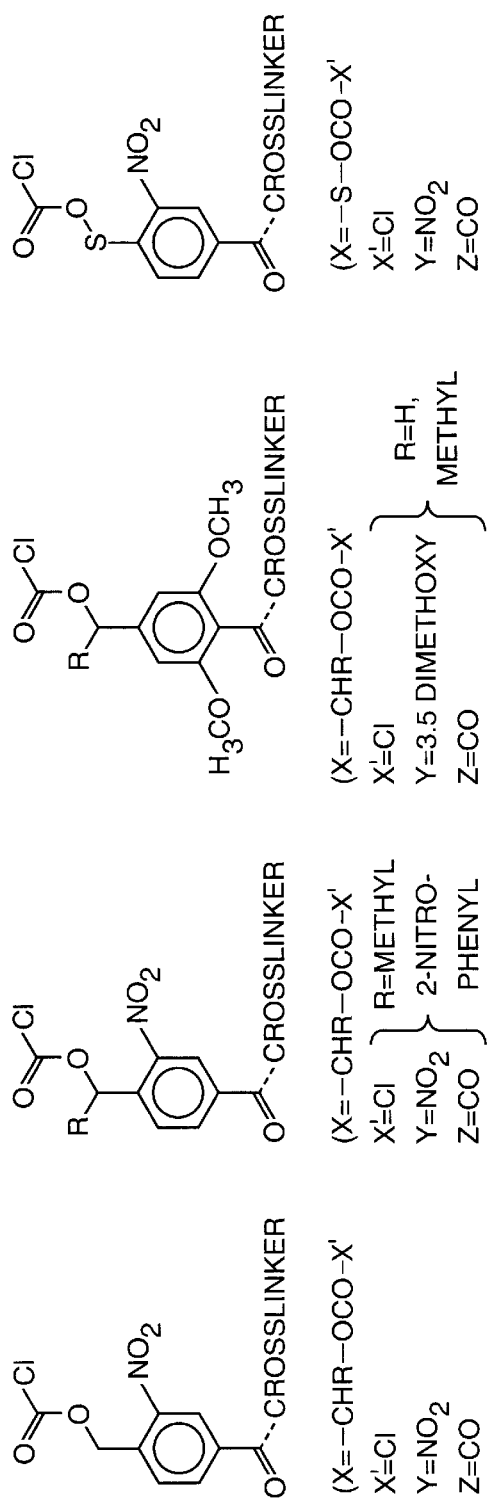
FIG. 6(A) shows chemical compounds containing the 2-nitrobenzyl moiety.
Figure 6B:
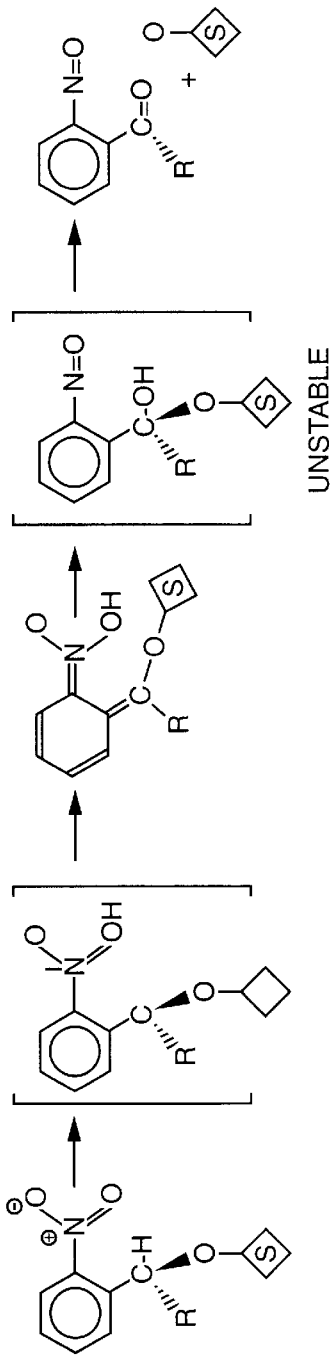
FIG. 6(B) shows cleavage of substrate from a nitrobenzyl linkage.

One example of a cleavable marker is a photocleavable marker such as chemical compounds which contain the 2-nitrobenzyl moiety (FIG. 6A). Upon illumination, these aromatic nitro compounds undergo an internal oxidation-reduction reaction (Pillai, Synthesis 1–26, 1980; Patchornik et al., *J. Am. Chem. Soc.* 92:6333–35, 1970). As a result, the nitro group is reduced to a nitroso group and an oxygen is inserted into the benzylic carbon-hydrogen bond at the ortho position. The primary photochemical process is the intramolecular hydrogen abstraction by the excited nitro group. This is followed by an electron-redistribution process to the aci-nitro form which rearranges to the nitroso product. Subsequent thermal reaction leads to the cleavage of substrate from the nitrobenzyl linkage (FIG. 6B). Examples of other cleavable markers are shown in FIG. 7.

It may sometimes be desirable to create a distance between the substrate and the cleavable moiety. To accomplish this, cleavable moieties may be separated from substrates by cross-linker arms. Cross-linkers increase substrate access and stabilize the chemical structure, and can be constructed using, for example, long alkyl chains or multiple repeat units of caproyl moieties linked via amide linkages.

There are as many methods to synthesize cleavable markers as there are different markers. One example for the synthesis of photocleavable biotins based on nitrobenzyl alcohols involves four major steps. 2-bromo-2'-nitroacetphenone, a precursor of the photoreactive moiety, is first converted into an α- or ω-amino acid like ε-aminocaprylic acid. The resulting acid and amino functionality of the photoreactive group is coupled using dicyclohexyl carbodiimide (DCC). The benzoyl carbonyl group of the resulting amide is reduced using sodium borohydride. The resulting derivative of nitrobenzyl alcohol is derivatized to obtain the final component which is able to react with biomolecular substrates, for example by the reaction with phosgene gas, to introduce the chloroformate functionality. The resulting compound is depicted in FIG. 8A along with alternative derivatives of PCB. Possible linkages to amino acids are depicted in FIG. 8B.

Cleavable markers can facilitate the isolation of nascent proteins. For example, one type of a cleavable marker is photocleavable biotin coupled to an amino acid. This marker can be incorporated into nascent proteins and the proteins purified by the specific interaction of biotin with avidin or streptavidin. Upon isolation and subsequent purification, the biotin is removed by application of electromagnetic radiation and nascent proteins utilized in useful applications without the complications of an attached biotin molecule. Other examples of cleavable markers include photocleavable coumarin, photocleavable dansyl, photocleavable dinitrophenyl and photocleavable coumarin-biotin. Photocleavable markers are cleaved by electromagnetic radiation such as UV light, peptidyl markers are cleaved by enzymatic treatments, and pyrenyl fluorophores linked by disulfide bonds are cleaved by exposure to certain chemical treatments such as thiol reagents.

Cleavage of photocleavable markers is dependent on the structure of the photoreactive moiety and the wavelength of electromagnetic radiation used for illumination. Other wavelengths of electromagnetic radiation should not damage the proteins or other chemical moieties. In the case of unsubstituted 2-nitrobenzyl derivatives, the yield of photolysis and recovery of the substrate are significantly decreased by the formation of side products which act as internal light filters and are capable to react with amino groups of the substrate. Typical illumination times vary from 1 to about 24 hours and yields are 1–95%. Radiation sources are placed within about 10 cm of the substrate proteins and set on low power so as to minimize side reactions, if any, which may occur in the nascent proteins. In the case of alpha-substituted 2-nitrobenzyl derivatives (methyl, phenyl, etc.), a considerable increase in rate of photo-removal as well as yield of the released substrate are observed. The introduction of other electron donor groups into phenyl rings of photoreactive moieties increases the yield of substrate. The general reaction for the photolysis of PCB is depicted in FIG. 9.

For enzymatic cleavage, markers introduced contain specific bonds which are sensitive to unique enzymes of chemical substances. Introduction of the enzyme or chemical into the protein mixture cleaves the marker from the nascent protein. When the marker is a modified amino acid, this can result in the production of native protein forms. Thermal treatments of, for example, heat sensitive chemical moieties operate in the same fashion. Mild application of thermal energy, such as with microwaves or radiant heat, cleaves the sensitive marker from the protein without producing any significant damage to the nascent proteins.

DESCRIPTION OF PREFERRED EMBODIMENTS

A. Detection of Mutations

Detection of mutations is an increasingly important area in clinical diagnosis, including but not limited to the diagnosis of cancer and/or individuals disposed to cancer. The protein truncation test (PTT) is a technique for the detection of nonsense and frameshift mutations which lead to the generation of truncated protein products. Genes associated with Duchenne muscular dystrophy, adenomatous polyposis coli, human mutL homologue and human nutS homologue (both involved in colon cancer), and BRAC1 (involved in familial breast cancer) can now be screened for mutations in this manner, along with others (see Table 1).

Typically, the PTT technique involves the incorpoation of a T7 promoter site, ribosome binding site, and an artificial methionine start site into a PCR product covering the region of the gene to be investigated. The PCR product is then transcribed and translated using either an in vitro rabbit reticulocyte lysate or wheat germ lysate system, to generate a protein corresponding to the region of the gene amplified. The presence of a stop codon in the sequence, generated by a nonsense mutation or a frameshift, will result in the premature termination of protein translation, producing a truncated protein that can be detected by standard gel electrophoresis (e.g. SDS-PAGE) analysis combined with radioactive dection.

There are drawbacks to the technique as currently practiced. One of the most important problems involves the identification of the product of interest. This is made difficult because of nonspecific radiolabeled products. Attempts to address these problems have been made. One approach is to introduce an affinity tag after the start site and before the region encoding the gene of interest. See Rowan and Bodmer, "Introduction of a myc Reporter Tag to Improve the Quality of Mutation Detection Using the Protein Truncation Test," *Human Mutation* 9:172 (1997). However, such approaches still have the disadvantage that they rely on electrophoresis.

TABLE 1

Applications of PTT in Human Molecular Genetics

| Disease References | % Truncating Mutations | Gene |
|---|---|---|
| Familial Adenomatous Polyposis | 95% | APC |
| Hereditary desmold disease | 100% | APC |
| Ataxia telangiectasia | 90% | ATM |
| Hereditary Breast and Ovarian Cancer | 90% | BRCA1 |
|  | 90% | BRCA2 |
| Cystic Fibrosis | 15% | CFTR |
| Duchenne Muscular Dystrophy | 95% | DMD |
| Emery-Dreifuss Muscular Dystrophy | 80% | EMD |
| Fanconi anaemia | 80% | FAA |
| Hunter Syndrome | ~50% | IDS |
| Hereditary non-polyposis colorectal cancer | ~80% | hMSH2 |
|  | ~70% | hMLH1 |
| Neurofibromatosis type 1 | 50% | NF1 |
| Neurofibromatosis type 2 | 65% | NF2 |
| Polycystic Kidney Disease | 95% | PKD1 |
| Rubinstein-Taybi Syndrome | 10% | RTS |

The percentage of truncating mutations reported which should be detectable using PTT.

The present invention contemplates a gel-free truncation test (GFTT), wherein two or three markers are introduced into the nascent protein. The present invention contemplates both pre-natal and post-natal testing to determine predisposition to disease. In a preferred embodiment of the invention, the novel compositions and methods are directed to the detection of frameshift or chain terminating mutations. In order to detect such mutations, a nascent protein is first synthesized in a cell-free or cellular translation system from message RNA or DNA coding for the protein which may contain a possible mutation. The nascent protein is then separated from the cell-free or cellular translation system using an affinity marker located at or close to the N-terminal end of the protein. The protein is then analyzed for the presence of a detectable marker located at or close to the N-terminal of the protein (N-terminal marker). A separate measurement is then made on a sequence dependent detectable marker located at or close to the C-terminal end of the protein (C-terminal marker).

A comparison of the measurements from the C-terminal marker and N-terminal marker provides information about the fraction of nascent proteins containing frameshift or chain terminating mutations in the gene sequence coding for the nascent protein. The level of sequence dependent marker located near the C-terminal end reflects the fraction of protein which did not contain chain terminating or out-of-frame mutations. The measurement of the N-terminal marker provides an internal control to which measurement of the C-terminal marker is normalized. Normalizing the level of the C-terminal marker to the N-terminal marker eliminates the inherent variabilities such as changes in the level of protein expression during translation that can undermine experimental accuracy. Separating the protein from the translation mixture using an affinity marker located at or close to the N-terminal end of the protein eliminates the occurrence of false starts which can occur when the protein is initiated during translation from an internal AUG in the coding region of the message. A false start can lead to erroneous results since it can occurs after the chain terminating or out-of-frame mutation. This is especially true if the internal AUG is in-frame with the message. In this case, the peptide C-terminal marker will still be present even if message contains a mutation.

In one example, a detectable marker comprising a non-native amino acid or amino acid derivative is incorporated into the nascent protein during its translation at the amino terminal (N-terminal end) using a misaminoacylate initiator tRNA which only recognizes the AUG start codon signaling the initiation of protein synthesis. One example of a detectable marker is the highly fluorescent compound BODIPY FL. The marker might also be photocleavable such as photocleavable coumarin or photocleavable biotin. The nascent protein is then separated from the cell-free or cellular translation system by using a coupling agent which binds to an affinity marker located adjacent to the N-terminal of the protein. One such affinity marker is a specific protein sequence known as an epitope. An epitope has the property that it selectively interacts with molecules and/or materials containing acceptor groups. There are many epitope sequences reported in the literature including HisX6 (HHHHHH) SEQ ID NO: 5 described by ClonTech and C-myc (-EQKLISEEDL) SEQ ID NO: 6 described by Roche-BM, Flag (DYKDDDDK) SEQ ID NO: 7 described by Stratagene), SteptTag (WSHPQFEK) SEQ ID NO: 8 described by Sigma-Genosys and HA Tag (YPYDVPDYA) SEQ ID NO: 9 described by Roche-BM.

Once the nascent protein is isolated from the translation system, it is analyzed for presence of the detectable marker incorporated at the N-terminal of the protein. In the case of BODIPY FL, it can be detected by measuring the level of fluorescence using a variety of commercially available instrument such as a Molecular Dynamics Model 595 fluorscence scanner that is equipped with excitation at 488 nm and an emission filter that allows light above 520 nm to be transmitted to the detector.

The protein is then analyzed for the presence of a sequence specific marker located near the C-terminal end of the protein. In normal practice, such a sequence specific marker will consist of a specific sequence of amino acids located near the C-terminal end of the protein which is recognized by a coupling agent. For example, an antibody can be utilized which is directed against an amino acid sequence located at or near C-terminal end of the nascent protein can be utilized. Such antibodies can be labeled with a variety of markers including fluorscent dyes that can be easily detected and enzymes which catalzye detectable reactions that lead to easily detectable substrates. The marker chosen should have a different detectable property than that used for the N-terminal marker. An amino acid sequence can also comprise an epitope which is recognized by coupling agents other than antibodies. One such sequence is 6 histidines sometimes referred to as a his-tag which binds to cobalt complex coupling agent.

A variety of N-terminal markers, affinity markers and C-terminal markers are available which can be used for this embodiment. The N-terminal marker could be BODIPY, affinity marker could be StrepTag and C-terminal marker could be a HisX6 tag. In this case, after translation, the reaction mixture is incubated in streptavidin coated microtiter plate or with streptavidin coated beads. After washing unbound material, the N-terminal marker is directly measured using a fluorescence scanner while the C-terminal marker can be quantitated using anti-hisX6 antibodies conjugated with a fluorescent dye (like rhodamine or Texas Red) which has optical properties different than BODIPY, thus facilitating simultaneous dual detection.

In a different example, the N-terminal marker could be a biotin or photocleavable biotin incorporated by a misaminoacylated tRNA, the affinity marker could be a His X6 tag and the C-terminal had C-myc marker. In this case, after the translation, the reaction mixture is incubated with metal chelating beads or microtiter plates (for example Talon, ClonTech). After washing the unbound proteins, the plates or beads can be subjected to detection reaction using streptavidine conjugated fluorescence dye and C-myc antibody conjugated with other fluorescent dye. In addition, one can also use chemiluminescent detection method using antibodies which are conjugated with peroxidases.

It will be understood by those skilled in the area of molecular biology and biochemistry that the N-terminal marker, affinity marker and C-terminal marker can all consist of epitopes that can be incorporated into the nascent protein by designing the message or DNA coding for the nascent protein to have a nucleic acid sequence corresponding to the particular epitope. This can be accomplished using known methods such as the design of primers that incorporate the desired nucleic acid sequence into the DNA coding for the nascent protein using the polymerase chain reaction (PCR). It will be understood by those skilled in protein biochemistry that a wide variety of detection methods are available that can be used to detect both the N-terminal marker and the C-terminal markers. Additional examples include the use of chemiluminescence assays where an enzyme which converts a non-chemiluminescent substrate to a chemiluminescent product is conjugated to an antibody that is directed against a particular epitope.

One example of this approach is based on using a luminometer to measure luminenscent markers. A biotin detectable marker is incorporated at the N-terminal using a misaminoacylated tRNA. The biotin is detected by using a streptavidin which is conjugated to Renilla luciferase from sea pansy. The C-terminal sequence comprises an epitope which interacts with a binding agent that has attached firefly luciferase. After separation of the nascent protein using a distinct epitope located near the N-terminal end of the protein, the protein is subjected to a dual luminescent luciferase assay based on a procedure described by Promega Corp and known as the Dual-Luciferase® Reporter Assay. This assay consists of first adding Luciferase Assay Reagent II available from Promega Corp. to the isolated nascent protein and then measuring the level of chemiluminesence. Stop & Glo® Reagent is then added which simultaneously quenches the firefly luminescence and activates the Renilla luminescence. The luciferase assay can be performed and quantified in seconds. A comparison of the level of luminescence measured from the firefly and Renilla luciferase provides an indication of whether a mutation is present or not in the coding message of the nascent protein.

In an additional example, the N-terminal marker comprises an affinity marker which is incorporated at the N-terminal end of the protein during its translation using a misaminoacylated tRNA. The affinity marker interacts with a coupling agent which acts to separate the nascent protein from the translation mixture. The nascent protein also contains a detectable marker which is located adjacent or close to the N-terminal of the protein containing the affinity marker. In addition, it contains a sequence specific marker at or near the C-terminal end of the protein. The detectable markers near the N-terminal and C-terminal ends of the nascent protein are then measured and compared to detect the presence of chain terminating or out-of-frame mutations.

There are a variety of additional affinity markers, N-terminal markers and C-terminal markers available for this embodiment. The affinity marker could be biotin or photocleavable biotin, N-terminal marker could be StepTag and C-terminal the C-myc epitope. In this case, after the translation, the reaction mixture is incubated with streptavidin coated beads or microtiter plates coated with streptavidin. After washing the unbound proteins, the plates or beads can be subjected to detection reaction using anti-his 6 antibodies conjugated with a fluorescent dye (like rhodamine or Texas Red) and C-myc antibody conjugated with other another fluorescent dye such as BODIPY. In addition, one can also use chemiluminescent detection method using antibodies which are conjugated with peroxidases. Even in case of peroxidases conjugated antibodies, one can use fluorescent substrates and use FluorImager like device to quantitate N-terminal and C-terminal labels.

For optimal effectiveness, the N-terminal marker and affinity marker should be placed as close as possible to the N-terminal end of the protein. For example, if an N-terminal marker is incorporated using a misaminoacylated initiator, it will be located at the N-terminal amino acid. In this case, the affinity marker should be located immediately adjacent to the N-terminal marker. Thus, if a BODIPY marker which consists of a BODIPY conjugated to methionine is incorporated by a misaminoacylated initiator tRNA, it should be followed by an epitope sequence such as SteptTag (WSHPQFEK) SEQ ID NO: 8 so that the entire N-terminal sequence will be BODIPY-MWSPQFEK SEQ ID NO: 10. However, for specific cases it may be advantageous to add intervening amino acids between the BODIPY-M and the epitope sequence in order to avoid interaction between the N-terminal marker and the affinity marker or the coupling agent which binds the affinity marker. Such interactions will vary depending on the nature of the N-terminal marker, affinity marker and coupling agent.

For optimal effectiveness, the C-terminal marker should be placed as close as possible to the C-terminal end of protein. For example, if a His-X6 tag is utilized, the protein sequence would terminate with 6 His. In some cases, an epitope may be located several residues before the C-terminal end of the protein in order to optimize the properties of the nascent protein. This might occur for example, if a specific amino acid sequence is necessary in order to modify specific properties of the nascent protein that are desirable such as its solubility or hydrophobicity.

In the normal application of this method, the ratio of the measured level of N-terminal and C-terminal markers for a nascent protein translated from a normal message can be used to calculate a standard normalized ratio. In the case of a message which may contain a mutations, deviations from this standard ratio can then be used to predict the extent of mutations. For example, where all messages are defective, the ratio of the C-terminal marker to the N-terminal marker is expected to be zero. On the other hand, in the case where all messages are normal, the ratio is expected to be 1. In the case where only half of the message is defective, for example for a patient which is heterozygote for a particular genetic defect which is chain terminating or causes an out-of-frame reading error, the ratio would be 1/2.

There are several unique advantages of this method compared to existing techniques for detecting chain terminating or out-of-frame mutations. Normally, such mutations are detected by analyzing the entire sequence of the suspect gene using conventional DNA sequencing methods. However, such methods are time consuming, expensive and not suitable for rapid throughput assays of large number of samples. An alternative method is to utilize gel electrophoresis, which is able to detect changes from the expected size of a nascent protein. This approach, sometimes referred to as the protein truncation test, can be facilitated by using non-radioactive labeling methods such as the incorporation of detectable markers with misaminoacylated tRNAs. However, in many situations, such as high throughput screening, it would be desirable to avoid the use of gel electrophoresis which is time-consuming (typically 60–90 minutes). In the present method, the need for performing gel electrophoresis is eliminated. Furthermore, since the approach depends on comparison of two detectable signals from the isolated nascent protein which can be fluorscent, luminescent or some combination thereof, it is highly amenable to automation.

Measuring a sequence dependent marker located near the C-terminal end of the protein provides information about the presence of either a frameshift or chain terminating mutation since the presence of either would result in an incorrect sequence. The measurement of the N-terminal marker provides an internal control to which measurement of the C-terminal marker is normalized. Normalizing the level of the C-terminal marker to the N-terminal marker eliminates the inherent variabilities such as changes in the level of protein expression during translation that can undermine experimental accuracy. Separating the protein from the translation mixture using an affinity marker located at or close to the N-terminal end of the protein eliminates the occurrence of false starts which can occur when the protein is initiated during translation from an internal AUG in the coding region of the message. A false start can lead to erroneous results since it can occur after the chain terminating or out-of-frame mutation. This is especially true if the internal AUG is in-frame with the message. In this case, the peptide C-terminal marker will still be present even if message contains a mutation.

B. Reporter Groups

Another embodiment of the invention is directed to a method for monitoring the synthesis of nascent proteins in a cellular or a cell-free protein synthesis system without separating the components of the system. These markers have the property that once incorporated into the nascent protein they are distinguishable from markers free in solution or linked to a tRNA. This type of marker, also called a reporter, provides a means to detect and quantitate the synthesis of nascent proteins directly in the cellular or cell-free translation system.

One type of reporters previously described in U.S. Pat. No. 5,643,722 (hereby incorporated by reference) has the characteristic that once incorporated into the nascent protein by the protein synthesizing system, they undergo a change in at least one of their physical or physio-chemical properties.

The resulting nascent protein can be uniquely detected inside the synthesis system in real time without the need to separate or partially purify the protein synthesis system into its component parts. This type of marker provides a convenient non-radioactive method to monitor the production of nascent proteins without the necessity of first separating them from pre-existing proteins in the protein synthesis system. A reporter marker would also provide a means to detect and distinguish between different nascent proteins produced at different times during protein synthesis by addition of markers whose properties are distinguishable from each other, at different times during protein expression. This would provide a means of studying differential gene expression.

One example of the utilization of reporters is schematically represented in FIG. 10. A tRNA molecule is misaminoacylated with a reporter (R) which has lower or no fluorescence at a particular wavelength for monitoring and excitation. The misaminoacylated tRNA is then introduced into a cellular or cell-free protein synthesis system and the nascent proteins containing the reporter analog are gradually produced. Upon incorporation of the reporter into the nascent protein (R*), it exhibits an increased fluorescence at known wavelengths. The gradual production of the nascent protein is monitored by detecting the increase of fluorescence at that specific wavelength.

The chemical synthesis of a reporter can be based on the linkage of a chemical moiety or a molecular component having reporter properties with a native amino acid residue. There are many fluorescent molecules which are sensitive to their environment and undergo a change in the wavelength of emitted light and yield of fluorescence. When these chemical moieties, coupled to amino acids, are incorporated into the synthesized protein, their environments are altered because of a difference between the bulk aqueous medium and the interior of a protein which can causes reduced accessibility to water, exposure to charged ionic groups, reduced mobility, and altered dielectric constant of the surrounding medium. Two such examples are shown in FIG. 11.

One example of a reporter molecule is based on a fluorescent acridinium moiety and has the unique property of altering its emission properties, depending upon polarity or viscosity of the microenvironment. It has a higher quantum yield of fluorescence when subjected to hydrophobic environment and/or viscosity. Due to the hydrophobicity of the reporter itself, it is more likely to be associated with the hydrophobic core of the nascent protein after incorporation into the growing nascent polypeptide. An increase in the fluorescence intensity is a direct measure of protein synthesis activity of the translation system. Although, the environment of each reporter residue in the protein will be different, and in some cases, the reporter may be present on the surface of the protein and exposed to an aqueous medium, a net change occurs in the overall spectroscopic properties of the reporters incorporated into the protein relative to bulk aqueous medium. A change in the spectroscopic properties of only a subset of reporters in the protein will be sufficient to detect the synthesis of proteins that incorporate such reporters.

An alternative approach is to utilize a reporter which alters its fluorescent properties upon formation of a peptide bond and not necessarily in response to changes in its environment. Changes in the reporter's fluorescence as it partitions between different environments in the cell-free extract does not produce a large signal change compared to changes in fluorescence upon incorporation of the reporter into the nascent protein.

A second example of a reporter is a marker based on coumarin such as 6,7-(4', 5'-prolino)coumarin. This compound can be chemically synthesized by coupling a fluorophore like coumarin with an amino-acid structural element in such a way that the fluorophore would alter its emission or absorption properties after forming a peptide linkage (FIG. 11). For example, a proline ring containing secondary amino functions will participate in peptide bond formation similar to a normal primary amino group. Changes in fluorescence occur due to the co-planarity of the newly formed peptide group in relation to the existing fluorophore. This increases conjugation/delocalization due to the π-electrons of nitrogen-lone pair and carbonyl-group in the peptide bond. Synthesis of such compounds is based on on coumarin synthesis using ethylacetoacetate (FIG. 11).

Reporters are not limited to those non-native amino acids which change their fluorescence properties when incorporated into a protein. These can also be synthesized from molecules that undergo a change in other electromagnetic or spectroscopic properties including changes in specific absorption bands in the UV, visible and infrared regions of the electromagnetic spectrum, chromophores which arc Raman active and can be enhanced by resonance Raman spectroscopy, electron spin resonance activity and nuclear magnetic resonances. In general, a reporter can be formed from molecular components which undergo a change in their interaction and response to electromagnetic fields and radiation after incorporation into the nascent protein.

In the present invention, reporters may also undergo a change in at least one of their physical or physio-chemical properties due to their interaction with other markers or agents which are incorporated into the same nascent protein or are present in the reaction chamber in which the protein is expressed. The interaction of two different markers with each other causes them to become specifically detectable. One type of interaction would be a resonant energy transfer which occurs when two markers are within a distance of between about 1 angstrom (A) to about 50 A, and preferably less than about 10 A. In this case, excitation of one marker with electromagnetic radiation causes the second marker to emit electromagnetic radiation of a different wavelength which is detectable. A second type of interaction would be based on electron transfer between the two different markers which can only occur when the markers are less than about 5 A. A third interaction would be a photochemical reaction between two markers which produces a new species that has detectable properties such as fluorescence. Although these markers may also be present on the misaminoacylated tRNAs used for their incorporation into nascent proteins, the interaction of the markers occurs primarily when they are incorporated into protein due to their close proximity. In certain cases, the proximity of two markers in the protein can also be enhanced by choosing tRNA species that will insert markers into positions that are close to each other in either the primary, secondary or tertiary structure of the protein. For example, a tyrosine-tRNA and a tryptophan-tRNA could be used to enhance the probability for two different markers to be near each other in a protein sequence which contains the unique neighboring pair tyrosine-tryptophan.

In one embodiment of this method, a reporter group is incorporated into a nascent protein using a misaminoacylated tRNA so that when it binds to a coupling agent, the reporter group interacts with a second markers or agents which causes them to become specifically detectable. Such an interaction can be optimized by incorporating a specific affinity element into the nascent protein so that once it interacts with a coupling agent the interaction between the reporter group and the second marker is optimized. Such an affinity element might comprise a specific amino acid sequence which forms an epitope or a nonnative amino acid. In one example, the reporter group is incorporated at the N-terminal of the nascent protein by using a misaminoacylated tRNA. The epitope is incorporated into the nascent protein so that when it interacts with the coupling agent the reporter comes into close proximity with a second marker which is conjugated to the coupling agent.

One type of interaction between the markers that is advantageously used causes a fluorescence resonant energy transfer which occurs when the two markers are within a distance of between about 1 angstrom (A) to about 50 A, and preferably less than about 10 A. In this case, excitation of one marker with electromagnetic radiation causes the second marker to emit electromagnetic radiation of a different wavelength which is detectable. This could be accomplished, for example, by incorporating a fluorescent marker at the N-terminal end of the protein using the $E.\ coli$ initiator tRNA$^{fmet}$. An epitope is then incorporated near the N-terminal end such as the SteptTag (WSHPQFEK) SEQ ID NO: 8 described by Sigma-Genosys. Streptavidin is then conjugated using known methods with a second fluorescent marker which is chosen to efficiently undergo fluorescent energy transfer with marker 1. The efficiency of this process can be determined by calculating the a Förster energy transfer radius which depends on the spectral properties of the two markers. The marker-streptavidin complex is then introduced into the translation mixture. Only when nascent protein is produced does fluorescent energy transfer between the first and second marker occur due to the specific interaction of the nascent protein StreptTag epitope with the streptavidin.

There are a variety of dyes which can be used as marker pairs in this method that will produce easily detectable signals when brought into close proximity. Previously, such dye pairs have been used for example to detect PCR products by hybridizing to probes labeled with a dye on one probe at the 5'-end and another at the 3'-end. The production of the PCR product brings a dye pair in close proximity causing a detectable FRET signal. In one appliation the dyes, fluoresein and LC 640 were utilized on two different primers (Roche Molecular Biochemicals-http://www.biochem.boehringer-mannheim.com/lightcycler/monito03.htm). When the fluorescein is excited by green light (around 500 nm) that is produced by a diode laser, the LC 640 emits red fluorescent light (around 640 nm) which can be easily detected with an appropriate filter and detector. In the case of nasent proteins, the pair of dyes BODIPY FL and LC 640 would function in a similar manner. For example, incorporation of the BODIPY FL on the N-terminal end of the protein and the labeling of a binding agent with LC 640 which is directed against an N terminal epitope would allow detection of the production of nascent proteins.

The use of the marker pair BODIPY-FL and coumarin is a second pair which can be utilized advantageously. In one study, [Keller, R. C., Silvius, J. R., and De Kruijff, B. (1995) *Biochem Biophys Res Commun* 207(2), 508–14] it was found using the spectral overlap a Förster energy transfer radius (RO) of 50+/−2 A and 40+/−2 A for the coumarin-(beta-BODIPY FL ) and the coumarin-(beta-BODIPY 530/550 ) couple respectively. Experimentally this was estimated to be 49.0–51.5 A and 38.5–42.5 A respectively. It is also possible to use two markers with similar or identical spectral properties for the marker pair due to the process of quenching. For example, in one study this process was used in the case of BODIPY FL in order to study the processing of exogenous proteins in intact cells [Reis, R. C., Sorgine, M. H., and Coelho-Sampaio, T. (1998) *Eur J Cell Biol* 75(2), 192–7] and in a second case to study the kinetics of intracellular viral assembly [Da Poian, A. T., Gomes, A. M., and Coelho-Sampaio, T. (1998) *J Virol Methods* 70(1), 45–58].

As stated above, a principal advantage of using reporters is the ability to monitor the synthesis of proteins in cellular or a cell-free translation systems directly without further purification or isolation steps. Reporter markers may also be utilized in conjunction with cleavable markers that can remove the reporter property at will. Such techniques are not available using radioactive amino acids which require an isolation step to distinguish the incorporated marker from the unincorporated marker. With in vitro translation systems, this provides a means to determine the rate of synthesis of proteins and to optimize synthesis by altering the conditions of the reaction. For example, an in vitro translation system could be optimized for protein production by monitoring the rate of production of a specific calibration protein. It also provides a dependable and accurate method for studying gene regulation in a cellular or cell-free systems.

C. Affinity Markers

Another embodiment of the invention is directed to the use of markers that facilitate the detection or separation of nascent proteins produced in a cellular or cell-free protein synthesis system. Such markers are termed affinity markers and have the property that they selectively interact with molecules and/or materials containing acceptor groups. The affinity markers are linked by aminoacylation to tRNA molecules in an identical manner as other markers of non-native amino acid analogs and derivatives and reporter-type markers as described. These affinity markers are incorporated into nascent proteins once the misaminoacylated tRNAs are introduced into a translation system.

An affinity marker facilities the separation of nascent proteins because of its selective interaction with other molecules which may be biological or non-biological in origin through a coupling agent. For example, the specific molecule to which the affinity marker interacts, referred to as the acceptor molecule, could be a small organic molecule or chemical group such as a sulfhydryl group (-SH) or a large biomolecule such as an antibody. The binding is normally chemical in nature and may involve the formation of covalent or non-covalent bonds or interactions such as ionic or hydrogen bonding. The binding molecule or moiety might be free in solution or itself bound to a surface, a polymer matrix, or a reside on the surface of a substrate. The interaction may also be triggered by an external agent such as light, temperature, pressure or the addition of a chemical or biological molecule which acts as a catalyst.

The detection and/or separation of the nascent protein and other preexisting proteins in the reaction mixture occurs because of the interaction, normally a type of binding, between the affinity marker and the acceptor molecule. Although, in some cases some incorporated affinity marker will be buried inside the interior of the nascent protein, the interaction between the affinity marker and the acceptor molecule will still occur as long as some affinity markers are exposed on the surface of the nascent protein. This is not normally a problem because the affinity marker is distributed over several locations in the protein sequence.

Affinity markers include native amino acids, non-native amino acids, amino acid derivatives or amino acid analogs in which a coupling agent is attached or incorporated. Attachment of the coupling agent to, for example, a non-native amino acid may occur through covalent interactions, although non-covalent interactions such as hydrophilic or hydrophobic interactions, hydrogen bonds, electrostatic interactions or a combination of these forces are also possible. Examples of useful coupling agents include molecules such as haptens, immunogenic molecules, biotin and biotin derivatives, and fragments and combinations of these molecules. Coupling agents enable the selective binding or attachment of newly formed nascent proteins to facilitate their detection or isolation. Coupling agents may contain antigenic sites for a specific antibody, or comprise molecules such as biotin which is known to have strong binding to acceptor groups such as streptavidin. For example, biotin may be covalently linked to an amino acid which is incorporated into a protein chain. The presence of the biotin will selectively bind only nascent proteins which incorporated such markers to avidin molecules coated onto a surface. Suitable surfaces include resins for chromatographic separation, plastics such as tissue culture surfaces for binding plates, microtiter dishes and beads, ceramics and glasses, particles including magnetic particles, polymers and other matrices. The treated surface is washed with, for example, phosphate buffered saline (PBS), to remove non-nascent proteins and other translation reagents and the nascent proteins isolated. In some case these materials may be part of biomolecular sensing devices such as optical fibers, chemfets, and plasmon detectors.

One example of an affinity marker is dansyllysine (FIG. 5). Antibodies which interact with the dansyl ring are commercially available (Sigma Chemical; St. Louis, Mo.) or can be prepared using known protocols such as described in *Antibodies: A Laboratory Manual* (E. Harlow and D. Lane, editors, Cold Spring Harbor Laboratory Press, 1988) which is hereby specifically incorporated by reference. Many conventional techniques exist which would enable proteins containing the dansyl moiety to be separated from other proteins on the basis of a specific antibody-dansyl interaction. For example, the antibody could be immobilized onto the packing material of a chromatographic column. This method, known as affinity column chromatography, accomplishes protein separation by causing the target protein to be retained on the column due to its interaction with the immobilized antibody, while other proteins pass through the column. The target protein is then released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.).

Separation can also be performed through an antibody-dansyl interaction using other biochemical separation methods such as immunoprecipitation and immobilization of the antibodies on filters or other surfaces such as beads, plates or resins. For example, protein could be isolated by coating magnetic beads with a protein-specific antibody. Beads are separated from the extract using magnetic fields. A specific advantage of using dansyllysine as an affinity marker is that once a protein is separated it can also be conveniently detected because of its fluorescent properties.

In addition to antibodies, other biological molecules exist which exhibit equally strong interaction with target molecules or chemical moieties. An example is the interaction of biotin and avidin. In this case, an affinity analog which contains the biotin moiety would be incorporated into the protein using the methods which are part of the present invention. Biotin-lysine amino acid analogs are commercially available (Molecular Probes; Eugene, Oreg.).

Affinity markers also comprise one component of a multicomponent complex which must be formed prior to detection of the marker. One particular embodiment of this detection means involves the use of luminescent metal chelates, in particular luminescent rare earth metal chelates. It is well known that certain molecules form very stable complexes with rare earth metals. It is also well known that introduction of chromophore into these chelates sensitizes luminescence of these complexes. A variety of detection schemes based on the use of luminescent rare earth metal chelates have been described: Hemmila, I. A., "Applications of Fluorescence in Immunoassays", (Wiley&Sons 1991).

In a preferred embodiment, tRNA is misaminoacylated with a chromophore that also acts as a rare earth shelter. This modified aminoacyl tRNA is then introduced into cellular or cell-free protein translation system and the modified amino acid incorporated into nascent protein. The mixture is then separated using gel electrophoresis and the gel is incubated with a solution containing rare earth cation. Under these conditions rare earth cations form luminescent complexes with amino acids modified with a chelator present only in nascent proteins. The nascent proteins are then detected using a mid-range UV transilluminator (350 nm), which excites the formed lanthanide complex. The image is then recorded using polaroid camera or CCD array and a filter. In one embodiment, the derivatives of salicylic acid as one component and terbium ions as a second component of the binary detection system are used.

Affinity markers can also comprise cleavable markers incorporating a coupling agent. This property is important in cases where removal of the coupled agent is required to preserve the native structure and function of the protein and to release nascent protein from acceptor groups. In some cases, cleavage and removal of the coupling agent results in production of a native amino acid. One such example is photocleavable biotin coupled to an amino acid.

Photocleavable biotin contains a photoreactive moiety which comprises a phenyl ring derivatized with functionalities represented in FIG. 12 by X, Y and Z. X allows linkage of PCB to the bimolecular substrate through the reactive group X'. Examples of X' include Cl, O—N-hydroxysuccinimidyl, $OCH_2CN$, $OPhF_5$, $OPhCl_5$, $N_3$. Y represents a substitution pattern of a phenyl ring containing one or more substitutions such as nitro or alkoxyl. The functionality Z represents a group that allows linkage of the cross-linker moiety to the photoreactive moiety. The photoreactive moiety has the property that upon illumination, it undergoes a photoreaction that results in cleavage of the PCB molecule from the substrate.

A lysine-tRNA is misaminoacylated with photocleavable biotin-lysine, or chemically modified to attach a photocleavable biotin amino acid. The misaminoacylated tRNA is introduced into a cell-free protein synthesizing system and nascent proteins produced. The nascent proteins can be separated from other components of the system by streptavidin-coated magnetic beads using conventional methods which rely on the interaction of beads with a magnetic field. Nascent proteins are released then from beads by irradiation with UV light of approximately 280 nm wavelength.

Many devices designed to detect proteins are based on the interaction of a target protein with specific immobilized acceptor molecule. Such devices can also be used to detect nascent proteins once they contain affinity markers such as biodetectors based on sensing changes in surface plasmons, light scattering and electronic properties of materials that are altered due to the interaction of the target molecule with the immobilized acceptor group.

Nascent proteins, including those which do not contain affinity-type markers, may be isolated by more conventional isolation techniques. Some of the more useful isolation techniques which can be applied or combined to isolate and purify nascent proteins include chemical extraction, such as phenol or chloroform extract, dialysis, precipitation such as ammonium sulfate cuts, electrophoresis, and chromatographic techniques. Chemical isolation techniques generally do not provide specific isolation of individual proteins, but are useful for removal of bulk quantities of non-proteinaceous material. Electrophoretic separation involves placing the translation mixture containing nascent proteins into wells of a gel which may be a denaturing or non-denaturing polyacrylamide or agarose gel. Direct or pulsed current is applied to the gel and the various components of the system separate according to molecular size, configuration, charge or a combination of their physical properties. Once distinguished on the gel, the portion containing the isolated proteins removed and the nascent proteins purified from the gel. Methods for the purification of protein from acrylamide and agarose gels are known and commercially available.

Chromatographic techniques which are useful for the isolation and purification of proteins include gel filtration, fast-pressure or high-pressure liquid chromatography, reverse-phase chromatography, affinity chromatography and ion exchange chromatography. These techniques are very useful for isolation and purification of proteins species containing selected markers.

Another embodiment of the invention is directed to the incorporation of non-native amino acids or amino acid derivatives with marker or affinity properties at the amino-terminal residue of a nascent protein (FIG. 13). This can be accomplished by using the side chain of an amino acid or by derivatizing the terminal amino group of an amino acid. In either case the resulting molecule is termed an amino acid derivative. The amino-terminal residue of a protein is free and its derivatization would not interfere with formation of the nascent polypeptide. The non-native amino acid or amino acid derivative is then used to misaminoacylate an initiator tRNA which only recognizes the first AUG codon signaling the initiation of protein synthesis. After introduction of this misaminoacylated initiator tRNA into a protein synthesis system, marker is incorporated only at the amino terminal of the nascent protein. The ability to incorporate at the N-terminal residue can be important as these nascent molecules are most likely to fold into native conformation. This can be useful in studies where detection or isolation of functional nascent proteins is desired.

Not all markers incorporated with misaminoacylated initiator tRNAs at the amino-terminal residue of the nascent protein show the same acceptance by the protein translational machinery. Furthermore, the range of incorporation of different markers can be more restrictive compared to the use of non-initiator tRNAs such as lysyl-tRNA. Although the factors influencing this descrimination between markers for incorporation by a misaminoacylated initiator tRNA are not fully elucidated, one possibility is that the initiation factor (IF2) which is used for carrying formylmethionine-$tRNA^{fmet}$ to ribosomes plays a role. A second possibility is that the interaction between the marker structure and the ribosomes plays a role. For example, the marker, BODIPY-FL is accepted by the protein translational machinery to a greater extent than smaller fluorescent markers such as NBD. For this reason, BODIPY-FL is a superior marker for use in the detection of nascent protein when incorporated through initiator tRNAs.

A marker group can also be incorporated at the N terminal by using a mutant tRNA which does not recognize the normal AUG start codon. In some cases this can lead to a higher extent of specific incorporation of the marker. For example, the mutant of initiator tRNA, where the anticodon has been changed from CAU→CUA (resulting in the change of initiator methionine codon to amber stop codon) has shown to act as initiator suppressor tRNA (Varshney U, RajBhandary UL, Proc Natl Acad Sci U S A February 1990;87(4):1586–90; Initiation of protein synthesis from a termination codon). This tRNA initiates the protein synthesis of a particular gene when the normal initiation codon, AUG is replaced by the amber codon UAG. Furthermore, initiation of protein synthesis with UAG and tRNA (fMet$^{CUA}$) was found to occur with glutamine and not methionine. In order to use this tRNA to introduce a marker at the N terminal of a nascent protein, this mutant tRNA can be enzymatically aminoacylated with glutamine and then modified with suitable marker. Alternatively, this tRNA could be chemically aminoacylated using modified amino acid (for example methionine-BODIPY). Since protein translation can only be initiated by this protein on messages containing UAG, all proteins will contain the marker at the N-terminal end of the protein.

D. Mass Spectrometry

Mass spectrometry measures the mass of a molecule. The use of mass spectrometry in biology is continuing to advance rapidly, finding applications in diverse areas including the analysis of carbohydrates, proteins, nucleic acids and biomolecular complexes. For example, the development of matrix assisted laser desorption ionization (MALDI) mass spectrometry (MS) has provided an important tool for the analysis of biomolecules, including proteins, oligonucleotides, and oligosacharrides [Karas, 1987 #6180; Hillenkamp, 1993 #6175]. This technique's success derives from its ability to determine the molecular weight of large biomolecules and non-covalent complexes (>500,000 Da) with high accuracy (0.01%) and sensitivity (subfemtomole quantities). Thus far, it has been found applicable in diverse areas of biology and medicine including the rapid sequencing of DNA, screening for bioactive peptides and analysis of membrane proteins.

Markers incorporated by misaminoacylated tRNAs into nascent proteins, especially at a specific position such at the N-terminal can be used for the detection of nascent proteins by mass spectrometry. Without such a marker, it can be very difficult to detect a band due to a nascent protein synthesized in the presence of a cellular or cell-free extract due the presence of many other molecules of similar mass in the extract. For example, in some cases less than 0.01% of the total protein mass of the extract may comprise the nascent protein(s). Furthermore, molecules with similar molecular weight as the nascent protein may be present in the mixture. Such molecules will overlap with peaks due to the nascent protein. This problem is particularly severe if the nascent protein is a transcription or translation factor already present in the cell-free or cellular protein synthesis. The synthesis of additional amounts of this protein in the protein synthesis system would be difficult to detect using known methods in mass spectrometry since peak intensities are not correlated in a linear manner with protein concentration.

Detection by mass spectrometry of a nascent protein produced in a translation system is also very difficult if the mass of the nascent protein produced is not known. This situation might occur for example if the nascent protein is translated from DNA where the exact sequence is not known. One such example is the translation of DNA from individuals which may have specific mutations in particular genes or gene fragments. In this case, the mutation can cause a change in the protein sequence and even result in chain truncation if the mutation results in a stop codon. The mass of nascent proteins produced in a translation system might also not be known if DNA is derived from unknown sources such as as colonies of bacteria which can contain different members of a gene library or fragments thereof.

In one embodiment of the invention, the incorporation of markers of a specific mass (mass markers) into nascent proteins can be used to eliminate all of the above mentioned problems associated with the conventional mass spectrometric approach. First, a tRNA misaminoacylated with a marker of a known mass is added to the protein synthesis system. The synthesis system is then incubated to produce the nascent proteins. The mass spectrum of the protein synthesis system is then measured. The presence of the nascent protein can be directly detected by identifying peaks in the mass spectrum of the protein synthesis system which correspond to the mass of the unmodified protein and a second band at a higher mass which corresponds to the mass of the nascent protein plus the modified amino acid containing the mass of the marker.

There are several steps that can be taken to optimize the efficient detection of nascent proteins using this method. The mass of the marker should exceed the resolution of the mass spectrometer, so that the increased in mass of the nascent protein can be resolved from the unmodified mass. For example, a marker with a mass exceeding 100 daltons can be readily detected in proteins with total mass up to 100,000 using both matrix assisted laser desorption (MALDI) or electrospray ionization (ESI) techniques. The amount of misaminoacylated tRNA should be adjusted so that the incorporation of the mass marker occurs in approximately 50% of the total nascent protein produced. An initiator tRNA is preferable for incorporation of the mass marker since it will only be incorporated at the N-terminal of the nascent protein, thus avoiding the possibility that the nascent protein will contain multiple copies of the mass marker.

One example of this method is the incorporation of the marker BODIPY-FL, which has a mass of 282, into a nascent protein using a misaminoacylated initiator tRNA. Incorporation of this marker into a nascent protein using a misaminoacylated initiator tRNA causes a band to appear at approximately 282 daltons above the normal band which appears for the nascent protein. Since the incorporation of the marker is less than one per protein due to competition of non-misaminoacylated $E.coli$ tRNA$^{fmet}$, a peak corresponding to the unmodified protein also appears. Identification of these two bands separated by the mass of the marker allows initial identification of the band due to the nascent protein. Further verification of the band due to the nascent protein can be made by adjusting the level of the misaminoacylated initiator tRNA in the translation mixture. For example, if the misaminoacylated initiator tRNA is left out, than only a peak corresponding to the unmodified protein appears in the mass spectrum of the protein synthesis system. By comparing the mass spectrum from the protein synthesis system containing and not containing the misaminacylated tRNA with the BODIPY-FL, the presence of the nascent protein can be uniquely identified, even when a protein with similar or identical mass is already present in the protein synthesis system.

For the purpose of mass spectrometric identification of nascent proteins, it is sometimes advantageous to utilize a photocleavable marker. In this case, peaks due to nascent proteins in the mass spectrum can be easily identified by measuring and comparing spectra from samples of the protein synthesis system that have been exposed and not exposed to irradiation which photocleaves the marker. Those samples which are not exposed to irradiation will exhibit bands corresponding the mass of the nascent protein which has the incorporated mass marker, whereas those samples which are exposed to irradiation will exhibit bands corresponding to the mass of the nascent proteins after removal of the mass marker. This shift of specific bands in the mass spectrum due to irradiation provides a unique identifier of bands which are due to the nascent proteins in the protein synthesis system.

One example of this method involves the use of the photocleavable marker, photocleavable biotin. When photocleavable biotin is incorporated into the test protein α-hemolysin, a toxin produced by staphyloccus, by using the misaminoacylated $E.$ $coli$ initiator tRNA$^{met}$, the mass spectrum exhibits two peaks corresponding to the mass of the nascent protein 35,904 Da, and a second peak at 36,465 Da corresponding to the mass of the nascent protein plus the mass of photocleavable biotin. After photocleavage of the marker by exposing the cell-free or cellular extract to UV light with a wavelength of approximately 365 nm for approximately 10 minutes, the two bands undergo changes in intensity due to cleavage of the marker from the nascent protein. For example, in the case of a form of photocleavable biotin containing a single spacer the change in the mass will be 561.57. These characteristic changes are then used to uniquely identify the peaks corresponding the nascent protein. In the case of MALDI mass spectrometry, the probe laser pulses when adjusted to sufficient intensity can be used to accomplish photocleavage of photocleavable biotin. In this case, changes can be conveniently measured during the course of the measurements, thereby facilitating detection of peaks associated with the nascent protein. A similar approach can also be used to identify more than one nascent protein of unknown mass in a cell or cell-free translation system.

Markers with affinity properties which are incorporated by misaminoacylated tRNAs into nascent proteins can also be very useful for the detection of such proteins by mass spectrometry. Such markers can be used to isolate nascent proteins from the rest of the cell-free or cellular translation system. In this case, the isolation of the nascent proteins from the rest of the cell-free mixture removes interference from bands due to other molecules in the protein translation system. An example of this approach is the incorporation of photocleavable biotin into the N-terminal end of a nascent proteins using misaminoacylated tRNA. When this marker is incorporated onto the N-terminal end of a nascent protein using an $E.$ $coli$ tRNA$^{met}$, it provides a convenient affinity label which can be bound using streptavidin affinity media such as streptavidin agarose. Once the nascent protein is separated by this method from the rest of the protein synthesis system, it can be released by UV-light and analyzed by mass spectrometry. In the case of MALDI mass spectrometry, release of the nascent protein can most conveniently be accomplished by using the UV-laser excitation pulses of the MALDI system. Alternatively, the sample can be irradiated prior to mass spectrometric analysis in the case of MALDI or ESI mass spectrometry.

E. Electrophoresis

Another embodiment of the invention is directed to methods for detecting by electrophoresis the interaction of molecules or agents with nascent proteins which are translated in a translation system. This method allows a large number of compounds or agents to be rapidly screened for possible interaction with the expressed protein of specific genes, even when the protein has not been isolated or its function identified. It also allows a library of proteins expressed by a pool of genes to be rapidly screened or interaction with compounds or agents without the necessity of isolating these proteins or agents. The agents might be part of a combinatorial library of compounds or present in a complex biological mixture such as a natural sample. The agents might interact with the nascent proteins by binding to them or to cause a change in the structure of the nascent protein by chemical or enzymatic modification.

In addition to gel electrophoresis, which measures the electrophoretic mobility of proteins in gels such as polyacyralimide gel, this method can be performed using capillary electrophoresis. CE measures the electrophoretic migration time of a protein which is proportional to the charge-to-mass ratio of the molecule. One form of CE, sometimes termed affinity capillary electrophoresis, has been found to be highly sensitive to interaction of proteins with other molecules including small ligands as long as the binding produces a change in the charge-to-mass ratio of the protein after the binding event. The highest sensitivity can be obtained if the protein is conjugated to a marker with a specifically detectable electromagnetic spectral property such as a fluorescent dye. Detection of a peak in the electrophoresis chromatogram is accomplished by laser induced emission of mainly visible wavelengths. Examples of fluorescent dyes include fluoroscein, rhodamine, Texas Red and BODIPY.

It is very difficult to detect a nascent protein synthesized in a cellular or cell-free extract by CE without subsequent isolation and labeling steps due to the need for high sensitivity detection and the presence of many other molecules of similar mass/charge ratio in the extract. For example, in typical cases less than 0.01% of the total protein mass of the extract may comprise the nascent protein(s). Other molecules with similar electrophoretic migration times as the nascent protein may be present in the mixture. Such molecules will overlap with peaks due to the nascent protein.

It is also very difficult using conventional methods of CE to detect the interaction of molecules with nascent proteins produced in a cell free or cellular synthesis system. Affinity capillary electrophoresis has been found to be sensitive to interaction of proteins with other molecules including small ligands as long as the binding produces a change in the charge-to-mass ratio of the protein after the binding event. However, the selective addition of a marker such as a fluorescent dye to a nascent protein is not possible using conventional means because most markers reagents will nonspecifically label other molecules in the protein synthesis system besides the nascent proteins. In some cases, it may be possible to utilize a specific substrate or ligand which binds only to the nascent protein. However this approach requires a detailed knowledge of the binding properties of the nascent protein and special design of a ligand with marker properties. The nascent protein may also be isolated from the protein synthesis system and then selectively labeled with a detectable marker. However, this also requires the development of a procedure for isolation of the nascent protein which can be time consuming and requires extensive knowledge of properties of the protein or protein engineering to incorporate an affinity epitope. Even after a nascent protein has been isolated, it is often difficult to uniformly label the protein with a marker so that the charge/mass ratio of each labeled protein remains the same. In the most advantageous form of labeling, a highly fluorescent marker is incorporated at only one specific position in the protein thus avoiding a set of proteins with different electrophoretic mobilities.

The method of the invention also overcomes major problems associated with the rapid screening of samples for new therapeutic compounds using capillary electrophoresis (CE) such as described in U.S. Pat. No. 5,783,397 (hereby incorporated by reference) when the target protein is a nascent protein expressed in a translation system. This includes the need to uniformly label expressed target proteins in a translation system with markers for high sensitivity analysis by CE which normally requires lengthy isolation steps and special techniques for uniform labeling.

The method can also be used in conjunction with expression cloning method for isolating novel cDNA clones such as described in U.S. Pat. No. 5,654,150, which is specifically incorporated by reference. This patent describes novel methods to identify cDNA clones by a) collecting pools of about 100 individual bacterial colonies; and b) expressing proteins encoded by the cDNAs in the pools in vitro. Proteins which can be identified in this manner include but are not limited to nucleic acid binding protein, cytoskeletal protein, growth factor, differentiation factor, post-translationally modified protein, phosphorylated protein, proteolytically cleaved protein, glycosylated protein, subunit or a multiple component of a protein complex, enzyme, isoform of a known protein, mutant form of known protein. Importantly, the method includes as a crucial step identifying a desired protein from a protein translation system. Two such methods described for identifying the protein involve radioactive labeling and chemical labeling. However, these steps can be extremely time-consuming and are not conducive to rapidly screening an extract for the desired protein.

The present invention avoids all of the problems discussed above. In one embodiment of the invention a tRNA misaminoacylated with a detectable marker is added to the protein synthesis system. The system is incubated to incorporate the detectable marker into the nascent proteins. One or more molecules (agents) are then combined with the nascent proteins (either before or after isolation) to allow agents to interact with nascent proteins. Aliquots of the mixture are then subjected to electrophoresis. Nascent proteins which have interacted with the agents are identified by detecting changes in the electrophoretic mobility of nascent proteins with incorporated markers. In the case where the agents have interacted with the nascent proteins, the proteins can be isolated and subsequently subjected to further analysis. In cases where the agents have bound to the nascent proteins, the bound agents can be identified by isolating the nascent proteins.

In one example of this method, the fluorescent marker BODIPY-FL is used to misaminoacylate an *E. coli* initiator tRNA$^{fmet}$ as previously described. The misaminoacylated tRNA is then added to a protein synthesis system and the system incubated to produce nascent protein containing the BODIPY-FL at the N-terminal. A specific compound which may bind to the nascent protein is then added to the protein synthesis system at a specific concentration. An aliquot from the mixture is then injected into an apparatus for capillary electrophoresis. Nascent proteins in the mixture are identified by detection of the fluorescence from the BODIPY-FL using exciting light from an Argon laser tuned to 488 nm. Interaction of the specific compound is determined by comparing the electrophoretic mobility measured of the nascent protein exposed to the specific compound with a similar measurement of the nascent protein that has not been exposed. The binding strength of the compound can then be ascertained by altering the concentration of the specific compounds added to the protein synthesis system and measuring the change in the relative intensity of bands assigned to the uncomplexed and complexed nascent protein.

The method is not limited to studying the interaction of one agent with one nascent protein translated in a protein translation system. For example, a library of compounds can be screened to identify those which serve are ligands for specific target protein. In addition to interactions which involve the binding of one or more agents to the nascent proteins interactions which result in a modification of the nascent protein including but are not limited to phosphorylation, proteolysis, glycosylation, formation of a complex with other biological molecules can be detected using the marker incorporated in the nascent proteins when combined with electrophoresis. For example, the interaction of an antibody with the nascent proteins can be detected due to a change in the effective electrophoretic mobility of the complex formed. A similar approach could be used to identify the presence of one or more compounds in a complex mixture which bind to the nascent protein. Such a mixture might constitute a library of compounds produced by combinatorial chemistry or compounds which might be present in a complex biological mixture such as natural samples which may contain therapeutic compounds.

F. Microscale Methods

While the present invention contemplates capillary electrophoresis (see above), other methods are also contemplated. In particular, microscale methods can be employed in conjunction with the novel markers (e.g. BODIPY) and methods of the present invention. The methods are "microscale" in that the dimensions of the channels on the device (and the corresponding fluid volumes) are very small (typically in the picometer range). For example, channels are typically between approximately 0.10 and 0.50 μm in depth and between approximately 5 and 500 μm in width.

Although there are many formats, materials, and size scales for constructing integrated fluidic systems, the present invention contemplates microfabricated devices as a solution to the many inefficiencies of larger scale screening. Devices can be microfabricated from a number of materials. Silicon is the material used for the construction of computing microprocessors and its fabrication technologies have developed at an unprecedented pace over the past 30 years. The principal modern method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate. See e.g., W. Miller, U.S. Pat. No. 5,091,328, hereby incorporated by reference. While this technology was initially applied to making microelectronic devices, the same techniques are currently being used for micromechanical systems.

Continuous flow liquid transport has been described using a microfluidic device developed with silicon. See J. Pfahler et al., Sensors and Actuators, A21–A23 (1990), pp. 431–434. Pumps have also been described, using external forces to create flow, based on micromachining of silicon. See H. T. G. Van Lintel et al., Sensors and Actuators 15:153–167 (1988). SDS capillary gel electrophoresis of proteins in microfabricated channels has also been described. See Yao S et al., "SDS capillary gel electrophoresis of proteins in microfabricated channels," *PNAS* 96:5372 (1999). Compared to more conventional two-dimensional denaturing gel electorphoresis (which is generally time consuming and requires considerable amounts of sample), this microchannel-based separation technique was shown to be quick and offer high resolution.

As a mechanical building material, silicon has well-known fabrication characteristics. The economic attraction of silicon devices is that their associated micromachining technologies are, essentially, photographic reproduction techniques. In these processes, transparent templates or masks containing opaque designs are used to photodefine objects on the surface of the silicon substrate. The patterns on the templates are generated with computer-aided design programs and can delineate structures with line-widths of less than one micron. Once a template is generated, it can be used almost indefinitely to produce identical replicate structures. Consequently, even extremely complex micromachines can be reproduced in mass quantities and at low incremental unit cost—provided that all of the components are compatible with the silicon micromachining process. While the present invention contemplates other substrates, such as glass or quartz, for use in photolithographic methods to construct microfabricated analysis devices, silicon is preferred because of the added advantage of allowing a large variety of electronic components to be fabricated within the same structure.

In one embodiment, the present invention contemplates silicon micromachined components in an integrated analysis system. Sample (e.g. a test compound) and one or more reagents (e.g. a BODIPY labelled nascent protein) are injected either continuously or in pulses into the device through entry ports and they are transported through channels to a reaction chamber, such as a thermally controlled reactor where mixing and reactions take place. The biochemical products can be then moved down a new channel (or by an electrophoresis module, if desired) where migration data is collected by a detector and transmitted to a recording instrument. If desired, a polymer can be used in the channels to provide resolution by molecular sieving. The biochemical products can be isolated by diverting the flow to an external port for subsequent additional analysis. Importantly, the fluidic and electronic components are designed to be fully compatible in function and construction with the biological reactions and reagents. In this embodiment, potential test compounds can be rapidly screened for interaction with a labeled nascent protein or multiple nascent proteins that are co-expressed in a translation reaction system. In this manner the system can be used to screen for interaction so as to identify useful drugs.

In another embodiment, one or more components of the protein synthesis system are introduced into the device through entry ports and they are transported through channels to a reaction chamber, such as a thermally controlled reactor, where the expression of the nascent protein which contains the marker such as BODIPY occurs. The labeled nascent protein can than be mixed with one or more reagents (e.g. a test compound) that are introduced into the device through entry ports. After the reaction takes placed, the biochemical products can be then moved down a new channel (or by an electrophoresis module, if desired) where migration data is collected by a detector and transmitted to a recording instrument. It is to be understood that components of the protein synthesis system which can be introduced into the device can include misaminoacylated tRNAs, DNA, mRNA, amino acids and nucleotides. The components can be introduced either continuously or in discrete pulses. The DNA may also be produced within the micromachined device by enzymatic reactions such as the polymerase chain reaction as has been described. See Kopp et al., "Chemical Amplification: Continuous Flow PCR on a Chip," *Science* 280:1046 (1998).

In silicon micromachining, a simple technique to form closed channels involves etching an open trough on the surface of a substrate and then bonding a second, unetched substrate over the open channel. There are a wide variety of isotropic and anisotropic etch reagents, either liquid or gaseous, that can produce channels with well-defined side walls and uniform etch depths. Since the paths of the channels are defined by the photo-process mask, the complexity of channel patterns on the device is virtually unlimited. Controlled etching can also produce sample entry holes that pass completely through the substrate, resulting in entry ports on the outside surface of the device connected to channel structures.

G. Multiple Misaminoacylated tRNAs

It may often be advantageous to incorporate more than one marker into a single species of protein. This can be accomplished by using a single tRNA species such as a lysine tRNA misaminoacylated with both a marker such as dansyllysine and a coupling agent such as biotin-lysine. Alternatively, different tRNAs which are each misaminoacylated with different markers can also be utilized. For example, the coumarin derivative could be used to misaminoacylate a tryptophan tRNA and a dansyl-lysine used to misaminoacylate a lysine tRNA.

One use of multiple misaminoacylated tRNAs is to study the expression of proteins under the control of different genetic elements such as repressors or activators, or promoters or operators. For example, the synthesis of proteins at two different times in response to an internal or external agent could be distinguished by introducing misaminoacylated tRNAs at different times into the cellular or cell-free protein synthesis system. A $tRNA^{tyr}$ might be charged with marker A and a $tRNA^{lys}$ charged with marker B, yielding A-$tRNA^{tyr}$ and B-$tRNA^{lys}$, respectively. In this case, protein one under the control of one promoter can be labeled by adding the A-$tRNA^{tyr}$ to the reaction system. If a second misaminoacylated tRNA, B-$tRNA^{lys}$ is then added and a second promoter for protein two activated, the nascent protein produced will contain both label A and B. Additional markers could also be added using additional tRNA molecules to further study the expression of additional proteins. The detection and analysis of multiply labeled nascent proteins can be facilitated by using the multi-colored electrophoresis pattern reading system, described in U.S. Pat. No. 5,190,632, which is specifically incorporated by reference, or other multi-label reading systems such as those described in U.S. Pat. Nos. 5,069,769 and 5,137,609, which are both hereby specifically incorporated by reference.

A second use of multiple misaminoacylated tRNAs is in the combined isolation and detection of nascent proteins. For example, biotin-lysine marker could be used to misaminoacylate one tRNA and a coumarin marker used to misaminoacylate a different tRNA. Magnetic particles coated with streptavidin which binds the incorporated lysine-biotin would be used to isolate nascent proteins from the reaction mixture and the coumarin marker used for detection and quantitation.

A schematic diagram of the basics of the above methods is shown in FIG. 14. In a first step, the marker selected (M), which may have reporter (R) or affinity (A) properties, is chemically or enzymatically misaminoacylated to a single tRNA species or a mixture of different tRNAs. Prior to protein synthesis, a predetermined amount of the misaminoacylated tRNA, charged with the fluorescent marker is mixed with the cell-free protein synthesis reaction system at concentrations sufficient to allow the misaminoacylated tRNA to compete effectively with the corresponding tRNA. After an incubation of about 1–3 hours, the reaction mixture is analyzed using conventional polyacrylamide or agarose gel electrophoresis. After electrophoresis, the gel is illuminated by UV radiation. Bands due to the nascent protein exhibit distinct fluorescence and can be easily and rapidly distinguished, either visually or photographically, from non-fluorescent bands of preexisting proteins. Nascent proteins can be isolated by excising the fluorescent band and electroeluting the protein from the extracted gel pieces. The quantities and molecular weights of the nascent proteins can be determined by comparison of its fluorescence with the fluorescence produced by a set of proteins with known molecular weights and known quantities. The results of the assay can be recorded and stored for further analysis using standard electronic imaging and photographic or spectroscopic methods.

H. Resulting Compositions

Another embodiment of the invention is directed to a composition comprising nascent proteins isolated or purified by conventional methods after translation in the presence of markers. Compositions can be utilized in manufacturing for the preparation of reagents such as coatings for tissue culture products and in the pharmaceutical industry.

Incorporation of markers into nascent proteins utilized in manufacturing facilitates analysis of the final manufactured product or process by detection of marker. For example, nascent proteins produced may be used as coatings for tissue culture products. The reproducibility of a particular coating process could be accurately determined by detecting variations of marker emissions over the surface of the coated product. In addition, non-toxic markers incorporated into proteins encompassed within a pharmaceutical preparation such as a hormone, steroid, immune product or cytokine can be utilized to facilitate safe and economical isolation of that protein preparation. Such products could be used directly without the need for removal of marker. When very low concentrations of marker are preferred, limiting amounts of marked proteins could be used to follow a protein through a purification procedure. Such proteins can be efficiently purified and the purity of the resulting composition accurately determined. In addition, the presence of markers may facilitate study and analysis of pharmaceutical compositions in testing. For example, markers can be utilized to determine serum half-life, optimum serum levels and the presence or absence of break-down products of the composition in a patient.

Alternatively, nascent proteins may contain specific markers which serve as therapeutically useful compounds such as toxic substances. These proteins are administered to a patient and the therapeutic moiety released after proteins have identified and possibly bound to their respective targets. Release may be electrical stimulation, photochemical cleavage or other means whereby the moiety is specifically deposited in the area targeted by the nascent proteins. In addition, moieties such as modified toxins may be utilized which become toxic only after release from nascent proteins. Nascent protein may also serve as a pharmaceutical carrier which bestows the incorporated marker with active therapeutic function or prevents marker from breaking down in the body prior to its therapeutic or imaging action.

The incorporation of cleavable markers in nascent proteins further provides a means for removal of the non-native portion of the marker to facilitate isolation of the protein in a completely native form. For example, a cleavable affinity marker such as photocleavable biotin introduced into a nascent protein facilitates economical isolation of the protein and allows for the removal of the marker for further use as a pharmaceutical composition.

Pharmaceutical compositions of proteins prepared by translation in the presence of markers may further comprise a pharmaceutically acceptable carrier such as, for example, water, oils, lipids, polysaccharides, glycerols, collagens or combinations of these carriers. Useful immunological compositions include immunologically active compositions, such as a vaccine, and pharmaceutically active compositions, such as a therapeutic or prophylactic drug which can be used for the treatment of a disease or disorder in a human.

I. Kits

Another embodiment of the invention is directed to diagnostic kits or aids containing, preferably, a cell-free translation containing specific misaminoacylated tRNAs which incorporate markers into nascent proteins coded for by mRNA or genes, requiring coupled transcription-translation systems, and are only detectably present in diseased biological samples. Such kits may be useful as a rapid means to screen humans or other animals for the presence of certain diseases or disorders. Diseases which may be detected include infections, neoplasias and genetic disorders. Biological samples most easily tested include samples of blood, serum, tissue, urine or stool, prenatal samples, fetal cells, nasal cells or spinal fluid. In one example, misaminoacylate fmet-tRNAs could be used as a means to detect the presence of bacteria in biological samples containing prokaryotic cells. Kits would contain translation reagents necessary to synthesize protein plus tRNA molecules charged with detectable non-radioactive markers. The addition of a biological sample containing the bacteria-specific genes would supply the nucleic acid needed for translation. Bacteria from these samples would be selectively lysed using a bacteria directed toxin such as Colicin E1 or some other bacteria-specific permeabilizing agent. Specific genes from bacterial DNA could also be amplified using specific oligonucleotide primers in conjunction with polymerase chain reaction (PCR), as described in U.S. Pat. No. 4,683,195, which is hereby specifically incorporated by reference. Nascent proteins containing marker would necessarily have been produced from bacteria. Utilizing additional markers or additional types of detection kits, the specific bacterial infection may be identified.

The present invention also contemplates kits which permit the GFTT described above. For example, the present invention contemplates kits to detect specific diseases such as familial adenomatous polyposis. In about 30 to 60% of cases of familial adenomatous polyposis, the diseased tissues also contain chain terminated or truncated transcripts of the APC gene (S. M. Powell et al., N. Engl. J. Med. 329:1982–87, 1993). Chain termination occurs when frameshift cause a stop codon such as UAG, UAA or UGA to appear in the reading frame which terminates translation. Using misaminoacylated tRNAs which code for suppressor tRNAs, such transcripts can be rapidly and directly detected in inexpensive kits. These kits would contain a translation system, charged suppressor tRNAs containing detectable markers, for example photocleavable coumarin-biotin, and appropriate buffers and reagents. Such a kit might also contain primers or "pre-primers," the former comprising a promoter, RBS, start codon, a region coding an affinity tag and a region complementary to the template, the latter comprising a promoter, RBS, start codon, and region coding an affinity tag—but lacking a region complementary to the template. The pre-primer permits ligation of the region complementary to the template (allowing for customization for the specific template used). A biological sample, such as diseased cells, tissue or isolated DNA or mRNA or PCR products of the DNA, is added to the system, the system is incubated and the products analyzed. Analysis and, if desired, isolation is facilitated by a marker such as coumarin or biotin which can be specifically detected by its fluorescence using streptavidin coupled to HRP. Such kits provide a rapid, sensitive and selective non-radioactive diagnostic assay for the presence or absence of the disease.

Experimental

The following examples illustrate embodiments of the invention, but should not be viewed as limiting the scope of the invention. In some of the examples below, particular reagents and methods were employed as follows:

Reagents tRNA$^{fmet}$, aminoacyl-tRNA synthetase, amino acids, buffer salts, and RNase free water were purchased from Sigma (St. Louis, Mo.). Many of the fluorescent dyes were obtained from Molecular Probes (Eugene, Oreg.). The translation supplies including routine kits were purchased from Promega (Madison, Wis.). Sephadex G-25 was from Amersham-Pharmacia Biotech (Piscataway, N.J.). The in vitro translation kits and plasmid DNAs coding for CAT (PinPoint™) and Luciferase (pBESTluc™) were from Promega (Wisconsin-Madison, Wis.) while DHFR plasmid DNA (pQE16-DHFR) was obtained from Qiagen (Valencia, Calif.). The plasmid DNA for α-hemolysin, pT7-WT-H6-αHL was kindly supplied by Prof. Hagan Bayley (Texas A & M University) and large scale preparation of α-HL DNA was carried out using Qiagen plasmid isolation kit. The bacterioopsin plasmid DNA (pKKbop) was from the laboratory stock.

Preparation of FluoroTag tRNAs

The purified tRNAf$^{fmet}$ was first aminoacylated with the methionine. In typical reaction, 1500 picomoles (~1.0 OD$_{260}$) of tRNA was incubated for 45 min at 37° C. in aminoacylation mix using excess of aminoacyl tRNA-synthetases. After incubation, the mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 µl). The coupling of NHS-derivatives of fluorescent molecules to the α-amino group of methionine was carried out in 50 mM sodium carbonate, pH 8.5 by incubating the aminoacylated tRNAf$^{met}$ (25 µl) with fluorescent reagent (final concentration=2 mM) for 10 min at 0° C. and the reaction was quenched by the addition of lysine (final concentration= 100 mM). The modified tRNA was precipitated with ethanol and passed through Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis. This tRNA was found to be stable at least for 6 month if stored properly.

Cell Free Synthesis of Proteins and their Detection

The in vitro translation reactions were typcially carried out using *E. coli* T7 transcription-translation system (Promega) with optimized premix. The typical translation reaction mixture (10 µl) contained 3 µl of extract, 4 µl of premix, 1 µl of complete amino acid mix, 30 picomoles of fluorescent-methionyl-tRNA and 0.5 µg of appropriate plasmid DNA. The optimized premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 16 mM magnesium acetate. The translation reaction was allowed to proceed for 45 min at 37° C. For SDS-PAGE, 4–10 µl aliquot of the reaction mix was precipitated with 5-volume acetone and the precipitated proteins were collected by centrifugation. The pellet was dissolved in 1× loading buffer and subjected to SDS-PAGE after boiling for 5 min. SDS-PAGE was carried out according to Laemmli and the gel was scanned using Molecular Dynamics FluorImager 595 using Argon laser as excitation source. Alternatively, the nascent proteins in polyacrylamide gels were also detected using an UV-transilluminator and the photographs were carried out using Polaroid camera fitted with green filter (Tiffen green #58, Polaroid DS34 camera filter kit).

For visualization of BODIPY-FL labeled protein, 488 nm as excitation source was used along with a 530+/−30 narrow band excitation filter. The gel was scanned using PMT voltage 1000 volts and either 100 or 200 micron pixel size.

Enzyme/Protein Activities

Biological activity of α-hemolysin was carried out as follows. Briefly, various aliquots (0.5–2 µl) of in vitro translation reaction mixture were added to 500 µl of TBSA (Tris-buffered saline containing 1 mg/ml BSA, pH 7.5). To this, 25 µl of 10% solution of rabbit red blood cells (rRBCs) was added and incubated at room temperature for 20 min. After incubation, the assay mix was centrifuged for 1 min and the absorbance of supernatant was measured at 415 nm (release of hemoglobin). The equal amount of rRBCs incubated in 500 µl of TBSA is taken as control while rRBCs incubated with 500 µl of water as taken 100% lysis. The DHFR activity was measured spectrophotometrically. Luciferase activity was determined using luciferase assay system (Promega) and luminescence was measures using Packard Lumi-96 luminometer.

Purification of α-HL and Measurement BODIPY-FL Incorporation into α-HL

The translation of plasmid coding for α-HL (His$_6$) was carried out at 100 µl scale and the α-HL produced was purified using Talon-Sepharose (ClonTech) according manufacturer instructions. The fluorescence incorporated into α-HL was then measured on Molecular Dynamics FluorImager along with the several known concentration of free BODIPY-FL (used as standard). The amount of protein in the same sample was measured using a standard Bradford assay using Pierce Protein Assay kit (Pierce, Rockford, Ill.).

EXAMPLE 1

Preparation of Markers

Synthesis of Coumarin Amino Acid: 4-(Bromomethyl)-7-methoxy coumarin (FIG. 15, compound 1; 6.18 mmole) and diethylacetamidomalonate (FIG. 15, compound 2; 6.18 mmole) were added to a solution of sodium ethoxide in absolute ethanol and the mixture refluxed for 4 hours. The intermediate obtained (FIG. 15, compound 3) after neutralization of the reaction mixture and chloroform extraction was further purified by crystallization from methanolic solution. This intermediate was dissolved in a mixture of acetone and HCl (1:1) and refluxed for one hour. The reaction mixture was evaporated to dryness, and the amino acid hydrochloride precipitated using acetone. This hydrochloride was converted to free amino acid (FIG. 15, compound 4) by dissolving in 50% ethanol and adding pyridine to pH 4–5. The proton ($^1$H) NMR spectrum of the free amino acid was as follows: (m.p. 274–276° C., decomp.) —OCH$_3$ (δ3.85 s, 3H), —CH$_2$-(δ3.5 d, 2H), α-CH—(δ2.9 t, 1H), CH—CO (δ6.25 s, 1H), ring H (δ7.05 s, 1H), (δ7.8 d, 2H).

Synthesis of Fmoc derivative of coumarin: Coumarin amino acid (1.14 mmol) was reacted with Fluorenylmethyloxycarbonyl N-hydroxysuccininmidyl ester (Fmoc-NHS ester) 1.08 mmol) in the presence of 1.14 mmol of triethylamine for 30 minutes at room temperature. The reaction mixture was acidified and the precipitate washed with 1 N HCl and dried. The NMR spectrum of the free amino acid was as follows: (MP 223–225° C.) —OCH$_3$ ($\delta$3.85 s, 3H), —CH$_2$Br ($\delta$3.5 broad singlet, 2H), $\alpha$—CH—($\delta$3.0 t, 1H), CH—CO ($\delta$6.22 m, 1H), ring H ($\delta$7.05 s, 1H), ($\delta$7.8 d, 2H), fluorene H CH$_2$—CH ($\delta$4.2 m, 2H), CH$_2$-CH ($\delta$4.25 m, 1H), aromatic regions showed characteristic multiplets.

Synthesis of PCB: Photocleavable biotin was synthesized as described below. 2-bromo, 2'-nitroacetophenone (FIG. 15, compound 5) was converted first into its hexamethyltetraamommonium salt which was decomposed to obtain 2-amino, 2'-nitroacetophenone (FIG. 15, compound 6). Biotin N-hydroxysuccinimidyl ester (FIG. 15, compound 7; Sigma Chemical; St. Louis, Mo.) was reacted with a 6-aminocaproic acid (FIG. 15, compound 8) to obtain the corresponding acid (FIG. 15, compound 9). This acid was coupled with the 2-amino, 2'nitroacetophenone using DCC to obtain the ketone (FIG. 15, compound 10). The ketone was reduced using sodium borohydride to obtain the alcohol (FIG. 15, compound 11) which was further converted into its chloroformate derivative (FIG. 15, compound 12). The proton NMR spectrum of the derivative (compound 12) was as follows: ($\delta$1.3 m, 3H), ($\delta$1.4 m, 2H), ($\delta$1.5 m, 5H) ($\delta$1.62 m, 1H), ($\delta$2.1 t, 2H) ($\delta$2.4 t, 2H), ($\delta$2.6 d, 1H), ($\delta$2.8 m, 1H), ($\delta$3.0 t, 1H), ($\delta$3.1 m 1H), ($\delta$4.15 qt, 1H) ($\delta$4.42 qt, 1H), ($\delta$5.8 t, 1H), ($\delta$6.25 s, 1H), ($\delta$6.45 s, 1H), ($\delta$7.5 t, 1H), ($\delta$7.75 m, 4H), ($\delta$7.9 d, 1H).

EXAMPLE 2
Misaminoacylation of tRNA

The general strategy used for generating misaminoacylated tRNA is shown in FIG. 16 and involved truncation of tRNA molecules, dinucleotide synthesis (FIG. 17), aminoacylation of the dinucleotide (FIG. 18) and ligase mediated coupling.

a) Truncated tRNA molecules were generated by periodate degradation in the presence of lysine and alkaline phosphatase basically as described by Neu and Heppel (J. Biol. Chem. 239:2927–34, 1964). Briefly, 4 mmoles of uncharged E. coli tRNA$^{Lys}$ molecules (Sigma Chemical; St. Louis, Mo.) were truncated with two successive treatments of 50 mM sodium metaperiodate and 0.5 M lysine, pH 9.0, at 60° C. for 30 minutes in a total volume of 50 $\mu$l. Reaction conditions were always above 50° C. and utilized a 10-fold excess of metaperiodate. Excess periodate was destroyed treatment with 5 $\mu$l of 1M glycerol. The pH of the solution was adjusted to 8.5 by adding 15 $\mu$l of Tris-HCl to a final concentration of 0.1 M. The reaction volume was increased to 150 $\mu$l by adding 100 $\mu$l of water. Alkaline phosphatase (15 $\mu$l, 30 units) was added and the reaction mixture incubated again at 60° C. for two hours. Incubation was followed by ethanol precipitation of total tRNA, ethanol washing, drying the pellet and dissolving the pellet in 20 $\mu$l water. This process was repeated twice to obtain the truncated tRNA.

b) Dinucleotide synthesis was carried out basically as performed by Hudson (J. Org. Chem. 53:617–24, 1988), and can be described as a three step process, deoxycytidine protection, adenosine protection and dinucleotide synthesis.

Deoxycytidine protection: All reaction were conducted at room temperature unless otherwise indicated. First, the 5' and 3' hydroxyl groups of deoxycytidine were protected by reacting with 4.1 equivalents of trimethylsilyl chloride for 2 hours with constant stirring. Exocyclic amine function was protected by reacting it with 1.1 equivalents of Fmoc-Cl for 3 hours. Deprotection of the 5' and 3' hydroxyl was accomplished by the addition of 0.05 equivalents of KF and incubation for 30 minutes. The resulting product (FIG. 17, compound 19) was produced at an 87% yield. Phosphate groups were added by incubating this compound with 1 equivalent of bis-(2-chlorophenyl)phosphorochloridate and incubating the mixture for 2 hours at 0° C. The yield in this case was 25–30%.

Adenosine protection: Trimethylsilyl chloride (4.1 equivalents) was added to adenosine residue and incubated for 2 hours, after which, 1.1 equivalents of Fmoc-Cl introduced and incubation continued for 3 hours. The TMS groups were deprotected with 0.5 equivalents of fluoride ions as described above. The Fmoc protected adenosine (compound 22) was obtained in a 56% yield. To further protect the 2'-hydroxyl, compound 22 was reacted with 1.1 equivalents of tetraisopropyl disiloxyl chloride (TIPDSCl$_2$) for 3 hours which produces compound 23 at a 68–70% yield. The compound was converted to compound 24 by incubation with 20 equivalents of dihydropyran and 0.33 equivalents of p-toluenesulfonic acid in dioxane for about 4–5 hours. This compound was directly converted without isolation into compound 25 (FIG. 17) by the addition of 8 equivalents of tetrabutyl ammonium fluoride in a mixture of tetrahydro-furan, pyridine and water.

Dinucleotide synthesis: The protected deoxycytidine, compound 20, and the protected adenosine, compound 25 (FIG. 17), were coupled by the addition of 1.1 equivalents of 2-chlorophenyl bis-(1-hydroxy benzotriazolyl) phosphate in tetrahydrofuran with constant stirring for 30 minutes. This was followed by the addition of 1.3 equivalents of protected adenosine, compound 25, in the presence of N-methylimidazole for 30 minutes. The coupling yield was about 70% and the proton NMR spectrum of the coupled product, compound 26 (FIG. 17), was as follows: ($\delta$8.76 m, 2H), ($\delta$8.0 m, 3H), ($\delta$7.8 m, 3H) ($\delta$7.6 m, 4H), ($\delta$7.5 m, 3H), ($\delta$7.4 m, 18H), ($\delta$7.0 m, 2H), ($\delta$4.85 m, 14H), ($\delta$4.25 m, 1H); ($\delta$3.6 m, 2H), ($\delta$3.2 m, 2H) ($\delta$2.9 m, 3H), ($\delta$2.6 m, 1H), ($\delta$2.01–1.2 m, 7H).

c) Aminoacylation of the dinucleotide was accomplished by linking the protected marker amino acid, Fmoc-coumarin, to the dinucleotide with an ester linkage. First, the protected amino acid was activated with 6 equivalents of benzotriazol-1-yl-oxy tris-(dimethylamino) phosphonium hexafluoro phosphate and 60 equivalents of 1-hydroxybenzotriazole in tetrahydrofuran. The mixture was incubated for 20 minutes with continuous stirring. This was followed with the addition of 1 equivalent of dinucleotide in 3 equivalents N-methylimidazole, and the reaction continued at room temperature for 2 hours. Deprotection was carried out by the addition of tetramethyl guanidine and 4-nitrobenzaldoxime, and continuous stirring for another 3 hours. The reaction was completed by the addition of acetic acid and incubation, again with continuous stirring for 30 minutes at 0° C. which produced the aminoacylated dinucleotide (FIG. 18).

d) Ligation of the tRNA to the aminoacylated dinucleotide was performed basically as described by T. G. Heckler et al. (Tetrahedron 40: 87–94, 1984). Briefly, truncated tRNA molecules (8.6 O.D.$_{260}$ units/ml) and aminoacylated dinucleotides (4.6 O.D.$_{260}$ units/ml), were incubated with 340 units/ml T4 RNA ligase for 16 hours at 4° C. The reaction buffer included 55 mM Na-Hepes, pH 7.5, 15 mM MgCl$_2$, 250 $\mu$M ATP, 20 $\mu$g/ml BSA and 10% DMSO. After incubation, the reaction mixture was diluted to a final concentration of 50 mM NaOAc, pH 4.5, containing 10 mM MgCl$_2$. The resulting mixture was applied to a DEAE-cellulose column (1 ml), equilibrated with 50 mM NaOAc, pH 4.5, 10 mM MgCl$_2$, at 4° C. The column was washed with 0.25 mM NaCl to remove RNA ligase and other non-tRNA components. The tRNA-containing factions were pooled and loaded onto a BD-cellulose column at 4° C., that had been equilibrated with 50 mM NaOAc, pH 4.5, 10 mM $MgCl_2$, and 1.0 M NaCl. Unreacted tRNA was removed by washes with 10 ml of the same buffer. Pure misaminoacylated tRNA was obtained by eluting the column with buffer containing 25% ethanol.

EXAMPLE 3
Preparation of Extract and Template

Preparation of extract: Wheat germ embryo extract was prepared by floatation of wheat germs to enrich for embryos using a mixture of cyclohexane and carbon tetrachloride (1:6), followed by drying overnight (about 14 hours). Floated wheat germ embryos (5 g) were ground in a mortar with 5 grams of powdered glass to obtain a fine powder. Extraction medium (Buffer I: 10 mM trisacetate buffer, pH 7.6, 1 nM magnesium acetate, 90 mM potassium acetate, and 1 mM DTT) was added to small portions until a smooth paste was obtained. The homogenate containing disrupted embryos and 25 ml of extraction medium was centrifuged twice at 23,000×g. The extract was applied to a Sephadex G-25 fine column and eluted in Buffer II (10 mM trisacetate buffer, pH 7.6, 3 mM magnesium acetate, 50 mM potassium acetate, and 1 mM DTT). A bright yellow band migrating in void volume and was collected (S-23) as one ml fractions which were frozen in liquid nitrogen.

Preparation of template: Template DNA was prepared by linearizing plasmid pSP72-bop with EcoRI. Restricted linear template DNA was purified by phenol extraction and DNA precipitation. Large scale mRNA synthesis was carried out by in vitro transcription using the SP6-ribomax system (Promega; Madison, Wis.). Purified mRNA was denatured at 67° C. for 10 minutes immediately prior to use.

EXAMPLE 4
Cell-Free Translation Reactions

The incorporation mixture (100 μl) contained 50 μl of S-23 extract, 5 mM magnesium acetate, 5 mM Tris-acetate, pH 7.6, 20 mM Hepes-KOH buffer, pH 7.5; 100 mM potassium acetate, 0.5 mM DTT, 0.375 mM GTP, 2.5 mM ATP, 10 mM creatine phosphate, 60 μg/ml creatine kinase, and 100 μg/ml mRNA containing the genetic sequence which codes for bacterioopsin. Misaminoacylated PCB-lysine or coumarin amino acid-tRNA$^{lys}$ molecules were added at 170 μg/ml and concentrations of magnesium ions and ATP were optimized. The mixture was incubated at 25° C. for one hour.

EXAMPLE 5
Isolation of Nascent Proteins Containing PCB-Lysine

Streptavidin coated magnetic Dynabeads M-280 (Dynal; Oslo, Norway), having a binding capacity of 10 μg of biotinylated protein per mg of bead. Beads at concentrations of 2 mg/ml, were washed at least 3 times to remove stabilizing BSA. The translation mixture containing PCB-lysine incorporated into nascent protein was mixed with streptavidin coated beads and incubated at room temperature for 30 minutes. A magnetic field was applied using a magnetic particle concentrator (MPC) (Dynal; Oslo, Norway) for 0.5–1.0 minute and the supernatant removed with pipettes. The reaction mixture was washed 3 times and the magnetic beads suspended in 50 μl of water.

Photolysis was carried out in a quartz cuvette using a Black-Ray longwave UV lamp, Model B-100 (UV Products, Inc.; San Gabriel, Calif.). The emission peak intensity was approximately 1100 μW/$cm^2$ at 365 nm. Magnetic capture was repeated to remove the beads. Nascent proteins obtained were quantitated and yields estimated at 70–95%.

EXAMPLE 6
The Lower Limit of Detection using Fluorescence

Bovine serum albumin (BSA), suspended at 0.25 mg/ml in borate buffer, pH 8.0, was combined with a 25 fold molar excess fluorescamine (Sigma Chemical; St. Louis, Mo.) at 50 mg/ml to produce a modified, fluorescent BSA. Various amounts of modified protein (1 ng, 5 ng, 10 ng, 25 ng, 50 ng, 75 ng, 100 ng, 150 ng, 200 ng) were suspended in loading buffer (bromophenol blue, glycerol, 2-mercaptoethanol, Tris-HCl, pH 6.8, SDS), and added to individual wells of a 1.5 mm thick, 12% polyacrylamide gel with a 3% stacker. The water cooled gel was electrophoresed for 4 hours at 50 volts. After electrophoresis, the gel was removed from the electrophoresis apparatus, placed on a UV transilluminator and photographed with polaroid Type 667 film using an exposure time of 10 seconds. The lowest limit of detection observed under theses conditions was 10 ng. These results indicate that using equipment found in a typical molecular biology lab, fluorescently labeled proteins can be detected at ng quantities. Using even more sophisticated detection procedures and devices the level of detection can be increased even further.

EXAMPLE 7
Nascent Proteins Containing Coumarin-Amino Acid

Cell-free translation is performed as described using charged tRNA$^{lys}$ molecules misaminoacylated with lysine coupled to a benzopyrene fluorophore moiety and human γ-interferon mRNA which contains 21 codons for lysine. Samples of the mixture are supplemented with buffer containing bromophenol blue, glycerol, 2-mercaptoethanol, Tris-HCl, pH 6.8, and SDS, and directly applied to a 12% poly-acrylamide gel (3% stacker) along with a set of molecular weight markers. Electrophoresis is performed for 3 hours at 50 volts. The gel is removed from the electrophoresis apparatus and photographed under UV light. Bands of fluorescently labeled interferon protein are specifically detected at a molecular weight of about 25 KDa. No other significant fluorescent activity is observed on the gel. Free misaminoacylated tRNA molecules may be electrophoresed off of the gel and not specifically detected.

EXAMPLE 8
In vivo Half-life of a Pharmaceutical Composition

Cell-free translation reactions are performed by mixing 10 μl of PCB-coumarin amino acid-tRNA$^{leu}$, prepared by chemical misaminoacylation as described above and suspended in TE at 1.7 mg/ml), 50 μl of S-23 extract, 10 μl water and 10 μl of a solution of 50 mM magnesium acetate, 50 mM Tris-acetate, pH 7.6, 200 mM Hepes-KOH buffer, pH 7.5; 1 M potassium acetate, 5 mM DTT, 3.75 mM GTP, 25 mM ATP, 100 mM creatine phosphate and 600 μg/ml creatine kinase. This mixture is kept on ice until the addition of 20 μl of 500 μg/ml human IL-2 mRNA (containing 26 leucine codons) transcribed and isolated from recombinant IL-2 cDNA. The mixture is incubated at 25° C. for one hour and placed on ice. 100 μl of streptavidin coated magnetic Dynabeads (2 mg/ml) are added to the mixture which is placed at room temperature for 30 minutes. After incubation, the mixture is centrifuged for 5 minutes in a microfuge at 3,000×g or, a magnetic field is applied to the solution using a MPC. Supernatant is removed and the procedure repeated three times with TE. The final washed pellet is resuspended in 50 μl of 50 mM Tris-HCl, pH 7.5 and transferred to a quartz cuvette. UV light from a Black-Ray longwave UV lamp is applied to the suspension for approximately 1 second. A magnetic field is applied to the solution with a MPC for 1.0 minute and the supernatant removed with a pipette. The supernatant is sterile filtered and mixed with equal volumes of sterile buffer containing 50% glycerol, 1.8% NaCl and 25 mM sodium bicarbonate. Protein concentration is determined by measuring the $O.D._{260}$.

0.25 ml of the resulting composition is injected i.v. into the tail vein of 2 Balb/c mice at concentrations of 1 mg/ml. Two control mice are also injected with a comparable volume of buffer. At various time points (0, 5 minutes, 15 minutes, 30 minutes, 60 minutes, 2 hours and 6 hours), 100 µl serum samples are obtained from foot pads and added to 400 µl of 0.9% saline. Serum sample are added to a solution of dynabeads (2 mg/ml) coated with anti-coumarin antibody and incubated at room temperature for 30 minutes. A magnetic field is applied to the solution with a MPC for 1 minute and the supernatant removed with a pipette. Fluorescence at 470 nm is measured and the samples treated with monoclonal antibody specific for rat IL-2 protein. IL-2 protein content is quantitated for each sample and equated with the amount of fluorescence detected. From the results obtained, in vivo IL-2 half-life is accurately determined.

EXAMPLE 9

Incorporation of Various Fluorophores into α-Hemolysin

E. coli $tRNA^{fmet}$ was first quantitatively aminoacylated with methionine and the α-amino group was specifically modified using NHS-derivatives of several fluorophores. The list of fluorescent reporter molecules (fluorophores) tested and their properties are given in Table 2. Under the modification conditions, the modified Met-$tRNA^{fmet}$ is found to be stable as assessed by acid-urea gel. Since all the fluorescent molecules tested have different optical properties (excitation and emission), we have determined their relative fluorescence intensity under the condition which were used for the quantitation of gels containing nascent protein.

Fluorescent detection of nascent protein was first evaluated using α-hemolysin (α-HL) as a model protein (with C-terminal $His_6$-tag). α-HL is relatively small protein (32 kDa) and could be produced efficiently in in vitro translation. In addition, its activity can be measured directly in the protein translation mixture using a rabbit red blood cell hemolysis assay. In vitro translation of α-HL was carried out using an E. coli T7 S30 transcription/translation extract (Promega Corp., Madison, Wis.) in the presence of several different modified methionyl-$tRNA^{fmet}$ as described above. After the reaction, an aliquot (3–5 µl) was subjected to SDS-PAGE analysis and the fluorescent bands were detected and quantitated using a FluorImager F595 (Molecular Dynamics, Sunnyvale, Calif.).

The data is presented in FIG. 20. Lane 1 is a no DNA control. Lane 2 shows the results with BODIPY-FL-SSE. Lane 3 shows the results with BODIPY-FL-SE. Lane 4 shows the results with NBD (see Table 2 for the structure). Lane 5 shows the results with Bodipy-TMR. Lane 6 shows the results with BODIPY R6G. Lanes 7, 8, 9 and 10 show the results achieved with FAM, SFX, PYMPO and TAMRA, respectively (see Table 2 for structures).

The results clearly indicate the α-HL produced in presence of BODIPY-FL-methionyl-$tRNA^{fmet}$ (lanes 2 and 3) exhibited the highest fluorescence (all the data is normalized to the BODIPY-FL-SSE. The two different BODIPY-FL reagents (BODIPY-FL sulfosuccinimidyl ester (SSE) and BODIPY-FL succinimidyl ester (SE)), differ only with respect to solubility. The next best fluorophore evaluated, 6-(tetramethylrhodamine-5-(and-6)-carboxamido)hexanoic acid, succinimidyl ester (TAMRA-X, SE), exhibited 35% of the fluorescence (corrected for relative fluorescence) of BODIPY-FL-SSE. Two other forms of BODIPY, BODIPY-TMR, SE (6-((4,4-difluoro-1,3-dimethyl-5-(4-methoxyphenyl)-4-bora-3a,4a-diaza-s-indacene-2-propionyl)amino)hexanoic acid, succinimidyl ester) and BODIPY-R6G, SE (4,4-difluoro-5-phenyl-bora-3a,4a-diaza-s-indacene-3-propionic acid, succinimidyl ester) exhibited less than 3% of the fluorescence of BODIPY-FL, SSE. Succinimidyl 6-(7-nitrobenz-2-oxa-1,3-diazol-4-yl) aminohexanoate (NBD-X-SE), a fluorescent molecule which has previously been incorporated into the neurokinin-2 receptor exhibited only 6% of the BODIPY-FL-SSE. The two fluorescein analogs 5-(and-6)-carboxyfluorescein, succinimidyl-ester (FAM, SE) and 6-(fluorescein-5-(and-6) carboxamido)hexanoic acid, succinimidyl ester (SFX, SE) also showed very low fluorescence (8.4% and 4.6%, respectively relative to BODIPY-FL).

EXAMPLE 10

Optimizing Incorporation

In order to optimize the amount of BODIPY-FL incorporated into nascent proteins, the translation reaction for α-HL was carried out in presence of increasing amounts of BODIPY-FL-methionyl-$tRNA^{fmet}$ ranging from 3–60 picomoles per reaction. All reactions yielded similar amount of α-HL as determined by hemolysis activity of rabbit red blood cells indicating that the exogenously added BODIPY-FL-methionyl-$tRNA^{fmet}$ in this range did not inhibit protein synthesis. In contrast, the intensity of the fluorescent band corresponding to α-HL continued to increase up to 30 picomoles BODIPY-FL-methionyl-tRNA per 10 µl reaction (data not shown). Increases above this level produced no further increase in fluorescence, thus subsequent reactions were performed using this level of BODIPY-FL-methionyl-tRNA.

A second step used to optimize BODIPY-FL incorporation was based on eliminating N-formyl-tetrahydrofolate (fTHF) from the reaction mixture. In prokaryotes, N-formyl-tetrahydrofolate (fTHF) acts as a cofactor for the enzyme methionyl-tRNA transformylase, which formylates the initiator tRNA after its aminoacylation with methionine. Protein synthesis is then initiated using this modified tRNA (formyl-methionine-tRNA). Without limiting the invention to any particular mechanism, it is believed that eliminating fTHF from the reaction mixture reduces the competition for initiation of protein synthesis between this endogenous initiator tRNA and exogenously added modified-initiator RNA by preventing the formylation of endogenous initiator tRNA. This was confirmed by measuring fluorescence directly from SDS-PAGE for reactions for which fTHF was present and absent from the reaction mixture. In the later case, a 2–3 fold increase in fluorescence was found (data not shown).

EXAMPLE 11

Incorporation into Other Proteins

In order to explore the general applicability of this approach, transcription/translation reactions with BODIPY-FL-methionyl-$tRNA^{fmet}$ were carried out using various plasmid DNAs coding for hemolysin dihydrofolate (DHFR), luciferase, chloramphenicol acetyl-transferase (CAT) and bacteriorhodopsin (BR). BR was included because it represents membrane proteins, which are typically very hydrophobic. An optimized coupled transcription/translation system was used along with free BODIPY-FL and BODIPY-FL-methionyl-$tRNA^{fmet}$ using the Talon metal chelate resin (ClonTech, Palo Alto, Calif.) in order to examine incorporation into other proteins. The results are shown in FIGS. 21A (visualization using laser based Molecular Dynamics FluorImager 595) and 21B (visualization using a UV-transilluminator). Lane 1 is a no DNA control. Lanes 2, 3, 4, 5 and 6 are hemolysin, DHFR, Luciferase, CAT and bacteriohodopsin, respectively.

Fluorescent bands are observed using a fluorescence scanner for each of the proteins at positions corresponding to their relative molecular. In the case of luciferase, bands are observed which correspond to the expected products of false initiation at internal methionines (Promega Technical Bulletin TB219). Bands corresponding to all of the proteins could also be observed visually and recorded photographically using a UV transilluminator (UVP TMW-20) combined with an emission filter that allows light with $\lambda > 450$ nm (FIG. 21B). Excitation in this case is likely to occur in the UV absorbing band of BODIPY-FL which extends from 300–400 nm.

The amount of BODIPY incorporation was then determined by measuring the amount of incorporated BODIPY-FL and protein present in the purified sample by comparison with solutions of different concentrations of BODIPY-FL and using a Bradford protein assay, respectively. The average of three such measurements yielded a molar ratio of 0.29+/−0.03%. However, the incorporation yield is likely to be higher since fluorescence quenching of BODIPY-FL with protein residues such as tryptophan and tyrosine may lower the fluorescence quantum yield compared to BODIPY-FL in aqueous solution.

The effects of the fluorescence labeling procedure on the activity of the nascent proteins synthesized was also evaluated. This is important in cases where it is desirable to perform downstream functional analysis such as in the case of in vitro expression cloning and other proteomic applications of in vitro technology. Although it is possible for the N-terminal fluorescent label to alter the function of a protein, the low molar incorporation level (~0.3%) should not significantly alter the overall activity of the extract. This is confirmed by various enzyme assays and no significant difference is found for the activity measured for DHFR, $\alpha$-HL and luciferase synthesized in the presence and absence of the BODIPY-FL-methionyl-tRNA$^{fmet}$ (see Table 3).

EXAMPLE 12
Measuring the Sensitivity

In order to estimate the sensitivity of the method, various dilutions of the translation extract corresponding to 0.003–0.5 $\mu$l of the original reaction mixture were analyzed by SDS-PAGE. As a control, extract from a reaction performed without DNA was analyzed. As seen in FIG. 22B, fluorescence from $\alpha$-HL bands corresponding to as small as 0.007 $\mu$l of the original reaction mixture were detectable. Based on the our estimation of total nascent protein produced in the in vitro system, which ranged from 50–80 $\mu$g/ml, this corresponds to 0.35–0.5 nanograms of $\alpha$-hemolysin. This compares favorably with the sensitivity obtainable using radioisotope labeling of nascent proteins where such a low expression of nascent protein may required longer exposure to X-ray film which might result in serious background problem. It also exceeds the sensitivity of measuring proteins on gels currently with commercially available dyes such as coomasie blue (8–100 nanograms). Further improvements in sensitivity are expected by increasing the level of BODIPY-FL incorporation and by reducing background fluorescence, which appears to be due to fluorescent impurities in the gel material, extract and modified tRNA added.

EXAMPLE 13
Synthesis as a Function of Time

The ability of the fluorescent labeling approach to monitor the nascent protein synthesis as a function of time was also evaluated. For this purpose, small aliquots of the $\alpha$-HL transcription/translation mixture (4 $\mu$l) were withdrawn at various times during the reaction and analyzed by SDS-PAGE. As seen in FIG. 22A, bands due to $\alpha$-HL can clearly be detected as early as 5 minutes after initiation of the incubation. Synthesis of fluorescently labeled $\alpha$-HL appears to saturate after 15 minutes of translation.

EXAMPLE 14
The Modifying Reagent

In the case of post-aminoacylation modifications used to form a misaminoacylated tRNA, an important factor is the modifying reagent used to add the modification to the natural amino acid. For example, in the case of the fluorophore BODIPY FL, there are two different commercially available BODIPY FL NHS reagents known as BODIPY-FL-SE and BODIPY-FL-SSE (Molecular Probes). Both reagents are based on N-hydroxysucinimide (NHS) as the leaving group. However, the two forms differ in aqueous solubility due to the presence in one form (SSE) of a sulonate (sulfo) group (see Table 2 for structures). In this example, optimized reactions based on standard biochemical procedures were performed aimed at adding the BODIPY FL fluorophore to a purified tRNA$^{fmet}$ which is aminoacylated with methionine using these two different reagents. For this purpose, first the tRNA$^{fmet}$ was aminoacylated with the methionine. In typical reaction, 1500 picomoles (~1.0 OD$_{260}$) of tRNA was incubated for 45 min at 37° C. in aminoacylation mix using excess of aminoacyl tRNA-synthetases. The aminoacylation mix consisted of 20 mM imidazole-HCl buffer, pH 7.5, 150 mM NaCl, 10 mM MgCl$_2$, 2 mM ATP and 1600 units of aminoacyl tRNA-synthetase. The extent of aminoacylation was determined by acid-urea gel as well as using $^{35}$S-methionine. After incubation, the mixture was neutralized by adding 0.1 volume of 3 M sodium acetate, pH 5.0 and subjected to chloroform:acid phenol (pH 5.0) extraction (1:1). Ethanol (2.5 volumes) was added to the aqueous phase and the tRNA pellet obtained was dissolved in water (37.5 (1) and used for modification.

A. Modification of Aminoacylated tRNA with BODIPY-FL-SSE

To the above aminoacylated-tRNA solution, 2.5 (1 of 1N NaHCO$_3$ was added (final conc. 50 mM, pH=8.5) followed by 10 (1 of 10 mM solution of BODIPY-FL-SSE (Molecular Probes) in water. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ml microliters of water and purified on Sephadex G-25 gel filtration column (0.5×5 cm) to remove any free fluorescent reagent, if present. The modified tRNA was stored frozen (−70° C.) in small aliquots in order to avoid free-thaws.

B. Modification of Aminoacylated tRNA with BODIPY-FL-SE

To the above aminoacylated-tRNA solution, 2.5 (1 of 1N NaHCO$_3$ (final conc. 50 mM, pH=8.5) and 20 (1 of DMSO was added followed by 10 (1 of 10 mM solution of BODIPY-FL-SE (Molecular Probes) in DMSO. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ml of water and purified on Sephadex G-25 gel filtration column (0.5×5 cm) to remove any free fluorescent reagent, if present. The modified tRNA was stored frozen (−70° C.) in small aliquots in order to avoid free-thaws.

C. Analysis

It was found empirically using HPLC that the extent of modification of the (alpha-amino group of methionine is substantially greater using the sulfonated form of NHS BODIPY FL compared to the non-sulfonated form of NHS-BODIPY FL reagent. In addition the misaminoacylated tRNA$^{fmet}$ formed using the sulfonated form was found to exhibit superior properties. When used in an optimized S30 E.coli translation systems to incorporate BIDOPY FL into the protein (hemolysin using a plasmid containing the HL gene under control of a T7 promoter), the band on an SDS-PAGE gel corresponding to the expressed HL exhibited an approximately 2 times higher level of fluorescence when detected using a argon laser based fluoroimager compared to a similar system using the misaminoacylated formed using the non-sulfonated form.

D. Coumarin

A similar result to that described above was obtained by comparing the non-sulfonated and sulfonated NHS derivitives of coumarin, which are also commercially available and referred to respectively as succinimidyl 7-amino-methyl-amino-coumarin acetate (AMCA-NHS; Molecular Probes) and sulfosuccinimidyl 7-amino-4-methylcoumarin-3-acetate (AMCA-sulfo-NHS; Pierce Chemicals). In this case, optimized reactions were performed using these two different reagents based on standard biochemical procedures in order to add the coumarin fluorophore to a purified tRNA$^{fmet}$ which is aminoacylated with methionine.

To the aminoacylated-tRNA solution described above, 2.5 (1 of 1N NaHCO$_3$ was added (final conc. 50 mM, pH=8.5) followed by 10 (1 of 10 mM solution of sulfosuccinimidyl 7-amino-4-methylcoumarin-3 -acetate (AMCA-sulfo-NHS; Pierce Chemicals) in water. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 microliters of water and purified on Sephadex G-25 gel filtration column (0.5x5 cm) to remove any free fluorescent reagent, if present. The modified tRNA was stored frozen (−70° C.) in small aliquots in order to avoid free-thaws.

To the above aminoacylated-tRNA solution, 2.5 (1 of 1N NaHCO$_3$ (final conc. 50 mM, pH=8.5) and 20 (1 of DMSO was added followed by 10 (1 of 10 mM solution of succinimidyl 7-amino-methyl-amino-coumarin acetate (AMCA-NHS; Molecular Probes) in DMSO. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 microliter of water and purified on Sephadex G-25 gel filtration column (0.5x5 cm) to remove any free fluorescent reagent, if present. The modified tRNA was stored frozen (−70° C.) in small aliquots in order to avoid free-thaws.

In this case, the coumarin-methionine-tRNA$^{fmet}$ formed using the non-sulfonated form of coumarin-NHS (AMCA-NHS) when used in standard E. coli S30 translation mixtures generated very low levels of detectable fluorescent bands when detected using UV light from a standard UV transilluminator. In contrast, the sulfonated form (AMCA-sulfo-NHS) when added using the same procedures led to easily detectable bands using the UV-transilluminator.

Attempts to incorporate coumarin using an initiator tRNA by modifying the α-amino group of methionine have been reported in the literature but failed. Coumarin attachment to a initiator tRNA subsequently required more extensive and complicated chemical attachment using a chemical cross linker. This was achieved by first aminoacylating the tRNA with methionine followed by reaction of aminoacylated tRNA with DTDG monosuccinimidyl ester (DTDG is Dithiodiglycolic acid). The reaction product was then reduced using DTT and subsequently reacted with CPM (3-(4'-Maleimidophenyl)-4-methyl-diethylamino coumarin. (Odom, O. W, Kudlicki, W and Hardestry, B. 1998. In vitro engineering using acyl-derivatized tRNA, In Protein synthesis: Methods and Protocols, PP.93–103, Humana press, Totowa, N.J.). Due to the need for special procedures designed for each marker, such an approach is not practical for general attachment of a wide variety of markers to tRNAs through post-chemical aminoacylation procedures.

One likely factor that makes sulfonated NHS reagents used for postchemical aminoacylation of tRNAs is its solubility in aqueous buffer. In contrast, non-sulfonated reagents such as the BIDOPY FL NHS reagent require organic buffer such as DMSO for postchemical modification. While it is still not clear why use of organic buffers lowers the overall marker incorporation, one possibility is that hydrolysis of the aminoacyl bond formed between the amino acid and tRNA reduces the overall level of modification.

EXAMPLE 15

Imparting Water Solubility

In general, the property of water solubility can be imparted to chemical reagents in several ways. Some of these are summarized below:

Introduction of polar functional group into leaving group (such as sulfonated-NHS).

Introduction of the polar functional group into a spacer arm.

Introduction of the polar functional group into the reagent moiety itself.

While the introduction of the —SO$_3^-$Na$^+$(sulfo-) group is peferred, other polar ionizable groups (such as DSP) can also be used where DSP is shown below:

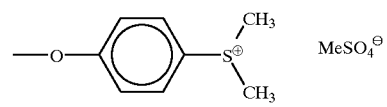

Final water soubility can be engineered into a spacer arm for eample by using a polyether spacer (e.g. one based on tetraethylene glycol). In general, any moiety that has a free carboxyl group can be converted into its sulfo-NHS active ester. This reaction involves N-hydroxy-slfosuccinimide (monosodium salt), the marker and a coupling agent such as DCC (dicyclohexylcarbodiimide):

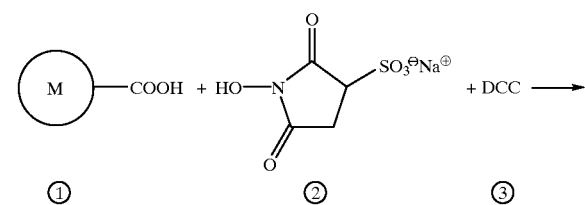

-continued

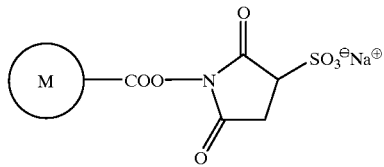

In a typical reaction, marker 1, 55 mmol, is dissolved in 10 ml DMF (dimethylformamide) and (2) (5 mmol) is added, followed by (3) (1.1 equivalents). The mixture is stirred overnight at room temperature, precipitate filtered off, and the filtrate evaporated under reduced pressure at room temperature. The product is purified if necessary using column chromatography or is recrystallized.

One preferred embodiment of this invention involves the post-chemical modification of tRNAs to form a misaminoacylated tRNA by using markers that contain a sulfonated NHS reagent. While such reagents are not generally available commercially, such reagents can be routinely produced out of a variety of useful markers. For example, fluoroescein, which has a high fluorescent quantum yield for both UV and visible excitation could be prepared in a form which contains a sulfonated NHS ester.

EXAMPLE 16

Triple Marker System

In this example, a three marker system is employed to detect nascent proteins, i.e. an N-terminus marker, a C-terminus marker, and an affinity marker (the latter being an endogenous affinity marker). The experiment involves 1) preparation of a tRNA with a marker, so that a marker can be introduced (during translation) at the N-terminus of the protein; 2) translation of hemolysin with nucleic acid coding for wild type and mutant hemolysin; and 4) quantitation of the markers.

1. Preparation of Biotin-methionyl-tRNA$^{fmet}$

The purified tRNA$^{fmet}$ (Sigma Chemicals, St. Louis, Mo.) was first aminoacylated with methionine. The typical aminoacylation reaction contained 1500 picomoles (~1.0 OD$_{260}$) of tRNA, 20 mM imidazole-HCl buffer, pH 7.5, 10 mM MgCl$_2$, 1 mM methionine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 µl). The coupling of NHS-biotin to the α-amino group of methionine was carried out in 50 mM sodium bicarbonate buffer, pH 8.0 by incubating the aminoacylated tRNA$^{fmet}$ (25 µl) with NHS-biotin (final concentration=2 mM) for 10 min at 0° C. and the reaction was quenched by the addition of free lysine (final concentration=100 mM). The modified tRNA was precipitated with ethanol and passed through Sephadex G-25 gel filtration column (0.5×5 cm) to remove any free reagent, if present.

2. In vitro Translation of α-HL DNA

A WT and Amber (at position 135) mutant plasmid DNA was using coding for α-hemolysin (α-HL), a 32 kDa protein bearing amino acid sequence His-His-His-His-His-His (His-6) SEQ ID NO:5 at its C-terminal. In vitro translation of WT and amber mutant α-HL gene (Amb 135) was carried out using E. coli T7 circular transcription/translation system (Promega Corp., Wisconsin, Wis.) in presence of Biotin-methionyl-tRNA$^{fmet}$ (AmberGen, Inc.). The translation reaction of 100 µl contained 30 µl E. coli extract (Promega Corp., Wisconsin, Wis.), 40 µl premix without amino acids, 10 µl amino acid mixture (1 mM), 5 µg of plasmid DNA coding for WT and mutant α-HL, 150 picomoles of biotin-methionyl-tRNA$^{fmet}$ and RNase-free water. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 6 mM magnesium acetate. From the translation reaction premix, n-formyl-tetrahydrofolate (fTHF) was omitted. The translation was carried out at 37° C. for 1 hour. The translation reaction mixture incubated without DNA is taken as control. After the translation reaction mixture was diluted with equal volume of TBS (Tris-buffered saline, pH 7.5). Each sample was divided into two aliquots and processed individually as described below.

3. Preparation of Anti-α-HL Antibody Microtiter Plate

Anti-rabbit-IgG coated microtiter plate (Pierce Chemicals, Rockford, Ill.) was washed with Superblock buffer solution (Pierce) and incubated with 100 µg/ml of anti-α-HL polyclonal antibody solution (Sigma Chemicals, St. Louis, Mo.) prepared in Superblock buffer on microtiter plate shaker for 1 hour at room temperature. The plate was then washed (3 times×200 µl) with Superblock buffer and stored at 4° C. till further use.

4. Quantitation of N-terminal (Biotin) Marker

The translation reaction mixture (50 µl) for the control, WT and amber α-HL DNA were incubated in different wells of anti-α-HL microtiter plate for 30 minutes on the shaker at room temperature. After incubation, the wells were washed 5 times (5–10 min each) with 200 µl Superblock buffer and the supernatant were discarded. To these wells, 100 µl of 1:1000 diluted streptavidin-horse radish peroxidase (Streptavidin-HRP; 0.25 mg/ml; Promega) was added and the plate was incubated at room temperature for 20 min under shaking conditions. After the incubation, excess streptavidin-HRP was removed by extensive washing with Superblock buffer (5 times×5 min each). Finally, 200 µl of substrate for HRP (OPD in HRP buffer; Pierce) was added and the HRP activity was determined using spectrophotometer by measuring absorbance at 441 nm.

5. Quantitation of C-terminal (His-6-tag) marker

Translation reaction mixture (50 µl) from example 2 for control, WT and Amber α-HL DNA were incubated in different wells of anti-α-HL microtiter plate for 30 min on the shaker at room temperature. After incubation, the wells were washed 5 times (5–10 min each) with 200 µl Superblock buffer and the supernatant were discarded. To these wells, 100 µl of 1:1000 diluted anti-His-6 antibody (ClonTech, Palo Alto, Calif.) was added to the well and incubated at room temperature for 20 min under shaking conditions. After the incubation, excess antibodies were removed with extensive washing with Superblock buffer (5 times×5 min each). Subsequently, the wells were incubated with secondary antibody (anti-mouse IgG-HRP, Roche-BM, Indianapolis, Ind.) for 20 min at room temperature. After washing excess 2$^{nd}$ antibodies, HRP activity was determined as described above.

6. Gel-Free Quantitation of N- and C-Terminal Markers

The results of the above-described quantitation are shown in FIGS. 23A (quantitation of N-terminal, Biotin marker) and FIG. 23B (quantitation of C-terminal, His-6 marker). In case of in vitro transcription/translation of WT α-HL DNA in presence of biotin-methionyl-tRNA, the protein synthesized will have translated His-6 tag at the C-terminal of the protein and some of the α-HL molecules will also carry biotin at their N-terminus which has been incorporated using biotinylated-methionine-tRNA. When the total translation reaction mixture containing α-HL was incubated on anti-α-HL antibody plate, selectively all the α-HL will bind to the plate via interaction of the antibody with the endogenous affinity marker. The unbound proteins can be washed away and the N- and C-terminal of the bound protein can be quantitated using Streptavidin-HRP and anti-His-6 antibodies, respectively. In case of WT α-HL, the protein will carry both the N-terminal (biotin) and C-terminal (His-6) tags and hence it will produce HRP signal in both the cases where streptavidin-HRP and secondary antibody-HRP conjugates against His-6 antibody used (HL, FIG. 23A). On the other hand, in case of amber mutant α-HL, only N-terminal fragment of α-HL (first 134 amino acids) will be produced and will have only N-terminal marker, biotin, but will not have His-6 marker due to amber mutation at codon number 135. As a result of this mutation, the protein produced using amber α-HL DNA will bind to the antibody plate but will only produce a signal in the case of strepavidin-HRP (HL-AMB, FIG. 23A) and not for anti-HisX6 antibodies (HL-AMB, FIG. 23B).

EXAMPLE 17

Electrophoretic Mobility Shift Assay (EMSA)

To demonstrate the changes in the electrophoretic mobility of fluorescently labeled nascent protein on the SDS-gels either due to proteolysis or oligomerization in presence of membranes, we have use plasmid DNA of α-hemolysin (α-HL) which codes 32 kDa protein bearing a sequence His-His-His-His-His-His (His-6) SEQ ID NO:5 at its C-terminal. In vitro translation of α-HL gene was carried out using $E.$ $coli$ T7 circular transcription/translation system (Promega Corp., Wisconsin-Madison, Wis.) in presence of BODIPY-FL-methionyl-tRNA$^{fmet}$ (AmberGen, Inc.) This experiment involved 1) preparation of the tRNA-marker for introduction of the N-terminus marker during translation, 2) translation, 3) purification, 4) protease treatment or 5) oligomerization.

1. Preparation of BODIPY-FL-methionyl-tRNA

BODIPYL-FL-methionyl-tRNA was prepared by first aminoacylating pure tRNA$^{fmet}$ (Sigma Chemicals, St. Louis, Mo.) using methionine and subsequently modifying α-amino group of methionine using BODIPY-FL-SSE (4,4-difluoro-5,7-dimethyl-4-bora-3a,4a-diaza-s-indacene propionic acid, sulfosuccinimidyl ester; Molecular Probes, Eugene, Oreg.). The typical aminoacylation reaction (100 μl) contained 1500 picomoles (~1.0 OD$_{260}$) of tRNA, 20 mM imidazole-HCI buffer, pH 7.5, 10 mM MgCl$_2$, 1 mM methionine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 μl). The coupling of BODIPY-FL-SSE to the α-amino group of methionine was carried out in 50 μl reaction volume using 50 mM sodium bicarbonate buffer, pH 8.0 by incubating 25 μl aminoacylated tRNA$^{fmet}$ (1.5 nanomoles) with 10 μl of BODIPY-FL-SSE (10 mM) for 10 min at 0° C. and the reaction was quenched by the addition of free lysine (final concentration=100 mM). The modified tRNA was precipitated with ethanol, and the pellet was dissolved in RNase-free water and passed through Sephadex G-25 gel filtration column (0.5×5 cm) to remove any free fluorescent reagent, if present.

2. In Vitro Translation of α-hemolysin DNA

The translation reaction of 100 μL contained 30 μl $E.$ $coli$ extract (Promega Corp., Wisconsin, Wis.), 40 μl premix without amino acids, 10 μl amino acid mixture (1 mM), 5 μg of plasmid DNA coding for α-HL, 150 picomoles of BODIPY-FL-methionyl-tRNA$^{fmet}$ and RNase free water. The premix (1×) contains 57 mM HEPES, pH 8.2, 36 mM ammonium acetate, 210 mM potassium glutamate, 1.7 mM DTT, 4% PEG 8000. 1.25 mM ATP, 0.8 mM GTP, 0.8 mM UTP, 60 mM phosphoenol pyruvate, 0.6 mM cAMP and 6 mM magnesium acetate. From the translation reaction premix, n-formyl-tetrahydrofolate (fTHF) was omitted. The translation was carried out at 37° C. for 1 hour. The translation reaction mixture incubated without DNA is taken as control.

3. Purification of Hls-6-α-HL

Fifty microliters of the translation reaction mixture (from above) was subjected to Talon-Sepharose (ClonTech, Palo Alto, Calif.) chromatography for the purification of Hls-6-α-HL. This was carried out by loading the crude extract onto the Talon-Sepharose column which was pre-equilibrated with 50 mM Tris-HCl pH 8.0 containing 150 mM NaCI and washing the column to remove unbound proteins. The bound protein was then eluted by adding 100 mM imidazole in the above buffer. The eluted α-HL was dialyzed against 50 mM Tris-HCl buffer, pH 7.5.

4. EMSA for Protease Detection

The purified fluorescently labeled (α-HL (~5 μg) (example 3) was incubated with 0.0.5 μg of pure trypsin (Sigma Chemicals, St. Louis, Mo.) in 50 nM acetate buffer, pH 5.0 (100:1; protein:protease ratio) for 5 min at 37° C. The proteolysis reaction was arrested by the addition of 1×SDS-gel loading buffer and boiling the samples for 5 min. The SDS-PAGE was carried out as described by Laemmli (Laemmli, U. K. 1970, Nature 227, 680–685) using 4–20% gradient gel (ready-gel, Bio-Rad, Richmond, Calif.). After the gel electrophoresis, the gel was visualized using Fluor-lmager F595 (Molecular Dynamics, Sunnyvale, Calif.).

Trypsin was used under very limited conditions (single-hit kinetics) to obtain very defined cleavage of α-HL (50 mM acetate buffer, pH 5.0, 100:1: protein:protease ratio, 5 min at 37° C). Under these conditions, the glycine rich loop in α-HL is most susceptible to cleavage and as a result proteolytic fragment of 17 kDa was observed (Vecesey-Semjen, B., Knapp, S., Mollby, R., Goot, F. G. 1999, Biochemistry, 38 4296–4302). When the fluorescently labeled α-HL was subjected to very mild trypsin treatment, it resulted a cleavage of α-HL yielding the N-terminal fragment of approximately 17–18 kDa mass as evidence by change in the mobility of fluorescent band on SDS-PAGE (FIG. 24: Lane 1 shows untreated protein and Lane 2 shows protease treated protein). This result indicates that such assay could be used to screen for proteases or any other enzymatic activities like kinase, transferase etc. that could potentially result in the electrophoretic mobility shift of the nascent protein. Though we have used pure nascent protein for this particular assay, there is no reason why one can not use a nascent protein without any purification (total translation reaction mixture).

5. EMSA for Oligomerization of Nascent Protein on Membranes

The total translation reaction mixture (10 μl) (see above) was incubated in absence and in presence of rabbit red blood cells (rRBCs, Charles River Farm, Conn.) for 30 min. at 0° C. After the incubation, rRBCs were washed free of excess unbound α-HL and the rRBCs were incubated in Tris buffer saline (TBS) containing 1 mg/ml BSA (TBSA) at 37° C. for 20 min during which lysis of rRBCs occurred. The rRBC membranes were isolated after centrifugation, dissolved in 1×SDS-gel loading buffer and subjected to SDS-PAGE (4–20% gradient gel) without heating the sample. After the gel electrophoresis, the gel was visualized using FluorImager F595.

α-HL is expressed a soluble monomeric protein and in presence of various membranes it can oligomerize to form heptameric pore (Walker, B., Krishnasastry, M., Zorn, L., Kasianowicz, J. and Bayley, H., 1992, J. Biol. Chem. 267, 10902–10909). In addition, some intermediate forms of the oligomers were also observed. In this experiment, in order to see the applicability of EMSA to detect the shift in mobility of α-HL due to oligomerization in presence lipid membranes, the total translation reaction mixture (with out any purification) was used. When the total translation extract containing nascent α-HL was incubated with rRBCs, it resulted in the oligomerization of α-HL on the rRBC membranes yielding a distinct fluorescent bands corresponding to various molecular masses that were SDS-resistant (FIG. 25: Lane 1 shows untreated protein only and Lane 2 shows protein treated with rRBCs).

This result demonstrates that such assay could be used to study proteins, interact with variety of natural and artificial membranes and as a result the mobility of the protein in shifted.

EXAMPLE 18
Incorporation Using Lysyl-tRNA$^{lys}$

This example describes the incorporation of fluorescent labels into nascent protein using lysyl-tRNA$^{lys}$. More specifically, a variety of fluorescent molecules were incorporated into 1) hemolysin during translation in an E coli translation system, and 2) luciferase during translation in a wheat germ system, using lysyl tRNA$^{lys}$. The experiment involved 1) preparation of the tRNA-marker compounds, 2) translation, and 3) detection on gels.

1. Preparation of Fluorescent Labeled Misaminoacylated tRNA$^{lys}$

The purified tRNA$^{lys}$ (Sigma Chemicals, St. Louis, Mo.) was first amino-acylated with lysine. The typical aminoacylation reaction (100 μl) contained 1500 picomoles (~1.0 $OD_{260}$) of tRNA, 20 mM imidazole-HCl buffer, pH 7.5, 10 mM $MgCl_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 μl). The coupling of NHS-derivatives of various fluorescent molecules (see Table 2) to the ε-amino group of lysine was carried out in 50 mM CAPS buffer, pH 10.5 by incubating the aminoacylated tRNA$^{lys}$ (25 μl) with fluorescent reagent (final concentration=2 mM) for 10 min at 0° C. and the reaction was quenched by the addition of free lysine (final concentration=100 mM). The modified tRNA was precipitated with ethanol, dissolved in 50 μl of RNase-free water and passed through Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis (Varshney, U., Lee, C. P. & RajBhandary, U. L., 1991 J. Biol. Chem. 266, 24712–24718).

2. Cell Free Synthesis of Proteins in Prokaryotic (E. coli) Translation Extracts The typical translation reaction mixture (10 μl) contained 3 μl of E. coli extract (Promega Corp., Wisconsin-Madison, Wis.), 4 μl of premix, 1 μl of amino acid mix (1 mM), 30 picomoles of fluorescent-lysyl-tRNA and 0.5 μg of α hemolysin (αHL) plasmid DNA. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM CTP, 60 mM phosphoenal pyruvate, 0.6 mM cAMP and 6 mM magnesium acetate. The translation reaction was allowed to proceed for 45 min at 37° C. For SDS-PAGE, 4–10 μl aliquot of the reaction mix was precipitated with 5-volume acetone and the precipitated proteins were collected by centrifugation. The pellet was dissolved in 1×loading buffer and subjected to SDS-PAGE after boiling for 5 min. SDS-PAGE was carried out according to Laemmmli (Lammli, U. K. 1970, Nature, 227, 680–685).

3. Cell-free Synthesis in Eukaryotic (TnT Wheat Germ) Translation Extracts.

The typical translation reaction mixture (10 μl) contained 5 μl of TnT wheat germ extract (Promega Corp., Wisconsin-Madison, Wis.), 0.4 μl of TnT reaction buffer, 1 μl of amino acid mix (1 mM), 0.2 μl of T7 RNA polymerase, 30 picomoles of fluorescent-lysyl-tRNA and 0.5 μg of luciferase RNA (Promega) and RNase-free water. The translation reaction ws allowed to proceed for 45 min at 30° C. and reaction mixture was centrifuged for 5 min to remove insoluble material. The clarified extract was then precipitated with 5-volume acetone and the precipitated proteins were collected by centrifugation. The pellet was dissolved in 1×loading buffer and subjectd to SDS-PAGE after boiling for 5 min. SDS-PAGE was carried out according to Laenmuli (Lammli, U. K. 1970), Nature, 227, 680–685).

4. Detection of Nascent Protein

The gel containing nascent proteins was scanned using FluorImager F595 (Molecular Dynamics, Sunnyvale, Calif. using Argon laser (488 nm) as excitation source, in addition, the nascent proteins in polyacrylamide gels were also detected using an UV-transilluminator and the photographs were carried out using Polaroid camera fitted with Tiffen green filter (Polaroid, Cambridge, Mass.). FIGS. 26A and 26B show the results of in vitro translation of α-HL produced in presence of various fluorescent tRNA$^{lys}$. It is clear from the results one can incorporate a variety of fluorescent molecules into nascent protein using misaminoacylated tRNA (fluorophore-modified lysyl-tRNA$^{lys}$) including dyes like NBD, fluorescein derivatives etc. (Lane 1: No DNA control; lane 2: BODIPY-FL-SSE (4,4-difluoro-5,7-dimethyl-4-bora-3a, 4a-diaza-s-indacene propionic acid, sulfosuccinimidyl ester); lane 3: BODIPY-FL-SE (4,4-difluoro-5,7-dimethyl-4bora-3a, 4a-diaza-s-indacene proionic acid, succinimidyl ester); lane 4 : NBD-X-SE (Succinimidyl 6-(7-nitrobenz-2-oxa-1,3-diazol-4-yl) aminohexanoate); lane 5; BODIPY-TMR-SE ((6-994,4-difluoro-1,3-dimethyl-5-(4-methoxyphenyl)-4-bora-3a, 4a-diaza-s-indacene-2-propionyl) amino) hexanoic acid, succinimidyl ester); lane 6: BODIPY-R6G-SE ((4,4-difluoro-5-phenyl-4-bora-3a,4a-diaza-s-indacene-3propionic acid, succinimidyl ester); lane 7; FAM-SE (5-(6-)-carboxyfluorescein, succinimidyl ester); lane 8:SFX-SE (6-fluorescein-5-(and 6-)carboxyamido)hexonoic acid, succinimidyl ester); lane 9: PyMPO-SE(1-(3-(succinimidyloxycarbonyl)benzyl)-4-(5-(4-methoxyphenyl) oxazol-2-yl) pyridininium bromide (PyMPO)) and lane 10: TAMRA-SE (6-(tetramethylrhodamine-5-(and-6)-carboxamido)hexanoic acid, succinimidyl ester).

EXAMPLE 19
NHS-derivatives of Coumarin

Given the above noted results for the two BODIPY molecules (i.e. BODIPY-FL-SSE and BODIPY-FL-SE), attempts were made to derivative other markers to make them suitable for incorporation. The present example involves 1) the preparation of the labeled tRNA, 2) translation, and 3) detection of the nascent protein containing the label (or marker).

1. Preparation of Fluorescent Labeled Misaminoacylated tRNA$^{fmet}$

The purified tRNAm$^{fmet}$ (Sigma Chemicals, St. Louis, Mo.) was first aminoacylated with methionine. The typical aminoacylation reaction (100 µl) contained 1500 picomoles (approximately 1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in the water (25 µl). The coupling of NHS-derivatives of coumarin [namely sulfosuccinimidyl 7-amino-4-methylcoumarin-3-acetate [1] (AMCA-sulfo-NHS; Pierce Chemicals), Alexa 350-N-hydroxy-succinimide ester (Molecular Probes) and succinimidyl 7-amethyl-amino-coumarin acetate (AMCA-NHS: Molecular Probes)] to the α-amino group of methionine was carried out in 50 mM sodium bicarbonate buffer, pH 8.5 by incubating the aminoacylated tRNA$^{fmet}$ (25 µl) with fluorescent reagent (final concentration=2 mM) for 10 min at 0° C. and the reaction was quenched by the addition of free lysine (final concentration=100 mM). In case of AMCA-NHS, reagent was dissolved in DMSO and the coupling reaction was carried out in presence of 40% DMSO. The modified tRNA was precipitated with ethanol, dissolved in 50 µl of RNase-free water and passed through Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis (Varshney, U., Lee, C. P. & RajBhandary, U. L., 1991, *J. Biol. Chem.* 266, 24712–24718).

2. Cell Free Systhesis of Proteins in Prokaryotic (*E. coli*) Translation Extracts The typical translation reaction mixture (10 µl) contained 3 µl of *E. coli* S-30 extract (Promega Corp., Wisconsin-Madison, Wis.), 4 µl of premix, 1 µl of amino acid mix (1 mM), 30 picomoles of fluorescent-methionyl-tRNA and 0.5 µg of α-hemolysin (α-HL) plasmid DNA. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 6 mM magnesium acetate. The translation reaction was allowed to proceed for 45 min at 37° C. For SDS-PAGE, 4–10 µaliquot of the reaction mix was precipitated with 5-volume acetone and the precipitated proteins were collected by centrifugation. The pellet was dissolved in 1×loading buffer and subjected to SDS-PAGE after boiling for 5 min. SDS-PAGE was carried out according to Laemmli (Laemmli, U. K. 1970, *Nature*, 277, 680–685).

3. Detection of Nascent Protein

The gel containing nascent proteins was visualized using an UV-transilluminator equipped with long wavelength TV bulb (>300 nm) and the photographs were carried out using Polaroid camera fitted with Tiffen green filter (Polaroid, Cambridge, Mass.). FIG. 27 indicates that the result in vitro translation of α-HL produced in presence of various fluorescent tRNAs (Lane 1 shows the results for the no DNA control; Lane 2 shows the results with Met-tRNA$^{fmet}$ modified with AMCA-NHS; Lane 3 shows the results with Met-tRNA$^{fmet}$ modified with AMCA-sulfo-NHS; and Lane 4 shows the results with Met-tRNA$^{fmet}$ modified with Alexa-NHS). Clearly, one can incorporate the coumarin derivative molecules into nascent protein using misaminoacylated tRNA which are modified with the water soluble NHS-esters of fluorescent molecules (lane 3). Moreover, a dye with negative charge (Alexa, lane 4) seems to not incorporate as well as its neutral counterpart (AMCA; lane 3).

From the above results and general teachings of the present specification, one skilled in the art can select other markers and render them (e.g. chemically render them) suitable for incorporation in accordance with the methods of the present invention.

EXAMPLE 20
Capillary Electrophoresis

The example describes the use of capillary electrophoresis (CE) for detection of in vitro synthesized fluorescent proteins by mobility shift. The example describes 1) the preparation of the tRNA comprising a BODIPY marker, 2) in vitro translation, 3) purification, 4) protease digestion and 5) detection by mobility shift assay.

1. Preparation of BODIPY-FL-methionyl-tRNA$^{fmet}$

The tRNA$^{fmet}$ was aminoacylated with the methionine. In typical reaction, 1500 picomoles (~1.0 OD$_{260}$) of tRNA was incubated for 45 min at 37° C. in aminoacylation mix using an excess of aminoacyl tRNA-synthetases. The aminoacylation mix comprised 20 mM imidazole-HCl buffer, pH 7.5, 150 mM NaCl, 10 mM MgCl$_2$, 2 mM ATP and 1600 units of aminoacyl tRNA-synthetase. The extent of aminoacylation was determined by acid-urea gel as well as by using $^{35}$S-methionine. After incubation, the mixture was neutralized by adding 0.1 volume of 3 M sodium acetate, pH 5.0 and subjected to chloroform:acid phenol (pH 5.0) extraction (1:1). Ethanol (2.5 volumes) was added to the aqueous phase and the tRNA pellet obtained was dissolved in water (37.5 ul) and used for modification. To the above aminoacylated-tRNA solution, 2.5 ul of 1N NaHCO$_3$ was added (final conc. 50 mM, pH=8.5) followed by 10 ul of 10 mM solution of BODIPY-FL-SSE (Molecular Probes) in water. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ul of water and purified on Sephadex G-25 gel filtration column (0.5×5 cm) to remove any free fluorescent reagent, if present. The modified tRNA was stored frozen (−70° C.) in small aliquots in order to avoid free-thaws.

2. In Vitro Translation of α-hemolysin DNA

The translation reaction of 500 ul contained 150 µl *E. coli* extract (Promega Corp., Wisconsin, Wis.), 200 ul premix without amino acids, 50 ul amino acid mixture (1 mM), 25 ug of plasmid DNA coding for α-HL, 1000 picomoles of BODIPY-FL-methionyl-tRNA$^{fmet}$ and RNase free water. The premix (1×) contains 57 mM HEPES, pH 8.2, 36 mM ammonium acetate, 210 mM potassium glutamate, 1.7 mM DTT, 4% PEG 8000, 1.25 mM ATP, 0.8 mM GTP, 0.8 mM UTP, 0.8 mM CTP, 60 mM phosphoenol pyruvate, 0.6 mM cAMP and 16 mM magnesium acetate. From the translation reaction premix, n-formyl-tetrahydrofolate (fTHF) was omitted. The translation was carried out at 37° C. for 1 hour. The translation reaction mixture incubated without DNA is taken as control.

3. Purification of His-6-α-HL

Five hundred microliters of the translation reaction mixture (see step 2 above) was subjected to Talon-Sepharose (ClonTech, Polo Alto, Calif.) chromatography for the purification of His-6-α-HL. This was carried out by loading the crude extract onto the Talon-Sepharose column which was pre-equilibrated with 50 mM Tris-HCl, pH 8.0 containing 150 mM NaCl and washing the column to remove unbound proteins. The bound protein was then eluted by adding 100 mM imidazole in the above buffer. The eluted α-HL was dialyzed against 50 mM Tris-HCl buffer, pH 7.5. The fluorescence of purified and dialyzed α-HL was checked on Molecular Dynamics FluorImager F595.

4. Protease Digestion

The purified fluorescently labeled α-HL (~5 ug) (see step 3 above) was incubated with 0.1 ug of pure trypsin (Sigma Chemicals, St. Louis, Mo.) in 50 mM Tris-HCl buffer, pH 7.5 (50:1; protein:protease ratio) for 10 min at room temperature. The proteolysis reaction was arrested by the addition of 1×CE-SDS-gel loading buffer and boiling the samples for 10 min.

5. Mobility Shift Assay

The SDS-capillary gel electrophoresis (SDS-CGE) was performed on a Bio-Rad BioFocus 3000CE system. The capillary was fused-silica with a 75 um ID, 24 cm total length and 19.5 cm to the detector. Fifty microliters of fluorescently labeled protein sample (α-HL) was mixed with 50 ul of SDS-CGE sample loading buffer and incubated at 95° C. for 10 min. The capillary was rinsed with 0.1 M NaOH, 0.1 M HCl and SDS-run buffer for 60, 60 and 120 sec respectively, prior to each injection. Sample were injected using electrophoretic injection (20 sec at 10 kV). Separation was performed at 15 kV (constant voltage) for 25 min. Capillary and sample was maintained at 20° C. The detection of sample was carried out using 488 nm Argon laser and 520 nm emission filter.

The results of SDS-CGE are shown in the FIG. 28. As seen in the Figure, fluorescently label α-HL migrates as a major species eluting around 24 min under the electrophoresis conditions (Top panel). In addition, the electrophoregram also show the presence of minor impurities present in the sample, which are eluting around 17 and 20.5 min. When the fluorescently labeled-α-HL sample was treated with trypsin and analyzed using SDS-CGE, it showed peaks eluting earlier (13, 14 and 15 min) and major peak at 21 min (Bottom panel). This result indicated that the α-HL was proteolysed by the trypsin and various proteolytic fragments have N-terminal fluorescently labeled are seen in the electrophoregram.

EXAMPLE 21

Incorporation of Three Markers

This is an example wherein a protein is generated in vitro under conditions where N- and C-terminal markers are incorporated along with a marker incorporated using a misaminoacylated tRNA. The Example involves 1) PCR with primers harboring N-terminal and C-terminal detectable markers, 2) preparation of the tRNA, 3) in vitro translation, 4) detection of nascent protein.

1. PCR of α-Hemolysin DNA

Plasmid DNA for α-hemolysin, pT7-WT-H6-αHL, was amplified by PCR using following primers. The forward primer (HL-5) was: 5'-GAATTC TAATACGACTCACTATAGGGTTAACTTTAAGAAGG AGATATACATATG GAACAAAAATTAATCTCGGAAGAGGATTTGGCAG ATTCTGATATTAATATTAAAACC3' SEQ ID NO:11 and the reverse primer (HL-3) was: 5'-AGCTTCATTA ATGATGGTGATGGTGGTGAC 3'SEQ ID NO:12. The underlined sequence in forward primer is T7 promoter, the region in bold corresponds to ribosome binding site (Shine-Dalgamo's sequence), the bold and underlined sequences involve the C-myc epitope and nucleotides shown in italics are the complimentary region of α-hemolysin sequence. In the reverse primer, the underlined sequence corresponds to that of HisX6 epitope. The PCR reaction mixture of 100 ul contained 100 ng template DNA, 0.5 uM each primer, 1 mM MgCl$_2$, 50 ul of PCR master mix (Qiagen, Calif.) and nuclease free water (Sigma Chemicals, St. Louis, Mo.) water. The PCR was carried out using Hybaid Omni-E thermocyler (Hybaid, Franklin, Mass.) fitted with hot-lid using following conditions: 95° C. for 2 min, followed by 35 cycles consisted of 95° C for 1 min, 61° C. for 1 min and 72° C. for 2 min and the final extension at 72° C. for 7 min. The PCR product was then purified using Qiagen PCR clean-up kit (Qiagen, Calif.). The purified PCR DNA was used in the translation reaction.

2. Preparation of BODIPY-FL-lysyl-tRNA$^{lys}$

The purified tRNA$^{lys}$ (Sigma Chemicals, St. Louis, Mo.) was first aminoacylated with lysine. The typical aminoacylation reaction contained 1500 picomoles (~1.0 OD$_{260}$) of tRNA, 20 mM imidazole-HCl buffer, pH 7.5, 10 mM MgCl$_2$, 1 mM lysine, 2 mM ATP, 150 mM NaCl and excess of aminoacyl tRNA-synthetases (Sigma Chemicals, St. Louis, Mo.). The reaction mixture was incubated for 45 min at 37° C. After incubation, the reaction mixture was neutralized by adding 0.1 volume of 3 M sodium acetate, pH 5.0 and subjected to chloroform:acid phenol extraction (1:1). Ethanol (2.5 volumes) was added to the aqueous phase and the tRNA pellet obtained was dissolved in water (35 ul). To this solution 5 ul of 0.5 M CAPS buffer, pH 10.5 was added (50 mM final conc.) followed by 10 ul of 10 mM solution of BODIPY-FL-SSE. The mixture was incubated for 10 min at 0° C. and the reaction was quenched by the addition of lysine (final concentration=100 mM). To the resulting solution 0.1 volume of 3 M NaOAc, pH=5.0 was added and the modified tRNA was precipitated with 3 volumes of ethanol. Precipitate was dissolved in 50 ul of water and purified on Sephadex G-25 gel filtration column (0.5×5 cm) to remove any free fluorescent reagent, if present. The modified tRNA was stored frozen (−70° C.) in small aliquots in order to avoid free-thaws. The modification extent of the aminoacylated-tRNA was assessed by acid-urea gel electrophoresis. Varshney et al., *J. Biol. Chem.* 266:24712–24718 (1991).

3. Cell-free Synthesis of Proteins in Eukaryotic (Wheat Germ) Translation Extracts The typical translation reaction mixture (20 ul) contained 10 ul of TnT wheat germ extract (Promega Corp., Wisconsin-Madison, Wis.), 0.8 ul of TnT reaction buffer, 2 ul of amino acid mix (1 mM), 0.4 ul of T7 RNA polymerase, 30 picomoles of BODIPY-FL-lysyl-tRNA$^{lys}$, 1–2 ug plasmid or PCR DNA (Example 1) and RNase-free water. The translation reaction was allowed to proceed for 60 min at 30° C. and reaction mixture was centrifuged for 5 min to remove insoluble material. The clarified extract was then precipitated with 5-volumes of acetone and the precipitated proteins were collected by centrifugation. The pellet was dissolved in 1×loading buffer and subjected to SDS-PAGE after boiling for 5 min. SDS-PAGE was carried out according to Laemmli, *Nature,* 227:680–685.

4. Detection of Nascent Protein

After the electrophoresis, gel was scanned using FluorImager 595 (Molecular Dymanics, Sunnyvale, Calif.)

equipped with argon laser as excitation source. For visualization of BODIPY-FL labeled nascent protein, we have used 488 nm as the excitation source as it is the closest to its excitation maximum and for emission, we have used 530+/−30 filter. The gel was scanned using PMT voltage 1000 volts and either 100 or 200 micron pixel size.

The results are shown in FIG. 29. It can be seen from the Figure that one can in vitro produce the protein from the PCR DNA containing desired marker(s) present. In the present case, the protein (α-hemolysin) has a C-myc epitope at N-terminal and HisX6 epitope at C-terminal. In addition, BODIPY-FL, a fluorescent reporter molecule is incorporated into the protein. Lane 1: α-Hemolysin plasmid DNA control; lane 2: no DNA control; lane 3: PCR α-hemolysin DNA and lane 4: hemolysin amber 135 DNA. The top (T) and bottom (B) bands in all the lane are from the non-specific binding of fluorescent tRNA to some proteins in wheat germ extract and free fluorescent-tRNA present in the translation reaction, respectively.

EXAMPLE 22

Primer Design

It is not intended that the present invention be limited to particular primers. A variety of primers are contemplated for use in the present invention to ultimately incorporate markers in the the nascent protein (as explained above). The Example involves 1) PCR with primers harboring markers, 2) in vitro translation, and 3) detection of nascent protein.

For PCR the following primers were used: forward primer: 5'GGATCC<u>TAATACGACTCACTATAG</u>GGAGACCACCATG GAACAAAAATTAATATCGGAAGAGGATTTGAATG TTTCTCCATACAGGTCACGGGGA-3' SEQ ID NO:13 Reverse Primer: 5'-TTATTAATGATGGTGATGGTGGTG<u>TTCTGTAGGAATGGTATCTCGTTTTTC</u>-3' SEQ ID NO:14. The underlined sequence in the forward primer is T7 promoter, the bold and underlined sequences involve the C-myc epitope and nucleotides shown in italics are the complimentary region of α-hemolysin sequence. In the reverse primer, the underlined sequence corresponds to that of HisX6 epitope. A PCR reaction mixture of 100 ul can be used containing 100 ng template DNA, 0.5 uM each primer, 1 mM $MgCl_2$, 50 ul of PCR master mix (Qiagen, Calif.) and nuclease free water (Sigma Chemicals, St. Louis, Mo.) water. The PCR can be carried out using Hybaid Omni-E thermocyler (Hybaid, Franklin, Mass.) fitted with hot-lid using following conditions: 95° C. for 2 min, followed by 35 cycles consisted of 95° C. for 1 min, 61° C. for 1 min and 72° C for 2 min and the final extension at 72° C. for 7 min. The PCR product can then be purified using Qiagen PCR clean-up kit (Qiagen, Calif.). The purified PCR DNA can then be used in a variety of translation reactions. Detection can be done as described above.

Other embodiments and uses of the invention will be apparent to those skilled in the art from consideration of the specification and practice of the invention disclosed herein. It is intended that the specification and examples be considered exemplary only, with the scope of particular embodiments of the invention indicated by the following claims.

TABLE 2

| Name and Molecular weight | Formula | Fluorescence Properties |
|---|---|---|
| BODIPY-FL, SSE M. WT. 491 | | Excitation = 502 nm Emmision = 510 nm Extinction = 75,000 |
| NBD M. WT. 391 | | Excitation = 466 nm Emmision = 535 nm Extinction = 22,000 |
| Bodipy-TMR-X, SE M. WT. 608 | | Excitation = 544 nm Emmision = 570 nm Extinction = 56,000 |

TABLE 2-continued

| Name and Molecular weight | Formula | Fluorescence Properties |
|---|---|---|
| Bodipy-R6G M. WT. 437 | | Excitation = 528 nm Emmision = 547 nm Extinction = 70,000 |
| Fluorescein (FAM) M. WT. 473 | | Excitation = 495 nm Emmision = 520 nm Extinction = 74,000 |
| Fluorescein (SFX) M. WT. 587 | | Excitation = 494 nm Emmision = 520 nm Extinction = 73,000 |
| PyMPO M. WT. 582 | | Excitation = 415 nm Emmision = 570 nm Extinction = 26,000 |
| 5/6-TAMRA M. WT. 528 | | Excitation = 546 nm Emmision = 576 nm Extinction = 95,000 |

| Enzyme/Protein | −FluoroTag ™ tRNA Translation reaction | +FluoroTag ™ tRNA Translation reaction |
|---|---|---|
| α-Hemolysin $OD_{415nm}/\mu l$ | 0.085 | 0.083 |
| Luciferase RLU/$\mu l$ | 79052 | 78842 |
| DHFR $\Delta OD_{339nm}/\mu l$ | 0.050 | 0.064 |

What is claimed is:

1. A method of creating a tRNA/marker conjugate, comprising:
   a) providing i) a tRNA molecule charged with an amino acid and ii) a fluorophore marker, wherein said fluorophore marker comprises the structure set forth in FIG. 19; and
   b) reacting said tRNA molecule with said marker to create a tRNA/marker conjugate, wherein the amino acid of said tRNA of said tRNA/marker conjugate is covalently bonded to said marker.

2. The method of claim 1, further comprising:
   c) introducing said tRNA/marker conjugate into a translation system under conditions such that said marker is incorporated into a nascent protein.

3. The method of claim 1, wherein the tRNA molecule is charged by chemical or enzymatic means.

4. The method of claim 1, wherein said tRNA molecule is an initiator tRNA molecule.

5. The method of claim 1, wherein said tRNA molecule is a suppressor tRNA molecule.

6. The method of claim 2, further comprising:
   d) detecting said nascent protein containing said marker.

7. The method of claim 2, wherein the translation system comprises a cell-free translation system.

8. The method of claim 2, wherein the translation system is a cellular translation system selected from the group consisting of tissue culture cells, primary cells, cells in vivo, isolated immortalized cells, human cells and combinations thereof.

9. The method of claim 6, further comprising:
   e) isolating said detected nascent protein.

10. The method of claim 6, wherein the nascent protein detected is selected from recombinant gene products, gene fusion products, enzymes, cytokines, carbohydrate and lipid binding proteins, nucleic acid binding proteins, hormones, immunogenic proteins, human proteins, viral proteins, bacterial proteins, parasitic proteins and fragments and combinations thereof.

11. The method of claim 6, wherein said nascent protein detected is functionally active.

12. The method of claim 7, wherein the cell-free translation system is selected from the group consisting of *Escherichia coli* lysates, wheat germ extracts, insect cell lysates, rabbit reticulocyte lysates, frog oocyte lysates, dog pancreatic lysates, human cell lysates, mixtures of purified or semi-purified translation factors and combinations thereof.

13. The method of claim 7, wherein said cell-free translation system is incubated at a temperature of between about 25° C. to about 45° C.

14. The method of claim 7, wherein the cell-free translation system is a continuous flow or dialysis system.

15. A method of introducing conjugates into a translation system, comprising:
   a) providing i) a translation system ii) a first charged tRNA/marker conjugate comprising a first amino acid covalently bound to a marker, wherein said marker comprises the structure set forth in FIG. 19, and ii) a second charged tRNA/marker conjugate comprising a second amino acid covalently bonded to a marker, wherein said marker comprises the structure set forth in FIG. 19, and wherein said first amino acid is different from said second amino acid; and
   b) introducing said first and second conjugates into said translation system.

16. A kit, comprising:
   a) a first containing means containing at least one component of a protein synthesis system;
   b) a second containing means containing a tRNA/marker conjugate, wherein said marker of said tRNA/marker conjugate comprises the structure set forth in FIG. 19.

17. The kit of claim 16, wherein said tRNA of said tRNA/marker conjugate is an initiator tRNA.

18. The kit of claim 16, wherein said tRNA of said tRNA/marker conjugate is a suppressor tRNA.

19. The kit of claim 16, wherein said component of said protein synthesis system comprises ribosomes.

20. A tRNA/marker conjugate, wherein said marker comprises the structure set forth in FIG. 19.

21. A method of creating a charged tRNA molecule, comprising:
   a) providing i) a tRNA molecule and ii) a conjugate comprising an amino acid covalently bonded to a fluorophore marker, wherein said fluorophore marker comprises the structure set forth in FIG. 19; and
   b) creating a charged tRNA molecule with said conjugate.

22. The method of claim 21, further comprising:
   c) introducing said charged tRNA into a translation system under conditions such that said marker is incorporated into a nascent protein.

23. A charged tRNA molecule produced according to the method of claim 21.

24. The method of claim 22, further comprising:

d) detecting said nascent protein containing said marker.

25. The method of claim 24, further comprising:

e) isolating said detected nascent protein.

26. A method of introducing a conjugate into a translation system, comprising:

a) providing i) a translation system ii) a charged tRNA/ marker conjugate comprising a amino acid covalently bound to a marker, wherein said marker comprises the structure set forth in FIG. 19;

b) introducing said conjugate into said translation system under conditions such that said marker is incorporated into a nascent protein; and c) visualizing said nascent protein on a gel virtue of said marker.

* * * * *